US012275983B2

(12) United States Patent
Crameri et al.

(10) Patent No.: US 12,275,983 B2
(45) Date of Patent: Apr. 15, 2025

(54) PROCESSES FOR THE PRODUCTION OF OLIGONUCLEOTIDES

(71) Applicant: GLAXOSMITHKLINE INTELLECTUAL PROPERTY DEVELOPMENT LIMITED, Stevenage (GB)

(72) Inventors: Andreas Crameri, Stevenage (GB); Malcolm Leithhead Hill, Stevenage (GB); David Graham Tew, Stevenage (GB)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 1163 days.

(21) Appl. No.: 16/833,724

(22) Filed: Mar. 30, 2020

(65) Prior Publication Data

US 2020/0277659 A1 Sep. 3, 2020

Related U.S. Application Data

(63) Continuation of application No. 15/643,535, filed on Jul. 7, 2017, now Pat. No. 10,640,812.

(30) Foreign Application Priority Data

Jul. 11, 2016 (GB) ..................... 1612011

(51) Int. Cl.
*C12Q 1/6811* (2018.01)
*C07H 1/00* (2006.01)
*C07H 21/00* (2006.01)
*C12N 9/00* (2006.01)
*C12Q 1/6855* (2018.01)
*C12Q 1/686* (2018.01)
*G01N 30/02* (2006.01)

(52) U.S. Cl.
CPC ............. *C12Q 1/6811* (2013.01); *C07H 1/00* (2013.01); *C07H 21/00* (2013.01); *C12N 9/93* (2013.01); *C12Q 1/6855* (2013.01); *C12Q 1/686* (2013.01); *C12Y 605/01001* (2013.01); *C07K 2319/20* (2013.01); *C12Q 2600/106* (2013.01); *C12Q 2600/156* (2013.01); *G01N 2030/027* (2013.01)

(58) Field of Classification Search
None
See application file for complete search history.

(56) References Cited

U.S. PATENT DOCUMENTS

| 5,516,664 | A | 5/1996 | Hyman |
| 5,547,843 | A | 8/1996 | Studier et al. |
| 5,602,000 | A | 2/1997 | Hyman |
| 5,998,175 | A | 12/1999 | Akhavan-Tafti |
| 6,004,826 | A | 12/1999 | Segev |
| 6,110,668 | A | 8/2000 | Strizhov et al. |
| 6,660,229 | B2 | 12/2003 | Cantor ................. C12Q 1/6872 422/116 |
| 6,867,294 | B1 | 3/2005 | Sanghvi et al. |
| 7,033,753 | B1 | 4/2006 | Kool ..................... C12Q 1/6827 435/6.1 |
| 7,695,906 | B2 | 4/2010 | Schatz .................. C12N 15/10 435/6.11 |
| 8,148,065 | B1 | 4/2012 | Wallace |
| 10,640,812 | B2 | 5/2020 | Crameri et al. |
| 2003/0008306 | A1 | 1/2003 | Turnbull et al. |
| 2003/0073081 | A1 | 4/2003 | Mukai et al. |
| 2003/0120035 | A1 | 6/2003 | Gao et al. |
| 2003/0228602 | A1 | 12/2003 | Parker et al. |
| 2004/0248104 | A1 | 12/2004 | Yakhini et al. |
| 2016/0108382 | A1 | 4/2016 | Efcavitch et al. |

FOREIGN PATENT DOCUMENTS

| CN | 1350581 A | 5/2002 |
| CN | 101889096 A | 11/2010 |
| CN | 105506125 A | 4/2016 |
| EP | 1130113 A1 | 9/2001 |
| JP | 2019-525917 A | 9/2019 |
| WO | 1989012696 A1 | 12/1989 |
| WO | 2000005412 A1 | 2/2000 |
| WO | WO 00/50870 A1 | 8/2000 |
| WO | 0127326 A2 | 4/2001 |
| WO | 0129211 A2 | 4/2001 |
| WO | 0164864 A2 | 9/2001 |
| WO | WO 01/71037 A1 | 9/2001 |
| WO | 2003106679 A1 | 12/2003 |
| WO | 2004029223 A2 | 4/2004 |
| WO | 2006071568 A2 | 7/2006 |
| WO | 2009043112 A1 | 4/2009 |
| WO | WO 2009/097673 A1 | 8/2009 |
| WO | 2012010711 A1 | 1/2012 |
| WO | 2014041337 A1 | 3/2014 |
| WO | 2018011067 A2 | 1/2018 |

OTHER PUBLICATIONS

International Preliminary Report on Patentability dated Nov. 26, 2018 for PCT/EP2017/067049.
International Patent Application No. PCT/EP2017/067049 Written Response to the EPO dated Aug. 13, 2018.
Karkare et al. "Promising nucleic acid analogs and mimics: characteristic features and applications of PNA, LNA, and morpholino" 71 Applied Microbiology and Biotechnology 575-586 (2006).
Frank et al. "A new generation for the simultaneous chemical synthesis of large numbers of oligonucleotides: segmental solid supports" 11(13) Nucleic Acids Research 4365-4377 (1983).
Toy et al. "Soluble Polymer-Supported Organic Synthesis" 33(8) Accounts of Chemical Research 546-554 (2000).

(Continued)

*Primary Examiner* — Nancy J Leith
(74) *Attorney, Agent, or Firm* — Carly Shanahan

(57) ABSTRACT

Disclosed herein are novel processes for the production of oligonucleotides that are suitable for use in the production of chemically modified oligonucleotides, such as those for use in therapy.

20 Claims, 19 Drawing Sheets
Specification includes a Sequence Listing.

(56) References Cited

OTHER PUBLICATIONS

El-Sagheer, et al., "Biocompatible artificial DNA linker that is read through by DNA polymerases and is functional in *Escherichia coli*", PNAS; 2011; 108 (28) 11338-11343.

Qiu, et al., "Solid phase click ligation for the synthesis of very long oligonucleotides", Chemical Communications; Issue 62; 49; 2013; pp. 6959-6961.

Hili et al., "DNA ligase-mediated translation of DNA into densely functionalized nucleic acid polymers.", Journal of the American Chemical Society, American Chemical Society, United States, United States, (Dec. 20, 2012), vol. 135, No. 1, doi:10.1021/ja311331m, ISSN 1520-5126, pp. 98-101, XP002785248.

Lei et al., "A High-Fidelity Codon Set for the T4 DNA Ligase-Catalyzed Polymerization of Modified Oligonucleotides.", ACS Combinatorial Science Dec. 14, 2015, (Dec. 14, 2015), vol. 17, No. 12, doi:10.1021/acscombsci.5b00119, ISSN 2156-8944, pp. 716-721, XP002785249.

Lundin et al., "Oligonucleotide Therapies: The Past and the Present", Human Gene Therapy, Mary Ann Liebert, Inc. Publishers, GB, GB , (Aug. 1, 2015), vol. 26, No. 8, doi:10.1089/hum.2015.070, ISSN 1043-034, pp. 475-485, XP055376603.

Goodchild, "Conjugates of Oligonucleotides and Modified Oligonucleotides: A Review of their Synthesis and Properties," Bioconjugate Chemistry, American Chemical Society, US, US , (May 1, 1990), vol. 01., No. 03., doi:10.1021/bc00003a001, ISSN 1043-1802, pp. 165-187, XP000174627.

Verma et al., "Modified oligonucleotides: synthesis and strategy for users.", Annual Review of Biochemistry, Palto Alto, CA, US, US, (Jan. 1, 1998), vol. 67, doi:10.1146/annurev.biochem.67.1.99, ISSN 0066-4154, pp. 99-134, XP008157631.

Zhao et al., "Effects of 2'-O-methyl nucleotide on ligation capability of T4 DNA ligase", Acta Biochimica Biophysica Sinica, Blackwell Publishing, Inc., Malden, MA, US, US , (Sep. 1, 2014), vol. 46, No. 9, doi:10.1093/abbs/gmu058, ISSN 1672-9145, pp. 727-737, XP055790513.

Suzuki et al., "Simple and Rapid Enzymatic Method for the Synthesis of Single-Strand Oligonucleotides Containing Trifluorothymidine", Nucleosides, Nucleotides & Nucleic Acids, Taylor & Francis, US, US , (Nov. 30, 2010), vol. 29, No. 11-12, doi:10.1080/15257770.2010.535803, ISSN 1525-7770, pp. 896-904, XP055439750.

Pengpumkiat et al., "Rapid Synthesis of a Long Double-Stranded Oligonucleotide from a Single-Stranded Nucleotide Using Magnetic Beads and an Oligo Library", PLoS One, (Mar. 1, 2016), vol. 11, No. 3, doi:10.1371/journal.pone.0149774, p. e0149774, XP055805167.

Chen et al., "Template-directed chemical ligation to obtain 3'-3' and 5'-5' phosphodiester DNA linkages", Scientific reports, Nature Publishing Group, England, England , doi:10.1038/srep04595, (Apr. 4, 2014), p. 4595, Scientific reports, URL: https://www.ibg.uu.se/digitalAssets/164/c_164781-I_3-k_islam-saiful-arbete-1336.pdf, XP055511016.

Stark et al., "An RNA ligase-mediated method for the efficient creation of large, synthetic RNAs", RNA, Cambridge University Press on behalf of the RNA Society, (Jan. 1, 2006), vol. 12, No. 11, doi:10.1261/rna.93506, ISSN 13558382, pp. 2014-2019, XP055047162.

Vanmeert et al., "Rational design of an XNA ligase through docking of unbound nucleic acids to toroidal proteins", Nucleic Acids Research, Oxford University Press, GB, GB , (Jul. 26, 2019), vol. 47, No. 13, doi:10.1093/nar/gkz551, ISSN 0305-1048, pp. 7130-7142, XP055954856.

Kershaw et al., "Splint Ligation of RNA with T4 DNA Ligase", Christopher J. Kershaw, Raymond T. O'keefe, Boegel, Sebastian [HerausgeberIn], Bioinformatics for Cancer Immunotherapy : Methods and Protocols, New York, NY, Springer , (Jan. 1, 2013), vol. 941, pp. 257-269, doi:10.1007/978-1-62703-113-4_19, ISBN 978-1-0716-0326-0, XP055523744.

Noll et al., "Purification of Small Interfering RNA Using Nondenaturing Anion-Exchange Chromatography", Nucleic Acid Therapeutics, Mary Ann Liebert, Inc. Publishers, US, US , (Dec. 1, 2011), vol. 21, No. 6, doi:10.1089/nat.2011.0317, ISSN 2159-3337, pp. 383-393, XP055954863.

ATDBIO: "Gene Synthesis," Jan. 5, 2016, [Retrieved on Feb. 8, 2019] Retrieved from URL: https://www.aidbio.com/content/63/Gene-synthesis.

Barany F., "The Ligase Chain Reaction in a PCR World," PCR Methods Applications, Cold Spring Harbor Laboratory Press, US, Aug. 1, 1991, vol. 1, No. 1, pp. 5-16, ISSN: 1054-9803.

Brill W K D., "Facile Methods to Recycle Nucleosides During Solid Phase Synthesis of Oligonucleotides", Tetrahedron Letters, 1994, vol. 35, No. 19, pp. 3041-3044.

Knunyants I.L., Chemical Encyclopedia, v. 2, Soviet Encyclopedia Publishing House, Moscow, V.Z, 1990, pp. 664-665.

Kramer M., et al., "Enzyme-Free Ligation of 5'-Phosphorylated Oligodeoxynucleotides in a DNA Nanostructure," Chemistry Biodiversity, Aug. 11, 2017, vol. 14, No. 9, p. e1700315, ISSN: 1612-1872.

Kukwikila M., et al., "Assembly of a Biocompatible Triazole-linked Gene by One-pot Click-DNA Ligation," Nature Chemistry, Sep. 11, 2017, vol. 9, No. 11, pp. 1089-1098, ISSN: 1755-4330.

Ling M.M., et al., "Approaches to DNA Mutagenesis An Overview," Analytical Biochemistry, 1997, vol. 254, No. 2, pp. 157-178.

Shivalingam A., et al., "Synthesis of Chemically Modified DNA," Biochemical Society Transactions, Jun. 15, 2016, vol. 44, No. 3, pp. 709-715, ISSN: 0300-5127.

Tarantul, Explanatory Dictionary of Molecular and Cellular Biotechnology, Moscow, 2015, vol. 1, p. 411. [retrieved online https://www.ncbi.nlm.nih.gov/nlmcatalog/101685659] English Title only.

Taylor J.W., et al., 1985, vol. 13, N24, pp. 8749-8764.

Single Template

Repeating Template

Gaps or overlaps arising from
missing or additional nucleotides

Impurities arising from missing
or additional nucleotides

SEQUENCE LISTING

<160> NUMBER OF SEQ ID NOS: 62

<210> SEQ ID NO 1
<211> LENGTH: 20
<212> TYPE: DNA
<213> ORGANISM: Artificial sequence
<220> FEATURE:
<223> OTHER INFORMATION: Example 1 desired product oligonucleotide
      sequence ("target")

<400> SEQUENCE: 1
ggccaaacct cggcttacct                                               20

<210> SEQ ID NO 2
<211> LENGTH: 23
<212> TYPE: DNA

<213> ORGANISM: Artificial sequence
<220> FEATURE:
<223> OTHER INFORMATION: Example 1-4, 6, 10 and 11 template
      oligonucleotide sequence

<400> SEQUENCE: 2
tttaggtaag ccgaggtttg gcc                                            23

<210> SEQ ID NO 3
<211> LENGTH: 487
<212> TYPE: PRT
<213> ORGANISM: Enterobacteria phage T4

<400> SEQUENCE: 3

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335
```

-continued

```
Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 4
<211> LENGTH: 488
<212> TYPE: PRT
<213> ORGANISM: Artificial sequence
<220> FEATURE:
<223> OTHER INFORMATION: Wild type T4 DNA ligase protein sequence (when
      fused to CBD)

<400> SEQUENCE: 4

Gly Ser Ile Leu Lys Ile Leu Asn Glu Ile Ala Ser Ile Gly Ser Thr
1               5                   10                  15

Lys Gln Lys Gln Ala Ile Leu Glu Lys Asn Lys Asp Asn Glu Leu Leu
            20                  25                  30

Lys Arg Val Tyr Arg Leu Thr Tyr Ser Arg Gly Leu Gln Tyr Tyr Ile
        35                  40                  45

Lys Lys Trp Pro Lys Pro Gly Ile Ala Thr Gln Ser Phe Gly Met Leu
    50                  55                  60

Thr Leu Thr Asp Met Leu Asp Phe Ile Glu Phe Thr Leu Ala Thr Arg
65                  70                  75                  80

Lys Leu Thr Gly Asn Ala Ala Ile Glu Glu Leu Thr Gly Tyr Ile Thr
                85                  90                  95

Asp Gly Lys Lys Asp Asp Val Glu Val Leu Arg Arg Val Met Met Arg
            100                 105                 110

Asp Leu Glu Cys Gly Ala Ser Val Ser Ile Ala Asn Lys Val Trp Pro
        115                 120                 125

Gly Leu Ile Pro Glu Gln Pro Gln Met Leu Ala Ser Ser Tyr Asp Glu
    130                 135                 140

Lys Gly Ile Asn Lys Asn Ile Lys Phe Pro Ala Phe Ala Gln Leu Lys
145                 150                 155                 160

Ala Asp Gly Ala Arg Cys Phe Ala Glu Val Arg Gly Asp Glu Leu Asp
                165                 170                 175

Asp Val Arg Leu Leu Ser Arg Ala Gly Asn Glu Tyr Leu Gly Leu Asp
            180                 185                 190

Leu Leu Lys Glu Glu Leu Ile Lys Met Thr Ala Glu Ala Arg Gln Ile
```

```
                195                 200                 205
His Pro Glu Gly Val Leu Ile Asp Gly Glu Leu Val Tyr His Glu Gln
    210                 215                 220

Val Lys Lys Glu Pro Glu Gly Leu Asp Phe Leu Phe Asp Ala Tyr Pro
225                 230                 235                 240

Glu Asn Ser Lys Ala Lys Glu Phe Ala Glu Val Ala Glu Ser Arg Thr
                245                 250                 255

Ala Ser Asn Gly Ile Ala Asn Lys Ser Leu Lys Gly Thr Ile Ser Glu
            260                 265                 270

Lys Glu Ala Gln Cys Met Lys Phe Gln Val Trp Asp Tyr Val Pro Leu
        275                 280                 285

Val Glu Ile Tyr Ser Leu Pro Ala Phe Arg Leu Lys Tyr Asp Val Arg
290                 295                 300

Phe Ser Lys Leu Glu Gln Met Thr Ser Gly Tyr Asp Lys Val Ile Leu
305                 310                 315                 320

Ile Glu Asn Gln Val Val Asn Asn Leu Asp Glu Ala Lys Val Ile Tyr
                325                 330                 335

Lys Lys Tyr Ile Asp Gln Gly Leu Glu Gly Ile Ile Leu Lys Asn Ile
            340                 345                 350

Asp Gly Leu Trp Glu Asn Ala Arg Ser Lys Asn Leu Tyr Lys Phe Lys
        355                 360                 365

Glu Val Ile Asp Val Asp Leu Lys Ile Val Gly Ile Tyr Pro His Arg
370                 375                 380

Lys Asp Pro Thr Lys Ala Gly Gly Phe Ile Leu Glu Ser Glu Cys Gly
385                 390                 395                 400

Lys Ile Lys Val Asn Ala Gly Ser Gly Leu Lys Asp Lys Ala Gly Val
                405                 410                 415

Lys Ser His Glu Leu Asp Arg Thr Arg Ile Met Glu Asn Gln Asn Tyr
            420                 425                 430

Tyr Ile Gly Lys Ile Leu Glu Cys Glu Cys Asn Gly Trp Leu Lys Ser
        435                 440                 445

Asp Gly Arg Thr Asp Tyr Val Lys Leu Phe Leu Pro Ile Ala Ile Arg
450                 455                 460

Leu Arg Glu Asp Lys Thr Lys Ala Asn Thr Phe Glu Asp Val Phe Gly
465                 470                 475                 480

Asp Phe His Glu Val Thr Gly Leu
                485

<210> SEQ ID NO 5
<211> LENGTH: 20
<212> TYPE: RNA
<213> ORGANISM: Artificial sequence
<220> FEATURE:
<223> OTHER INFORMATION: Example 2 target sequence

<400> SEQUENCE: 5
ggccaaaccu cggcuuaccu                                              20

<210> SEQ ID NO 6
<211> LENGTH: 482
<212> TYPE: PRT
<213> ORGANISM: Enterobacteria phase CC31

<400> SEQUENCE: 6

Met Ile Leu Asp Ile Ile Asn Glu Ile Ala Ser Ile Gly Ser Thr Lys
1               5                   10                  15
```

Glu Lys Glu Ala Ile Ile Arg Arg His Lys Asp Asn Glu Leu Leu Lys
                20                  25                  30

Arg Val Phe Arg Met Thr Tyr Asp Gly Lys Leu Gln Tyr Tyr Ile Lys
            35                  40                  45

Lys Trp Asp Thr Arg Pro Lys Gly Asp Ile His Leu Thr Leu Glu Asp
        50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Glu Lys Gly Ile Glu
            130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
        195                 200                 205

Val Met Ile Asp Gly Glu Leu Val Tyr His Ala Ser Thr Leu Pro Ala
210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
                245                 250                 255

Lys Ser Leu Lys Gly Thr Ile Ser Ala Lys Glu Ala Ala Gly Met Lys
            260                 265                 270

Phe Gln Val Trp Asp Tyr Val Pro Leu Asp Val Val Tyr Ser Glu Gly
        275                 280                 285

Lys Gln Ser Gly Phe Ala Tyr Asp Val Arg Phe Arg Ala Leu Glu Leu
            290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
            340                 345                 350

Thr Arg Ser Lys Asn Leu Tyr Lys Phe Lys Glu Val Ile Thr Ile Asp
        355                 360                 365

Leu Arg Ile Val Asp Ile Tyr Glu His Ser Lys Gln Pro Gly Lys Ala
    370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
                405                 410                 415

Arg Thr Arg Ile Trp Glu Asn Lys Asn Asp Tyr Ile Gly Gly Val Leu
            420                 425                 430

Glu Ser Glu Cys Asn Gly Trp Leu Ala Ala Glu Gly Arg Thr Asp Tyr

```
                435                 440                 445
Val Lys Leu Phe Leu Pro Ile Ala Ile Lys Met Arg Arg Asp Lys Asp
    450                 455                 460

Val Ala Asn Thr Phe Ala Asp Ile Trp Gly Asp Phe His Glu Val Thr
465                 470                 475                 480

Gly Leu

<210> SEQ ID NO 7
<211> LENGTH: 483
<212> TYPE: PRT
<213> ORGANISM: Artificial sequence
<220> FEATURE:
<223> OTHER INFORMATION: Wild-type Enterobacteria phage CC31 DNA ligase
      protein sequence (when fused to CBD)

<400> SEQUENCE: 7

Gly Ser Ile Leu Asp Ile Ile Asn Glu Ile Ala Ser Ile Gly Ser Thr
1               5                   10                  15

Lys Glu Lys Glu Ala Ile Ile Arg Arg His Lys Asp Asn Glu Leu Leu
            20                  25                  30

Lys Arg Val Phe Arg Met Thr Tyr Asp Gly Lys Leu Gln Tyr Tyr Ile
        35                  40                  45

Lys Lys Trp Asp Thr Arg Pro Lys Gly Asp Ile His Leu Thr Leu Glu
    50                  55                  60

Asp Met Leu Tyr Leu Leu Glu Glu Lys Leu Ala Lys Arg Val Val Thr
65                  70                  75                  80

Gly Asn Ala Ala Lys Glu Lys Leu Glu Ile Ala Leu Ser Gln Thr Ser
                85                  90                  95

Asp Ala Asp Ala Glu Val Val Lys Lys Val Leu Leu Arg Asp Leu Arg
            100                 105                 110

Cys Gly Ala Ser Arg Ser Ile Ala Asn Lys Val Trp Lys Asn Leu Ile
        115                 120                 125

Pro Glu Gln Pro Gln Met Leu Ala Ser Ser Tyr Asp Glu Lys Gly Ile
    130                 135                 140

Glu Lys Asn Ile Lys Phe Pro Ala Phe Ala Gln Leu Lys Ala Asp Gly
145                 150                 155                 160

Ala Arg Ala Phe Ala Glu Val Arg Gly Asp Glu Leu Asp Asp Val Lys
                165                 170                 175

Ile Leu Ser Arg Ala Gly Asn Glu Tyr Leu Gly Leu Asp Leu Leu Lys
            180                 185                 190

Gln Gln Leu Ile Glu Met Thr Lys Glu Ala Arg Glu Arg His Pro Gly
        195                 200                 205

Gly Val Met Ile Asp Gly Glu Leu Val Tyr His Ala Ser Thr Leu Pro
    210                 215                 220

Ala Gly Pro Leu Asp Asp Ile Phe Gly Asp Leu Pro Glu Leu Ser Lys
225                 230                 235                 240

Ala Lys Glu Phe Lys Glu Glu Ser Arg Thr Met Ser Asn Gly Leu Ala
                245                 250                 255

Asn Lys Ser Leu Lys Gly Thr Ile Ser Ala Lys Glu Ala Ala Gly Met
            260                 265                 270

Lys Phe Gln Val Trp Asp Tyr Val Pro Leu Asp Val Tyr Ser Glu
        275                 280                 285

Gly Lys Gln Ser Gly Phe Ala Tyr Asp Val Arg Phe Arg Ala Leu Glu
    290                 295                 300

Leu Met Val Gln Gly Tyr Ser Gln Met Ile Leu Ile Glu Asn His Ile
```

```
               305                 310                 315                 320
    Val His Asn Leu Asp Glu Ala Lys Val Ile Tyr Arg Lys Tyr Val Asp
                    325                 330                 335

Glu Gly Leu Glu Gly Ile Ile Leu Lys Asn Ile Gly Ala Phe Trp Glu
                    340                 345                 350

Asn Thr Arg Ser Lys Asn Leu Tyr Lys Phe Lys Glu Val Ile Thr Ile
                    355                 360                 365

Asp Leu Arg Ile Val Asp Ile Tyr Glu His Ser Lys Gln Pro Gly Lys
                    370                 375                 380

Ala Gly Gly Phe Tyr Leu Glu Ser Glu Cys Gly Leu Ile Lys Val Lys
    385                 390                 395                 400

Ala Gly Ser Gly Leu Lys Asp Lys Pro Gly Lys Asp Ala His Glu Leu
                    405                 410                 415

Asp Arg Thr Arg Ile Trp Glu Asn Lys Asn Asp Tyr Ile Gly Gly Val
                    420                 425                 430

Leu Glu Ser Glu Cys Asn Gly Trp Leu Ala Ala Glu Gly Arg Thr Asp
                    435                 440                 445

Tyr Val Lys Leu Phe Leu Pro Ile Ala Ile Lys Met Arg Arg Asp Lys
    450                 455                 460

Asp Val Ala Asn Thr Phe Ala Asp Ile Trp Gly Asp Phe His Glu Val
    465                 470                 475                 480

Thr Gly Leu

<210> SEQ ID NO 8
<211> LENGTH: 497
<212> TYPE: PRT
<213> ORGANISM: Shigella phage Shfl25875

<400> SEQUENCE: 8

Met Ile Leu Asp Ile Leu Asn Gln Ile Ala Ala Ile Gly Ser Thr Lys
    1               5                   10                  15

Thr Lys Gln Glu Ile Leu Lys Lys Asn Lys Asp Asn Lys Leu Leu Glu
                    20                  25                  30

Arg Val Tyr Arg Leu Thr Tyr Ala Arg Gly Ile Gln Tyr Tyr Ile Lys
                    35                  40                  45

Lys Trp Pro Gly Pro Gly Glu Arg Ser Gln Ala Tyr Gly Leu Leu Glu
                    50                  55                  60

Leu Asp Asp Met Leu Asp Phe Ile Glu Phe Thr Leu Ala Thr Arg Lys
    65                  70                  75                  80

Leu Thr Gly Asn Ala Ala Ile Lys Glu Leu Met Gly Tyr Ile Ala Asp
                    85                  90                  95

Gly Lys Pro Asp Asp Val Glu Val Leu Arg Arg Val Met Met Arg Asp
                    100                 105                 110

Leu Glu Val Gly Ala Ser Val Ser Ile Ala Asn Lys Val Trp Pro Gly
                    115                 120                 125

Leu Ile Gln Leu Gln Pro Gln Met Leu Ala Ser Ala Tyr Asp Glu Lys
                    130                 135                 140

Leu Ile Thr Lys Asn Ile Lys Trp Pro Ala Phe Ala Gln Leu Lys Ala
    145                 150                 155                 160

Asp Gly Ala Arg Cys Phe Ala Glu Val Arg Asp Gly Val Gln Phe
                    165                 170                 175

Phe Ser Arg Ala Gly Asn Glu Tyr His Gly Leu Thr Leu Leu Ala Asp
                    180                 185                 190

Glu Leu Met Glu Met Thr Lys Glu Ala Arg Glu Arg His Pro Asn Gly
```

```
            195                 200                 205
Val Leu Ile Asp Gly Glu Leu Val Tyr His Ser Phe Asp Ile Lys Lys
    210                 215                 220

Ala Val Ser Ser Gly Asn Asp Leu Ser Phe Leu Phe Gly Asp Asn Glu
225                 230                 235                 240

Glu Ser Glu Glu Val Gln Val Ala Asp Arg Ser Thr Ser Asn Gly Leu
                245                 250                 255

Ala Asn Lys Ser Leu Gln Gly Thr Ile Ser Pro Lys Glu Ala Glu Gly
            260                 265                 270

Met Val Leu Gln Ala Trp Asp Tyr Val Pro Leu Asp Glu Val Tyr Ser
        275                 280                 285

Asp Gly Lys Ile Lys Gly Gln Lys Tyr Asp Val Arg Phe Ala Ala Leu
    290                 295                 300

Glu Asn Met Ala Glu Gly Phe Lys Arg Ile Glu Pro Ile Glu Asn Gln
305                 310                 315                 320

Leu Val His Asn Leu Asp Glu Ala Lys Val Val Tyr Lys Lys Tyr Val
                325                 330                 335

Asp Gln Gly Leu Glu Gly Ile Ile Leu Lys Asn Arg Asp Ser Tyr Trp
            340                 345                 350

Glu Asn Lys Arg Ser Lys Asn Leu Ile Lys Phe Lys Glu Val Ile Asp
        355                 360                 365

Ile Ala Leu Glu Val Val Gly Tyr Tyr Glu His Ser Lys Asp Pro Asn
    370                 375                 380

Lys Leu Gly Gly Val Glu Leu Val Ser Arg Cys Arg Arg Ile Thr Thr
385                 390                 395                 400

Asp Cys Gly Ser Gly Phe Lys Asp Thr Thr His Lys Thr Val Asp Gly
                405                 410                 415

Val Lys Val Leu Ile Pro Leu Asp Glu Arg His Asp Leu Asp Arg Glu
            420                 425                 430

Arg Leu Met Ala Glu Ala Arg Glu Gly Lys Leu Ile Gly Arg Ile Ala
        435                 440                 445

Asp Cys Glu Cys Asn Gly Trp Val His Ser Lys Gly Arg Glu Gly Thr
    450                 455                 460

Val Gly Ile Phe Leu Pro Ile Ile Lys Gly Phe Arg Phe Asp Lys Thr
465                 470                 475                 480

Glu Ala Asp Ser Phe Glu Asp Val Phe Gly Pro Trp Ser Gln Thr Gly
                485                 490                 495

Leu

<210> SEQ ID NO 9
<211> LENGTH: 498
<212> TYPE: PRT
<213> ORGANISM: Artificial sequence
<220> FEATURE:
<223> OTHER INFORMATION: Wild-type Shigella phage Shf125875 DNA ligase
      protein sequence (when fused to CBD)

<400> SEQUENCE: 9

Gly Ser Ile Leu Asp Ile Leu Asn Gln Ile Ala Ala Ile Gly Ser Thr
1               5                   10                  15

Lys Thr Lys Gln Glu Ile Leu Lys Asn Lys Asp Asn Lys Leu Leu
                20                  25                  30

Glu Arg Val Tyr Arg Leu Thr Tyr Ala Arg Gly Ile Gln Tyr Tyr Ile
            35                  40                  45

Lys Lys Trp Pro Gly Pro Gly Glu Arg Ser Gln Ala Tyr Gly Leu Leu
```

```
                50                  55                  60
Glu Leu Asp Asp Met Leu Asp Phe Ile Glu Phe Thr Leu Ala Thr Arg
 65                  70                  75                  80

Lys Leu Thr Gly Asn Ala Ala Ile Lys Glu Leu Met Gly Tyr Ile Ala
                 85                  90                  95

Asp Gly Lys Pro Asp Asp Val Glu Val Leu Arg Arg Val Met Met Arg
                100                 105                 110

Asp Leu Glu Val Gly Ala Ser Val Ser Ile Ala Asn Lys Val Trp Pro
                115                 120                 125

Gly Leu Ile Gln Leu Gln Pro Gln Met Leu Ala Ser Ala Tyr Asp Glu
                130                 135                 140

Lys Leu Ile Thr Lys Asn Ile Lys Trp Pro Ala Phe Ala Gln Leu Lys
145                 150                 155                 160

Ala Asp Gly Ala Arg Cys Phe Ala Glu Val Arg Asp Asp Gly Val Gln
                165                 170                 175

Phe Phe Ser Arg Ala Gly Asn Glu Tyr His Gly Leu Thr Leu Leu Ala
                180                 185                 190

Asp Glu Leu Met Glu Met Thr Lys Glu Ala Arg Glu Arg His Pro Asn
                195                 200                 205

Gly Val Leu Ile Asp Gly Glu Leu Val Tyr His Ser Phe Asp Ile Lys
210                 215                 220

Lys Ala Val Ser Ser Gly Asn Asp Leu Ser Phe Leu Phe Gly Asp Asn
225                 230                 235                 240

Glu Glu Ser Glu Glu Val Gln Val Ala Asp Arg Ser Thr Ser Asn Gly
                245                 250                 255

Leu Ala Asn Lys Ser Leu Gln Gly Thr Ile Ser Pro Lys Glu Ala Glu
                260                 265                 270

Gly Met Val Leu Gln Ala Trp Asp Tyr Val Pro Leu Asp Glu Val Tyr
                275                 280                 285

Ser Asp Gly Lys Ile Lys Gly Gln Lys Tyr Asp Val Arg Phe Ala Ala
                290                 295                 300

Leu Glu Asn Met Ala Glu Gly Phe Lys Arg Ile Glu Pro Ile Glu Asn
305                 310                 315                 320

Gln Leu Val His Asn Leu Asp Glu Ala Lys Val Val Tyr Lys Lys Tyr
                325                 330                 335

Val Asp Gln Gly Leu Glu Gly Ile Ile Leu Lys Asn Arg Asp Ser Tyr
                340                 345                 350

Trp Glu Asn Lys Arg Ser Lys Asn Leu Ile Lys Phe Lys Glu Val Ile
                355                 360                 365

Asp Ile Ala Leu Glu Val Val Gly Tyr Tyr Glu His Ser Lys Asp Pro
370                 375                 380

Asn Lys Leu Gly Gly Val Glu Leu Val Ser Arg Cys Arg Arg Ile Thr
385                 390                 395                 400

Thr Asp Cys Gly Ser Gly Phe Lys Asp Thr Thr His Lys Thr Val Asp
                405                 410                 415

Gly Val Lys Val Leu Ile Pro Leu Asp Glu Arg His Asp Leu Asp Arg
                420                 425                 430

Glu Arg Leu Met Ala Glu Ala Arg Glu Gly Lys Leu Ile Gly Arg Ile
                435                 440                 445

Ala Asp Cys Glu Cys Asn Gly Trp Val His Ser Lys Gly Arg Glu Gly
                450                 455                 460

Thr Val Gly Ile Phe Leu Pro Ile Ile Lys Gly Phe Arg Phe Asp Lys
465                 470                 475                 480
```

```
Thr Glu Ala Asp Ser Phe Glu Asp Val Phe Gly Pro Trp Ser Gln Thr
            485                 490                 495

Gly Leu

<210> SEQ ID NO 10
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 10

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335
```

```
Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Arg
            355                 360                 365

Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 11
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 11

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205
```

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Gly
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 12
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 12

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

```
Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
            210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Lys
                355                 360                 365

Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 13
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 13

```
Met Ile Leu Lys Ile Leu Asn Glu Ile Ala Ser Ile Gly Ser Thr Lys
1               5                   10                  15

Gln Lys Gln Ala Ile Leu Glu Lys Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Leu Val Asp Leu Lys Ile Val Gly Ile Tyr Pro His Arg Lys
```

```
                    370                 375                 380
Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                    405                 410                 415

Ser His Glu Leu Asp Arg Thr Arg Ile Met Glu Asn Gln Asn Tyr Tyr
                    420                 425                 430

Ile Gly Lys Ile Leu Glu Cys Glu Cys Asn Gly Trp Leu Lys Ser Asp
                    435                 440                 445

Gly Arg Thr Asp Tyr Val Lys Leu Phe Leu Pro Ile Ala Ile Arg Leu
                    450                 455                 460

Arg Glu Asp Lys Thr Lys Ala Asn Thr Phe Glu Asp Val Phe Gly Asp
465                 470                 475                 480

Phe His Glu Val Thr Gly Leu
                    485

<210> SEQ ID NO 14
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 14

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                    20                  25                  30

Arg Val Tyr Arg Leu Thr Tyr Ser Arg Gly Leu Gln Tyr Tyr Ile Lys
                    35                  40                  45

Lys Trp Pro Lys Pro Gly Ile Ala Thr Gln Ser Phe Gly Met Leu Thr
                    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                    85                  90                  95

Gly Lys Lys Asp Asp Val Glu Val Leu Arg Arg Val Met Met Arg Asp
                    100                 105                 110

Leu Glu Cys Gly Ala Ser Val Ser Ile Ala Asn Lys Val Trp Pro Gly
                    115                 120                 125

Leu Ile Pro Glu Gln Pro Gln Met Leu Ala Ser Ser Tyr Asp Glu Lys
                    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                    165                 170                 175

Val Arg Leu Leu Ser Arg Ala Gly Asn Glu Tyr Leu Gly Leu Asp Leu
                    180                 185                 190

Leu Lys Glu Glu Leu Ile Lys Met Thr Ala Glu Ala Arg Gln Ile His
                    195                 200                 205

Pro Glu Gly Val Leu Ile Asp Gly Glu Leu Val Tyr His Glu Gln Val
                    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
```

245                 250                 255
Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Gln Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 15
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 15

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly 115                 120                 125
Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Gln Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 16
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 16

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65              70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Val Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415
```

```
Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 17
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 17

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285
```

```
Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Arg Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 18
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 18

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160
```

```
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
            180                 185                 190
Leu Lys Glu Glu Leu Ile Lys Met Thr Ala Glu Ala Arg Gln Ile His
        195                 200                 205
Pro Glu Gly Val Leu Ile Asp Gly Glu Leu Val Tyr His Glu Gln Val
    210                 215                 220
Lys Lys Glu Pro Glu Gly Leu Asp Phe Leu Phe Asp Ala Tyr Pro Glu
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
        275                 280                 285
Glu Ile Tyr Ser Leu Pro Ala Phe Arg Leu Lys Tyr Asp Val Arg Phe
    290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Ala Ile Asp Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Glu Cys Asn Gly Trp Leu Lys Ser Asp
        435                 440                 445
Gly Arg Thr Asp Tyr Val Lys Leu Phe Leu Pro Ile Ala Ile Arg Leu
    450                 455                 460
Arg Glu Asp Lys Thr Lys Ala Asn Thr Phe Glu Asp Val Phe Gly Asp
465                 470                 475                 480
Phe His Glu Val Thr Gly Leu
                485

<210> SEQ ID NO 19
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 19

Met Ile Leu Lys Ile Leu Asn Glu Ile Ala Ser Ile Gly Ser Thr Lys
1               5                   10                  15
Gln Lys Gln Ala Ile Leu Glu Lys Asn Lys Asp Asn Glu Leu Leu Lys
            20                  25                  30
```

-continued

```
Arg Val Tyr Arg Leu Thr Tyr Ser Arg Gly Leu Gln Tyr Tyr Ile Lys
         35                  40                  45

Lys Trp Pro Lys Pro Gly Ile Ala Thr Gln Ser Phe Gly Met Leu Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
                115                 120                 125

Leu Ile Pro Glu Gln Pro Gln Met Leu Ala Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
                210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Lys Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445
```

```
Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 20
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 20

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
            85                  90                  95

Gly Lys Lys Asp Asp Val Glu Val Leu Arg Arg Val Met Met Arg Asp
        100                 105                 110

Leu Glu Cys Gly Ala Ser Val Ser Ile Ala Asn Lys Val Trp Pro Gly
    115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
        260                 265                 270

Glu Ala Gln Cys Met Lys Phe Gln Val Trp Asp Tyr Val Pro Leu Val
    275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320
```

```
Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Arg
        355                 360                 365

Val Ile Val Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 21
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 21

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190
```

```
Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Lys
        355                 360                 365

Val Ile Glu Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 22
<211> LENGTH: 487
<212> TYPE: PRT
<213> ORGANISM: Artificial sequence
<220> FEATURE:
<223> OTHER INFORMATION: Mutant ligase (T4 backbone) protein sequence

<400> SEQUENCE: 22

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60
```

```
Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Lys
        355                 360                 365

Val Ile His Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
```

485

<210> SEQ ID NO 23
<211> LENGTH: 482
<212> TYPE: PRT
<213> ORGANISM: Artificial sequence
<220> FEATURE:
<223> OTHER INFORMATION: Mutant ligase (Enterobacteria phage CC31
      backbone - clone A4) protein sequence

<400> SEQUENCE: 23

```
Met Ile Leu Asp Ile Ile Asn Glu Ile Ala Ser Ile Gly Ser Thr Lys
1               5                   10                  15

Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
        35                  40                  45

Lys Trp Asp Thr Arg Pro Lys Gly Asp Ile His Leu Thr Leu Glu Asp
    50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Lys Gly Ile Glu
    130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
        195                 200                 205

Val Met Ile Asp Gly Glu Leu Val Tyr His Ala Ser Thr Leu Pro Ala
    210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
                245                 250                 255

Lys Ser Leu Lys Gly Thr Ile Ser Ala Lys Glu Ala Ala Gly Met Lys
            260                 265                 270

Phe Gln Val Trp Asp Tyr Val Pro Leu Asp Val Val Tyr Ser Glu Gly
        275                 280                 285

Lys Gln Ser Gly Phe Ala Tyr Asp Val Arg Phe Arg Ala Leu Glu Leu
    290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
            340                 345                 350
```

```
Thr Arg Ser Lys Asn Leu Tyr Lys Phe Lys Arg Val Ile Val Ile Asp
        355                 360                 365

Leu Arg Ile Val Asp Ile Tyr Glu His Ser Lys Gln Pro Gly Lys Ala
    370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
                405                 410                 415

Arg Thr Arg Ile Trp Glu Asn Lys Asn Asp Tyr Ile Gly Gly Val Leu
                420                 425                 430

Glu Ser Glu Cys Asn Gly Trp Leu Ala Ala Glu Gly Arg Thr Asp Tyr
        435                 440                 445

Val Lys Leu Phe Leu Pro Ile Ala Ile Lys Met Arg Arg Asp Lys Asp
    450                 455                 460

Val Ala Asn Thr Phe Ala Asp Ile Trp Gly Asp Phe His Glu Val Thr
465                 470                 475                 480

Gly Leu

<210> SEQ ID NO 24
<211> LENGTH: 482
<212> TYPE: PRT
<213> ORGANISM: Artificial sequence
<220> FEATURE:
<223> OTHER INFORMATION: Mutant ligase (Enterobacteria phage CC31
      backbone) protein sequence

<400> SEQUENCE: 24

Met Ile Leu Asp Ile Ile Asn Glu Ile Ala Ser Ile Gly Ser Thr Lys
1               5                   10                  15

Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
        35                  40                  45

Lys Trp Asp Thr Arg Pro Lys Gly Asp Ile His Leu Thr Leu Glu Asp
    50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Glu Lys Gly Ile Glu
    130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
        195                 200                 205

Val Met Ile Asp Gly Glu Leu Val Tyr His Ala Ser Thr Leu Pro Ala
    210                 215                 220
```

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
            245                 250                 255

Lys Ser Leu Lys Gly Thr Ile Ser Ala Lys Glu Ala Ala Gly Met Lys
        260                 265                 270

Phe Gln Val Trp Asp Tyr Val Pro Leu Asp Val Val Tyr Ser Glu Gly
    275                 280                 285

Lys Gln Ser Gly Phe Ala Tyr Asp Val Arg Phe Arg Ala Leu Glu Leu
290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
            325                 330                 335

Gly Leu Glu Gly Ile Ile Leu Lys Asn Ile Gly Ala Phe Trp Glu Asn
        340                 345                 350

Thr Arg Ser Lys Asn Leu Tyr Lys Phe Lys Val Ile Lys Ile Asp
    355                 360                 365

Leu Arg Ile Val Asp Ile Tyr Glu His Ser Lys Gln Pro Gly Lys Ala
370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
            405                 410                 415

Arg Thr Arg Ile Trp Glu Asn Lys Asn Asp Tyr Ile Gly Gly Val Leu
        420                 425                 430

Glu Ser Glu Cys Asn Gly Trp Leu Ala Ala Glu Gly Arg Thr Asp Tyr
    435                 440                 445

Val Lys Leu Phe Leu Pro Ile Ala Ile Lys Met Arg Arg Asp Lys Asp
450                 455                 460

Val Ala Asn Thr Phe Ala Asp Ile Trp Gly Asp Phe His Glu Val Thr
465                 470                 475                 480

Gly Leu

<210> SEQ ID NO 25
<211> LENGTH: 482
<212> TYPE: PRT
<213> ORGANISM: Artificial sequence
<220> FEATURE:
<223> OTHER INFORMATION: Mutant ligase (Enterobacteria phage CC31
      backbone) protein sequence

<400> SEQUENCE: 25

Met Ile Leu Asp Ile Ile Asn Glu Ile Ala Ser Ile Gly Ser Thr Lys
1               5                   10                  15

Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
        35                  40                  45

Lys Trp Asp Thr Arg Pro Lys Gly Asp Ile His Leu Thr Leu Glu Asp
    50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
            85                  90                  95

Ala Asp Ala Glu Val Val Lys Lys Val Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Glu Lys Gly Ile Glu
    130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
        195                 200                 205

Val Met Ile Asp Gly Glu Leu Val Tyr His Ala Ser Thr Leu Pro Ala
210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
                245                 250                 255

Lys Ser Leu Lys Gly Thr Ile Ser Ala Lys Glu Ala Ala Gly Met Lys
            260                 265                 270

Phe Gln Val Trp Asp Tyr Val Pro Leu Asp Val Val Tyr Ser Glu Gly
        275                 280                 285

Lys Gln Ser Gly Phe Ala Tyr Asp Val Arg Phe Arg Ala Leu Glu Leu
    290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
            340                 345                 350

Thr Arg Ser Lys Asn Leu Tyr Lys Phe Lys Gly Val Ile Phe Ile Asp
        355                 360                 365

Leu Arg Ile Val Asp Ile Tyr Glu His Ser Lys Gln Pro Gly Lys Ala
    370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
                405                 410                 415

Arg Thr Arg Ile Trp Glu Asn Lys Asn Asp Tyr Ile Gly Gly Val Leu
            420                 425                 430

Glu Ser Glu Cys Asn Gly Trp Leu Ala Ala Glu Gly Arg Thr Asp Tyr
        435                 440                 445

Val Lys Leu Phe Leu Pro Ile Ala Ile Lys Met Arg Arg Asp Lys Asp
    450                 455                 460

Val Ala Asn Thr Phe Ala Asp Ile Trp Gly Asp Phe His Glu Val Thr
465                 470                 475                 480

Gly Leu

<210> SEQ ID NO 26
<211> LENGTH: 482
<212> TYPE: PRT
<213> ORGANISM: Artificial sequence
<220> FEATURE:
<223> OTHER INFORMATION: Mutant ligase (Enterobacteria phage CC31 backbone) protein sequence

<400> SEQUENCE: 26

```
Met Ile Leu Asp Ile Ile Asn Glu Ile Ala Ser Ile Gly Ser Thr Lys
1               5                   10                  15

Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
        35                  40                  45

Lys Trp Asp Thr Arg Pro Lys Gly Asp Ile His Leu Thr Leu Glu Asp
    50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Glu Lys Gly Ile Glu
    130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
        195                 200                 205

Val Met Ile Asp Gly Glu Leu Val Tyr His Ala Ser Thr Leu Pro Ala
    210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
                245                 250                 255

Lys Ser Leu Lys Gly Thr Ile Ser Ala Lys Glu Ala Ala Gly Met Lys
            260                 265                 270

Phe Gln Val Trp Asp Tyr Val Pro Leu Asp Val Val Tyr Ser Glu Gly
        275                 280                 285

Lys Gln Ser Gly Phe Ala Tyr Asp Val Arg Phe Arg Ala Leu Glu Leu
    290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
            340                 345                 350

Thr Arg Ser Lys Asn Leu Tyr Lys Phe Lys Gly Val Ile Leu Ile Asp
        355                 360                 365

Leu Arg Ile Val Asp Ile Tyr Glu His Ser Lys Gln Pro Gly Lys Ala
    370                 375                 380

Gly Gly Phe Tyr Leu Glu Ser Glu Cys Gly Leu Ile Lys Val Lys Ala
```

```
                385                 390                 395                 400
    Gly Ser Gly Leu Lys Asp Lys Pro Gly Lys Asp Ala His Glu Leu Asp
                    405                 410                 415

Arg Thr Arg Ile Trp Glu Asn Lys Asn Asp Tyr Ile Gly Gly Val Leu
                420                 425                 430

Glu Ser Glu Cys Asn Gly Trp Leu Ala Ala Glu Gly Arg Thr Asp Tyr
                    435                 440                 445

Val Lys Leu Phe Leu Pro Ile Ala Ile Lys Met Arg Arg Asp Lys Asp
        450                 455                 460

Val Ala Asn Thr Phe Ala Asp Ile Trp Gly Asp Phe His Glu Val Thr
    465                 470                 475                 480

Gly Leu

<210> SEQ ID NO 27
<211> LENGTH: 482
<212> TYPE: PRT
<213> ORGANISM: Artificial sequence
<220> FEATURE:
<223> OTHER INFORMATION: Mutant ligase (Enterobacteria phage CC31
      backbone) protein sequence

<400> SEQUENCE: 27

Met Ile Leu Asp Ile Ile Asn Glu Ile Ala Ser Ile Gly Ser Thr Lys
1               5                   10                  15

Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
        35                  40                  45

Lys Trp Asp Thr Arg Pro Lys Gly Asp Ile His Leu Thr Leu Glu Asp
    50                  55                  60

Met Leu Tyr Leu Leu Glu Glu Lys Leu Ala Lys Arg Val Val Thr Gly
65              70                  75                  80

Asn Ala Ala Lys Glu Lys Leu Glu Ile Ala Leu Ser Gln Thr Ser Asp
            85                  90                  95

Ala Asp Ala Glu Val Val Lys Lys Val Leu Leu Arg Asp Leu Arg Cys
        100                 105                 110

Gly Ala Ser Arg Ser Ile Ala Asn Lys Val Trp Lys Asn Leu Ile Pro
    115                 120                 125

Glu Gln Pro Gln Met Leu Ala Ser Ser Tyr Asp Glu Lys Gly Ile Glu
130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
            165                 170                 175

Leu Ser Arg Ala Gly Asn Glu Tyr Leu Gly Leu Asp Leu Leu Lys Gln
        180                 185                 190

Gln Leu Ile Glu Met Thr Lys Glu Ala Arg Glu Arg His Pro Gly Gly
    195                 200                 205

Val Met Ile Asp Gly Glu Leu Val Tyr His Ala Ser Thr Leu Pro Ala
210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
            245                 250                 255

Lys Ser Leu Lys Gly Thr Ile Ser Ala Lys Glu Ala Ala Gly Met Lys
```

```
                260                 265                 270
Phe Gln Val Trp Asp Tyr Val Pro Leu Asp Val Tyr Ser Glu Gly
        275                 280                 285

Lys Gln Ser Gly Phe Ala Tyr Asp Val Arg Phe Arg Ala Leu Glu Leu
        290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
                340                 345                 350

Thr Arg Ser Lys Asn Leu Tyr Lys Phe Lys Arg Val Ile Phe Ile Asp
                355                 360                 365

Leu Arg Ile Val Asp Ile Tyr Glu His Ser Lys Gln Pro Gly Lys Ala
                370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
                405                 410                 415

Arg Thr Arg Ile Trp Glu Asn Lys Asn Asp Tyr Ile Gly Gly Val Leu
                420                 425                 430

Glu Ser Glu Cys Asn Gly Trp Leu Ala Ala Glu Gly Arg Thr Asp Tyr
                435                 440                 445

Val Lys Leu Phe Leu Pro Ile Ala Ile Lys Met Arg Arg Asp Lys Asp
                450                 455                 460

Val Ala Asn Thr Phe Ala Asp Ile Trp Gly Asp Phe His Glu Val Thr
465                 470                 475                 480

Gly Leu

<210> SEQ ID NO 28
<211> LENGTH: 497
<212> TYPE: PRT
<213> ORGANISM: Artificial sequence
<220> FEATURE:
<223> OTHER INFORMATION: Mutant ligase (Shigella phage Shf125875
      backbone) protein sequence

<400> SEQUENCE: 28

Met Ile Leu Asp Ile Leu Asn Gln Ile Ala Ala Ile Gly Ser Thr Lys
1               5                   10                  15

Thr Lys Gln Glu Ile Leu Lys Lys Asn Lys Asp Asn Lys Leu Leu Glu
                20                  25                  30

Arg Val Tyr Arg Leu Thr Tyr Ala Arg Gly Ile Gln Tyr Tyr Ile Lys
            35                  40                  45

Lys Trp Pro Gly Pro Gly Glu Arg Ser Gln Ala Tyr Gly Leu Leu Glu
        50                  55                  60

Leu Asp Asp Met Leu Asp Phe Ile Glu Phe Thr Leu Ala Thr Arg Lys
65                  70                  75                  80

Leu Thr Gly Asn Ala Ala Ile Lys Glu Leu Met Gly Tyr Ile Ala Asp
                85                  90                  95

Gly Lys Pro Asp Asp Val Glu Val Leu Arg Arg Val Met Met Arg Asp
                100                 105                 110

Leu Glu Val Gly Ala Ser Val Ser Ile Ala Asn Lys Val Trp Pro Gly
            115                 120                 125

Leu Ile Gln Leu Gln Pro Gln Met Leu Ala Ser Ala Tyr Asp Glu Lys
```

```
                130              135              140
Leu Ile Thr Lys Asn Ile Lys Trp Pro Ala Phe Ala Gln Leu Lys Ala
145                 150                 155                 160

Asp Gly Ala Arg Cys Phe Ala Glu Val Arg Asp Asp Gly Val Gln Phe
                165                 170                 175

Phe Ser Arg Ala Gly Asn Glu Tyr His Gly Leu Thr Leu Leu Ala Asp
            180                 185                 190

Glu Leu Met Glu Met Thr Lys Glu Ala Arg Glu Arg His Pro Asn Gly
        195                 200                 205

Val Leu Ile Asp Gly Glu Leu Val Tyr His Ser Phe Asp Ile Lys Lys
    210                 215                 220

Ala Val Ser Ser Gly Asn Asp Leu Ser Phe Leu Phe Gly Asp Asn Glu
225                 230                 235                 240

Glu Ser Glu Glu Val Gln Val Ala Asp Arg Ser Thr Ser Asn Gly Leu
                245                 250                 255

Ala Asn Lys Ser Leu Gln Gly Thr Ile Ser Pro Lys Glu Ala Glu Gly
            260                 265                 270

Met Val Leu Gln Ala Trp Asp Tyr Val Pro Leu Asp Glu Val Tyr Ser
        275                 280                 285

Asp Gly Lys Ile Lys Gly Gln Lys Tyr Asp Val Arg Phe Ala Ala Leu
    290                 295                 300

Glu Asn Met Ala Glu Gly Phe Lys Arg Ile Glu Pro Ile Glu Asn Gln
305                 310                 315                 320

Leu Val His Asn Leu Asp Glu Ala Lys Val Val Tyr Lys Lys Tyr Val
                325                 330                 335

Asp Gln Gly Leu Glu Gly Ile Ile Leu Lys Asn Arg Asp Ser Tyr Trp
            340                 345                 350

Glu Asn Lys Arg Ser Lys Asn Leu Ile Lys Phe Lys Arg Val Ile Val
        355                 360                 365

Ile Ala Leu Glu Val Val Gly Tyr Tyr Glu His Ser Lys Asp Pro Asn
    370                 375                 380

Lys Leu Gly Gly Val Glu Leu Val Ser Arg Cys Arg Arg Ile Thr Thr
385                 390                 395                 400

Asp Cys Gly Ser Gly Phe Lys Asp Thr Thr His Lys Thr Val Asp Gly
                405                 410                 415

Val Lys Val Leu Ile Pro Leu Asp Glu Arg His Asp Leu Asp Arg Glu
            420                 425                 430

Arg Leu Met Ala Glu Ala Arg Glu Gly Lys Leu Ile Gly Arg Ile Ala
        435                 440                 445

Asp Cys Glu Cys Asn Gly Trp Val His Ser Lys Gly Arg Glu Gly Thr
    450                 455                 460

Val Gly Ile Phe Leu Pro Ile Ile Lys Gly Phe Arg Phe Asp Lys Thr
465                 470                 475                 480

Glu Ala Asp Ser Phe Glu Asp Val Phe Gly Pro Trp Ser Gln Thr Gly
                485                 490                 495

Leu

<210> SEQ ID NO 29
<211> LENGTH: 298
<212> TYPE: PRT
<213> ORGANISM: Paramecium bursaria Chlorella virus PBCV-1

<400> SEQUENCE: 29

Met Ala Ile Thr Lys Pro Leu Leu Ala Ala Thr Leu Glu Asn Ile Glu
```

```
            1               5                   10                  15
Asp Val Gln Phe Pro Cys Leu Ala Thr Pro Lys Ile Asp Gly Ile Arg
                20                  25                  30
Ser Val Lys Gln Thr Gln Met Leu Ser Arg Thr Phe Lys Pro Ile Arg
                35                  40                  45
Asn Ser Val Met Asn Arg Leu Leu Thr Glu Leu Leu Pro Glu Gly Ser
                50                  55                  60
Asp Gly Glu Ile Ser Ile Glu Gly Ala Thr Phe Gln Asp Thr Thr Ser
65                  70                  75                  80
Ala Val Met Thr Gly His Lys Met Tyr Asn Ala Lys Phe Ser Tyr Tyr
                85                  90                  95
Trp Phe Asp Tyr Val Thr Asp Pro Leu Lys Lys Tyr Ile Asp Arg
                100                 105                 110
Val Glu Asp Met Lys Asn Tyr Ile Thr Val His Pro His Ile Leu Glu
                115                 120                 125
His Ala Gln Val Lys Ile Ile Pro Leu Ile Pro Val Glu Ile Asn Asn
                130                 135                 140
Ile Thr Glu Leu Leu Gln Tyr Glu Arg Asp Val Leu Ser Lys Gly Phe
145                 150                 155                 160
Glu Gly Val Met Ile Arg Lys Pro Asp Gly Lys Tyr Lys Phe Gly Arg
                165                 170                 175
Ser Thr Leu Lys Glu Gly Ile Leu Leu Lys Met Lys Gln Phe Lys Asp
                180                 185                 190
Ala Glu Ala Thr Ile Ile Ser Met Thr Ala Leu Phe Lys Asn Thr Asn
                195                 200                 205
Thr Lys Thr Lys Asp Asn Phe Gly Tyr Ser Lys Arg Ser Thr His Lys
                210                 215                 220
Ser Gly Lys Val Glu Glu Asp Val Met Gly Ser Ile Glu Val Asp Tyr
225                 230                 235                 240
Asp Gly Val Val Phe Ser Ile Gly Thr Gly Phe Asp Ala Asp Gln Arg
                245                 250                 255
Arg Asp Phe Trp Gln Asn Lys Glu Ser Tyr Ile Gly Lys Met Val Lys
                260                 265                 270
Phe Lys Tyr Phe Glu Met Gly Ser Lys Asp Cys Pro Arg Phe Pro Val
                275                 280                 285
Phe Ile Gly Ile Arg His Glu Glu Asp Arg
                290                 295

<210> SEQ ID NO 30
<211> LENGTH: 23
<212> TYPE: DNA
<213> ORGANISM: Artificial sequence
<220> FEATURE:
<223> OTHER INFORMATION: Example 5, 8 and 9 template oligonucleotide
      sequence

<400> SEQUENCE: 30
tttggtgcga agcagactga ggc                                            23

<210> SEQ ID NO 31
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 31
```
tttggtgcga agcagagtga ggc                                            23

<210> SEQ ID NO 32
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 32
tttggtgcga agcagattga ggc                                            23

<210> SEQ ID NO 33
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 33
tttggtgcga agcagaatga ggc                                            23

<210> SEQ ID NO 34
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 34
tttggtgcga agcagtctga ggc                                            23

<210> SEQ ID NO 35
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 35
tttggtgcga agcagtgtga ggc                                            23

<210> SEQ ID NO 36
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 36
tttggtgcga agcagtttga ggc                                            23

<210> SEQ ID NO 37
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 37
tttggtgcga agcagtatga ggc                                            23

<210> SEQ ID NO 38
<211> LENGTH: 23
<212> TYPE: DNA
<213> ORGANISM: Artificial sequence

```
<220> FEATURE:
<223> OTHER INFORMATION: Example 5 template oligonucleotide sequence

<400> SEQUENCE: 38
tttggtgcga agcagcctga ggc                                             23

<210> SEQ ID NO 39
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 39
tttggtgcga agcagcgtga ggc                                             23

<210> SEQ ID NO 40
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 40
tttggtgcga agcagcttga ggc                                             23

<210> SEQ ID NO 41
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 41
tttggtgcga agcagcatga ggc                                             23

<210> SEQ ID NO 42
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 42
tttggtgcga agcaggctga ggc                                             23

<210> SEQ ID NO 43
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 43
tttggtgcga agcagggtga ggc                                             23

<210> SEQ ID NO 44
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 44
tttggtgcga agcaggttga ggc                                             23
```

<210> SEQ ID NO 45
<211> LENGTH: 23
<212> TYPE: DNA
<213> ORGANISM: Artificial sequence
<220> FEATURE:
<223> OTHER INFORMATION: Example 5 template oligonucleotide sequence

<400> SEQUENCE: 45
tttggtgcga agcaggatga ggc                                             23

<210> SEQ ID NO 46
<211> LENGTH: 20
<212> TYPE: DNA
<213> ORGANISM: Artificial sequence
<220> FEATURE:
<223> OTHER INFORMATION: Example 14 "20 mer" oligonucleotide sequence

<400> SEQUENCE: 46
gccucagtct gcttcgcacc                                                 20

<210> SEQ ID NO 47
<211> LENGTH: 36
<212> TYPE: DNA
<213> ORGANISM: Artificial sequence
<220> FEATURE:
<223> OTHER INFORMATION: Example 7 template oligonucleotide sequence

<400> SEQUENCE: 47
tttggtgcga agcagaaggt aagccgaggt ttggcc                               36

<210> SEQ ID NO 48
<211> LENGTH: 298
<212> TYPE: PRT
<213> ORGANISM: Paramecium bursaria Chlorella virus NE-JV-4

<400> SEQUENCE: 48

Met Ala Ile Thr Lys Pro Leu Leu Ala Ala Thr Leu Glu Asn Ile Glu
1               5                   10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45

Asn Ser Val Met Asn Arg Leu Leu Thr Glu Leu Leu Pro Glu Gly Ser
    50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
                85                  90                  95

Trp Phe Asp Tyr Val Thr Asp Asp Pro Leu Lys Lys Tyr Ser Asp Arg
            100                 105                 110

Val Glu Asp Met Lys Asn Tyr Ile Thr Ala His Pro His Ile Leu Asp
        115                 120                 125

His Glu Gln Val Lys Ile Ile Pro Leu Ile Pro Val Glu Ile Asn Asn
    130                 135                 140

Ile Thr Glu Leu Leu Gln Tyr Glu Arg Asp Val Leu Ser Lys Gly Phe
145                 150                 155                 160

Glu Gly Val Met Ile Arg Lys Pro Asp Gly Lys Tyr Lys Phe Gly Arg
                165                 170                 175

Ser Thr Leu Lys Glu Gly Ile Leu Leu Lys Met Lys Gln Phe Lys Asp
            180                 185                 190

```
Ala Glu Ala Thr Ile Ile Ser Met Thr Ala Leu Phe Lys Asn Thr Asn
            195                 200                 205

Thr Lys Thr Lys Asp Asn Phe Gly Tyr Ser Lys Arg Ser Thr His Lys
    210                 215                 220

Asn Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
                260                 265                 270

Phe Lys Tyr Phe Glu Met Gly Ser Lys Asp Cys Pro Arg Phe Pro Val
            275                 280                 285

Phe Ile Gly Ile Arg His Glu Glu Asp His
            290                 295
```

<210> SEQ ID NO 49
<211> LENGTH: 298
<212> TYPE: PRT
<213> ORGANISM: Paramecium bursaria Chlorella virus NYs1

<400> SEQUENCE: 49

```
Met Thr Ile Ala Lys Pro Leu Leu Ala Ala Thr Leu Glu Asn Leu Asp
1               5                   10                  15

Asp Val Lys Phe Pro Cys Leu Val Thr Pro Lys Ile Asp Gly Ile Arg
                20                  25                  30

Ser Leu Lys Gln Gln His Met Leu Ser Arg Thr Phe Lys Pro Ile Arg
            35                  40                  45

Asn Ser Val Met Asn Lys Leu Leu Ser Glu Leu Leu Pro Glu Gly Ala
        50                  55                  60

Asp Gly Glu Ile Cys Ile Glu Asp Ser Thr Phe Gln Ala Thr Thr Ser
65                  70                  75                  80

Ala Val Met Thr Gly His Lys Val Tyr Asp Glu Lys Phe Ser Tyr Tyr
                85                  90                  95

Trp Phe Asp Tyr Val Val Asp Asp Pro Leu Lys Ser Tyr Thr Asp Arg
                100                 105                 110

Val Asn Asp Met Lys Lys Tyr Val Asp Asp His Pro His Ile Leu Glu
            115                 120                 125

His Glu Gln Val Lys Ile Ile Pro Leu Ile Pro Val Glu Ile Asn Asn
        130                 135                 140

Ile Asp Glu Leu Ser Gln Tyr Glu Arg Asp Val Leu Ala Lys Gly Phe
145                 150                 155                 160

Glu Gly Val Met Ile Arg Arg Pro Asp Gly Lys Tyr Lys Phe Gly Arg
                165                 170                 175

Ser Thr Leu Lys Glu Gly Ile Leu Leu Lys Met Lys Gln Phe Lys Asp
            180                 185                 190

Ala Glu Ala Thr Ile Ile Ser Met Ser Pro Arg Leu Lys Asn Thr Asn
            195                 200                 205

Ala Lys Ser Lys Asp Asn Leu Gly Tyr Ser Lys Arg Ser Thr His Lys
    210                 215                 220

Ser Gly Lys Val Glu Glu Thr Met Gly Ser Ile Glu Val Asp Tyr
225                 230                 235                 240

Asp Gly Val Val Phe Ser Ile Gly Thr Gly Phe Asp Asp Glu Gln Arg
                245                 250                 255

Lys His Phe Trp Glu Asn Lys Asp Ser Tyr Ile Gly Lys Leu Leu Lys
```

```
                    260                 265                 270
Phe Lys Tyr Phe Glu Met Gly Ser Lys Asp Ala Pro Arg Phe Pro Val
            275                 280                 285

Phe Ile Gly Ile Arg His Glu Glu Asp Cys
            290                 295

<210> SEQ ID NO 50
<211> LENGTH: 301
<212> TYPE: PRT
<213> ORGANISM: Paramecium bursaria Chlorella virus NE-JV-1

<400> SEQUENCE: 50

Met Thr Ala Ile Gln Lys Pro Leu Leu Ala Ala Ser Phe Lys Lys Leu
1               5                   10                  15

Thr Val Ala Asp Val Lys Tyr Pro Val Phe Ala Thr Pro Lys Leu Asp
            20                  25                  30

Gly Ile Arg Ala Leu Lys Ile Asp Gly Ala Phe Val Ser Arg Thr Phe
        35                  40                  45

Lys Pro Ile Arg Asn Arg Ala Ile Ala Asp Ala Leu Gln Asp Leu Leu
    50                  55                  60

Pro Asn Gly Ser Asp Gly Glu Ile Leu Ser Gly Ser Thr Phe Gln Asp
65                  70                  75                  80

Ala Ser Ser Ala Val Met Thr Ala Lys Ala Gly Ile Gly Ala Asn Thr
                85                  90                  95

Ile Phe Tyr Trp Phe Asp Tyr Val Lys Asp Pro Asn Lys Pro Tyr
            100                 105                 110

Leu Asp Arg Met Thr Asp Met Glu Asn Tyr Leu Lys Glu Arg Pro Glu
            115                 120                 125

Ile Leu Asn Asp Asp Arg Ile Lys Ile Val Pro Leu Ile Pro Lys Lys
130                 135                 140

Ile Glu Thr Lys Asp Glu Leu Asp Thr Phe Glu Lys Ile Cys Leu Asp
145                 150                 155                 160

Gln Gly Phe Glu Gly Val Met Ile Arg Ser Gly Ala Gly Lys Tyr Lys
                165                 170                 175

Phe Gly Arg Ser Thr Glu Lys Glu Gly Ile Leu Ile Lys Ile Lys Gln
            180                 185                 190

Phe Glu Asp Asp Glu Ala Val Val Ile Gly Phe Thr Pro Met Gln Thr
            195                 200                 205

Asn Thr Asn Asp Lys Ser Met Asn Glu Leu Gly Asp Met Lys Arg Ser
210                 215                 220

Ser His Lys Asp Gly Lys Val Asn Leu Asp Thr Leu Gly Ala Leu Glu
225                 230                 235                 240

Val Asp Trp Asn Gly Ile Thr Phe Ser Ile Gly Thr Gly Phe Asp His
                245                 250                 255

Ala Leu Arg Asp Lys Leu Trp Ser Glu Arg Asp Lys Leu Ile Gly Lys
            260                 265                 270

Ile Val Lys Phe Lys Tyr Phe Ala Gln Gly Val Lys Thr Ala Pro Arg
            275                 280                 285

Phe Pro Val Phe Ile Gly Phe Arg Asp Pro Asp Met
            290                 295                 300

<210> SEQ ID NO 51
<211> LENGTH: 300
<212> TYPE: PRT
<213> ORGANISM: Acanthocystis turfacea Chlorella virus Canal-1
```

<400> SEQUENCE: 51

Met Ala Ile Gln Lys Pro Leu Leu Ala Ala Ser Leu Lys Lys Met Ser
1               5                   10                  15

Val Gly Asp Leu Thr Phe Pro Val Phe Ala Thr Pro Lys Leu Asp Gly
            20                  25                  30

Ile Arg Ala Leu Lys Val Gly Thr Ile Val Ser Arg Thr Phe Lys
            35                  40                  45

Pro Val Arg Asn Ser Ala Ile Ser Glu Val Leu Ala Ser Ile Leu Pro
        50                  55                  60

Asp Gly Ser Asp Gly Glu Ile Leu Ser Gly Lys Thr Phe Gln Glu Ser
65                  70                  75                  80

Thr Ser Thr Val Met Thr Ala Asp Ala Gly Leu Gly Ser Gly Thr Met
            85                  90                  95

Phe Phe Trp Phe Asp Tyr Val Lys Asp Pro Asn Lys Gly Tyr Leu
            100                 105                 110

Asp Arg Ile Ala Asp Met Lys Ser Phe Thr Asp Arg His Pro Glu Ile
        115                 120                 125

Leu Lys Asp Lys Arg Val Thr Ile Val Pro Leu Phe Pro Lys Lys Ile
    130                 135                 140

Asp Thr Thr Glu Glu Leu His Glu Phe Glu Lys Trp Cys Leu Asp Gln
145                 150                 155                 160

Gly Phe Glu Gly Val Met Val Arg Asn Ala Gly Gly Lys Tyr Lys Phe
            165                 170                 175

Gly Arg Ser Thr Glu Lys Glu Gln Ile Leu Val Lys Ile Lys Gln Phe
            180                 185                 190

Glu Asp Asp Glu Ala Val Val Ile Gly Val Ser Ala Leu Gln Thr Asn
        195                 200                 205

Thr Asn Asp Lys Lys Leu Asn Gln Leu Gly Glu Met Arg Arg Thr Ser
210                 215                 220

His Gln Asp Gly Lys Val Glu Leu Glu Met Leu Gly Ala Leu Asp Val
225                 230                 235                 240

Asp Trp Asn Gly Ile Arg Phe Ser Ile Gly Thr Gly Phe Asp Arg Asp
            245                 250                 255

Thr Arg Val Asp Leu Trp Lys Arg Arg Glu Gly Val Ile Gly Lys Ile
            260                 265                 270

Val Lys Phe Lys Tyr Phe Ser Gln Gly Ile Lys Thr Ala Pro Arg Phe
    275                 280                 285

Pro Val Phe Leu Gly Phe Arg Asp Lys Asp Met
    290                 295                 300

<210> SEQ ID NO 52
<211> LENGTH: 300
<212> TYPE: PRT
<213> ORGANISM: Acanthocystis turfacea Chlorella virus Br0604L

<400> SEQUENCE: 52

Met Ala Ile Gln Lys Pro Leu Leu Ala Ala Ser Leu Lys Lys Leu Ser
1               5                   10                  15

Val Asp Asp Leu Thr Phe Pro Val Tyr Ala Thr Pro Lys Leu Asp Gly
            20                  25                  30

Ile Arg Ala Leu Lys Ile Asp Gly Thr Leu Val Ser Arg Thr Phe Lys
            35                  40                  45

Pro Ile Arg Asn Thr Thr Ile Ser Lys Val Leu Thr Ser Leu Leu Pro
        50                  55                  60

Asp Gly Ser Asp Gly Glu Ile Leu Ser Gly Lys Thr Phe Gln Asp Ser
65                  70                  75                  80

Thr Ser Thr Val Met Ser Ala Asp Ala Gly Ile Gly Ser Gly Thr Thr
            85                  90                  95

Phe Phe Trp Phe Asp Tyr Val Lys Asp Pro Asn Lys Gly Tyr Leu
        100                 105                 110

Asp Arg Ile Ala Asp Ile Lys Lys Phe Ile Asp Cys Arg Pro Glu Ile
            115                 120                 125

Leu Lys Asp Ser Arg Val Ile Val Pro Leu Phe Pro Lys Lys Ile
    130                 135                 140

Asp Thr Ala Glu Glu Leu Asn Val Phe Glu Lys Trp Cys Leu Asp Gln
145                 150                 155                 160

Gly Phe Glu Gly Val Met Val Arg Asn Ala Gly Lys Tyr Lys Phe
                165                 170                 175

Gly Arg Ser Thr Glu Lys Glu Gln Ile Leu Val Lys Ile Lys Gln Phe
                180                 185                 190

Glu Asp Asp Glu Ala Val Val Ile Gly Val Ser Ala Leu Gln Thr Asn
                195                 200                 205

Thr Asn Asp Lys Lys Val Asn Glu Leu Gly Glu Met Arg Arg Thr Ser
210                 215                 220

His Gln Asp Gly Lys Val Asp Leu Asp Met Leu Gly Ala Leu Asp Val
225                 230                 235                 240

Asp Trp Asn Gly Ile Arg Phe Gly Ile Gly Thr Gly Phe Asp Lys Asp
                245                 250                 255

Thr Arg Glu Asp Leu Trp Lys Arg Arg Asp Ser Ile Ile Gly Lys Ile
            260                 265                 270

Val Lys Phe Lys Tyr Phe Ser Gln Gly Val Lys Thr Ala Pro Arg Phe
    275                 280                 285

Pro Val Phe Leu Gly Phe Arg Asp Lys Asn Asp Met
    290                 295                 300

<210> SEQ ID NO 53
<211> LENGTH: 300
<212> TYPE: PRT
<213> ORGANISM: Acanthocystis turfacea Chlorella virus NE-JV-2

<400> SEQUENCE: 53

Met Ala Ile Gln Lys Pro Leu Leu Ala Ala Ser Leu Lys Lys Leu Ser
1               5                   10                  15

Val Asp Asp Leu Thr Phe Pro Val Tyr Ala Thr Pro Lys Leu Asp Gly
            20                  25                  30

Ile Arg Ala Leu Lys Ile Asp Gly Thr Ile Val Ser Arg Thr Phe Lys
        35                  40                  45

Pro Ile Arg Asn Thr Thr Ile Ser Asn Val Leu Met Ser Leu Leu Pro
    50                  55                  60

Asp Gly Ser Asp Gly Glu Ile Leu Ser Gly Lys Thr Phe Gln Asp Ser
65                  70                  75                  80

Thr Ser Thr Val Met Ser Ala Asp Ala Gly Ile Gly Ser Gly Thr Thr
            85                  90                  95

Phe Phe Trp Phe Asp Tyr Val Lys Asp Pro Asp Lys Gly Tyr Leu
        100                 105                 110

Asp Arg Ile Ala Asp Met Lys Lys Phe Val Asp Ser His Pro Glu Ile
            115                 120                 125

Leu Lys Asp Arg Arg Val Thr Ile Val Pro Leu Ile Pro Lys Lys Ile
    130                 135                 140

Asp Thr Val Glu Glu Leu Asn Val Phe Glu Gln Trp Cys Leu Asp Gln
145                 150                 155                 160

Gly Phe Glu Gly Val Met Val Arg Asn Ala Gly Gly Lys Tyr Lys Phe
                165                 170                 175

Gly Arg Ser Thr Glu Lys Glu Gln Ile Leu Val Lys Ile Lys Gln Phe
            180                 185                 190

Glu Asp Asp Glu Ala Val Val Ile Gly Val Ser Ala Leu Gln Thr Asn
        195                 200                 205

Val Asn Asp Lys Lys Met Asn Glu Leu Gly Asp Met Arg Arg Thr Ser
    210                 215                 220

His Lys Asp Gly Lys Ile Asp Leu Glu Met Leu Gly Ala Leu Asp Val
225                 230                 235                 240

Glu Trp Asn Gly Ile Arg Phe Gly Ile Gly Thr Gly Phe Asp Lys Asp
                245                 250                 255

Thr Arg Glu Asp Leu Trp Lys Lys Arg Asp Ser Ile Ile Gly Lys Val
            260                 265                 270

Val Lys Phe Lys Tyr Phe Ser Gln Gly Ile Lys Thr Ala Pro Arg Phe
        275                 280                 285

Pro Val Phe Leu Gly Phe Arg Asp Glu Asn Asp Met
    290                 295                 300

<210> SEQ ID NO 54
<211> LENGTH: 300
<212> TYPE: PRT
<213> ORGANISM: Acanthocystis turfacea Chlorella virus TN603.4.2

<400> SEQUENCE: 54

Met Ala Ile Gln Lys Pro Leu Leu Ala Ala Ser Leu Lys Lys Met Ser
1               5                   10                  15

Val Asp Asn Leu Thr Phe Pro Val Tyr Ala Thr Pro Lys Leu Asp Gly
            20                  25                  30

Ile Arg Ala Leu Lys Ile Asp Gly Thr Leu Val Ser Arg Thr Phe Lys
        35                  40                  45

Pro Ile Arg Asn Thr Thr Ile Ser Lys Val Leu Ala Ser Leu Leu Pro
50                  55                  60

Asp Gly Ser Asp Gly Glu Ile Leu Ser Gly Lys Thr Phe Gln Asp Ser
65                  70                  75                  80

Thr Ser Thr Val Met Thr Thr Asp Ala Gly Ile Gly Ser Asp Thr Thr
                85                  90                  95

Phe Phe Trp Phe Asp Tyr Val Lys Asp Pro Asp Lys Gly Tyr Leu
            100                 105                 110

Asp Arg Ile Ala Asp Met Lys Thr Phe Val Asp Gln His Pro Glu Ile
        115                 120                 125

Leu Lys Asp Ser Cys Val Thr Ile Val Pro Leu Phe Pro Lys Lys Ile
    130                 135                 140

Asp Thr Pro Glu Glu Leu His Val Phe Glu Lys Trp Cys Leu Asp Gln
145                 150                 155                 160

Gly Phe Glu Gly Val Met Val Arg Thr Ala Gly Gly Lys Tyr Lys Phe
                165                 170                 175

Gly Arg Ser Thr Glu Lys Glu Gln Ile Leu Val Lys Ile Lys Gln Phe
            180                 185                 190

Glu Asp Asp Glu Ala Val Val Ile Gly Val Ser Ala Leu Gln Thr Asn
        195                 200                 205

Thr Asn Asp Lys Lys Leu Asn Gln Leu Gly Glu Met Arg Arg Thr Ser

```
                210                 215                 220
His Gln Asp Gly Lys Val Asp Leu Asp Met Leu Gly Ala Leu Asp Val
225                 230                 235                 240

Asp Trp Asn Gly Ile Arg Phe Ser Ile Gly Thr Gly Phe Asp Lys Asp
                245                 250                 255

Thr Arg Glu Asp Leu Trp Lys Gln Arg Asp Ser Ile Val Gly Lys Val
                260                 265                 270

Val Lys Phe Lys Tyr Phe Ser Gln Gly Ile Lys Thr Ala Pro Arg Phe
                275                 280                 285

Pro Val Phe Leu Gly Phe Arg Asp Glu Asn Asp Met
                290                 295                 300

<210> SEQ ID NO 55
<211> LENGTH: 300
<212> TYPE: PRT
<213> ORGANISM: Acanthocystis turfacea Chlorella virus GM0701.1

<400> SEQUENCE: 55

Met Ala Ile Gln Lys Pro Leu Leu Ala Ser Leu Lys Lys Met Ser
1               5                   10                  15

Val Asp Asp Leu Thr Phe Pro Val Tyr Thr Thr Pro Lys Leu Asp Gly
                20                  25                  30

Ile Arg Ala Leu Lys Ile Asp Gly Thr Leu Val Ser Arg Thr Phe Lys
                35                  40                  45

Pro Val Arg Asn Ser Ala Ile Ser Glu Val Leu Ala Ser Leu Leu Pro
                50                  55                  60

Asp Gly Ser Asp Gly Glu Ile Leu Ser Gly Lys Thr Phe Gln Asp Ser
65                  70                  75                  80

Thr Ser Thr Val Met Thr Thr Asp Ala Gly Ile Gly Ser Asp Thr Thr
                85                  90                  95

Phe Phe Trp Phe Asp Tyr Val Lys Asp Pro Asn Lys Gly Tyr Leu
                100                 105                 110

Asp Arg Ile Ala Asp Met Lys Thr Phe Ile Asp Gln His Pro Glu Met
                115                 120                 125

Leu Lys Asp Asn His Val Thr Ile Val Pro Leu Ile Pro Lys Lys Ile
                130                 135                 140

Asp Thr Val Glu Glu Leu Asn Ile Phe Glu Lys Trp Cys Leu Asp Gln
145                 150                 155                 160

Gly Phe Glu Gly Val Met Val Arg Asn Ala Gly Lys Tyr Lys Phe
                165                 170                 175

Gly Arg Ser Thr Glu Lys Glu Gln Ile Leu Val Lys Ile Lys Gln Phe
                180                 185                 190

Glu Asp Asp Glu Ala Val Val Ile Gly Val Ser Ala Leu Gln Thr Asn
                195                 200                 205

Thr Asn Asp Lys Lys Leu Asn Gln Leu Gly Glu Met Arg Arg Thr Ser
210                 215                 220

His Gln Asp Gly Lys Ile Asp Leu Glu Met Leu Gly Ala Leu Asp Val
225                 230                 235                 240

Asp Trp Asn Gly Ile Arg Phe Ser Ile Gly Thr Gly Phe Asp Arg Asp
                245                 250                 255

Thr Arg Val Asp Leu Trp Lys Arg Arg Asp Gly Ile Val Gly Arg Thr
                260                 265                 270

Ile Lys Phe Lys Tyr Phe Gly Gln Gly Ile Lys Thr Ala Pro Arg Phe
                275                 280                 285
```

```
Pro Val Phe Leu Gly Phe Arg Asp Lys Asp Asp Met
    290                 295                 300
```

<210> SEQ ID NO 56
<211> LENGTH: 287
<212> TYPE: PRT
<213> ORGANISM: Synechococcus phage S-CRM01

<400> SEQUENCE: 56

```
Met Leu Ala Gly Asn Phe Asp Pro Lys Lys Ala Lys Phe Pro Tyr Cys
1               5                   10                  15

Ala Thr Pro Lys Ile Asp Gly Ile Arg Phe Leu Met Val Asn Gly Arg
            20                  25                  30

Ala Leu Ser Arg Thr Phe Lys Pro Ile Arg Asn Glu Tyr Ile Gln Lys
        35                  40                  45

Leu Leu Ser Lys His Leu Pro Asp Gly Ile Asp Gly Glu Leu Thr Cys
    50                  55                  60

Gly Asp Thr Phe Gln Ser Ser Thr Ser Ala Ile Met Arg Ile Ala Gly
65                  70                  75                  80

Glu Pro Asp Phe Lys Ala Trp Ile Phe Asp Tyr Val Asp Pro Asp Ser
                85                  90                  95

Thr Ser Ile Leu Pro Phe Ile Glu Arg Phe Asp Gln Ile Ser Asp Ile
            100                 105                 110

Ile Tyr Asn Gly Pro Ile Pro Phe Lys His Gln Val Leu Gly Gln Ser
        115                 120                 125

Ile Leu Tyr Asn Ile Asp Asp Leu Asn Arg Tyr Glu Glu Ala Cys Leu
    130                 135                 140

Asn Glu Gly Tyr Glu Gly Val Met Leu Arg Asp Pro Tyr Gly Thr Tyr
145                 150                 155                 160

Lys Phe Gly Arg Ser Ser Thr Asn Glu Gly Ile Leu Leu Lys Val Lys
                165                 170                 175

Arg Phe Glu Asp Ala Glu Ala Thr Val Ile Arg Ile Asp Glu Lys Met
            180                 185                 190

Ser Asn Gln Asn Ile Ala Glu Lys Asp Asn Phe Gly Arg Thr Lys Arg
        195                 200                 205

Ser Ser Cys Leu Asp Gly Met Val Pro Met Glu Thr Thr Gly Ala Leu
    210                 215                 220

Phe Val Arg Asn Ser Asp Gly Leu Glu Phe Ser Ile Gly Ser Gly Leu
225                 230                 235                 240

Asn Asp Glu Met Arg Asp Glu Ile Trp Lys Asn Lys Ser Ser Tyr Ile
                245                 250                 255

Gly Lys Leu Val Lys Tyr Lys Tyr Phe Pro Gln Gly Val Lys Asp Leu
            260                 265                 270

Pro Arg His Pro Val Phe Leu Gly Phe Arg Asp Pro Asp Asp Met
        275                 280                 285
```

<210> SEQ ID NO 57
<211> LENGTH: 322
<212> TYPE: PRT
<213> ORGANISM: marine sediment metagenome

<400> SEQUENCE: 57

```
Met Asp Ala His Glu Leu Met Lys Leu Asn Glu Tyr Ala Glu Arg Gln
1               5                   10                  15

Asn Gln Lys Gln Lys Lys Gln Ile Thr Lys Pro Met Leu Ala Ala Ser
            20                  25                  30
```

```
Leu Lys Asp Ile Thr Gln Leu Asp Tyr Ser Lys Gly Tyr Leu Ala Thr
             35                  40                  45

Gln Lys Leu Asp Gly Ile Arg Ala Leu Met Ile Asp Gly Lys Leu Val
 50                  55                  60

Ser Arg Thr Phe Lys Pro Ile Arg Asn Asn His Ile Arg Glu Met Leu
 65                  70                  75                  80

Glu Asp Val Leu Pro Asp Gly Ala Asp Gly Glu Ile Val Cys Pro Gly
                 85                  90                  95

Ala Phe Gln Ala Thr Ser Ser Gly Val Met Ser Ala Asn Gly Glu Pro
            100                 105                 110

Glu Phe Ile Tyr Tyr Met Phe Asp Tyr Val Lys Asp Asp Ile Thr Lys
            115                 120                 125

Glu Tyr Trp Arg Arg Thr Gln Asp Met Val Gln Trp Leu Ile Asn Gln
130                 135                 140

Gly Pro Thr Arg Thr Pro Gly Leu Ser Lys Leu Lys Leu Leu Val Pro
145                 150                 155                 160

Thr Leu Ile Lys Asn Tyr Asp His Leu Lys Thr Tyr Glu Thr Glu Cys
                165                 170                 175

Ile Asp Lys Gly Phe Glu Gly Val Ile Leu Arg Thr Pro Asp Ser Pro
            180                 185                 190

Tyr Lys Cys Gly Arg Ser Thr Ala Lys Gln Glu Trp Leu Leu Lys Leu
            195                 200                 205

Lys Arg Phe Ala Asp Asp Glu Ala Val Val Ile Gly Phe Thr Glu Lys
210                 215                 220

Met His Asn Asp Asn Glu Ala Thr Lys Asp Lys Phe Gly His Thr Val
225                 230                 235                 240

Arg Ser Ser His Lys Glu Asn Lys Arg Pro Ala Gly Thr Leu Gly Ser
                245                 250                 255

Leu Ile Val Arg Asp Ile Lys Thr Glu Ile Glu Phe Glu Ile Gly Thr
            260                 265                 270

Gly Phe Asp Asp Glu Leu Arg Gln Lys Ile Trp Asp Ala Arg Pro Glu
            275                 280                 285

Trp Asp Gly Leu Cys Val Lys Tyr Lys His Phe Ala Ile Ser Gly Val
290                 295                 300

Lys Glu Lys Pro Arg Phe Pro Ser Phe Ile Gly Val Arg Asp Val Glu
305                 310                 315                 320

Asp Met

<210> SEQ ID NO 58
<211> LENGTH: 691
<212> TYPE: PRT
<213> ORGANISM: Mycobacterium tuberculosis (strain ATCC 25618/H37Rv)

<400> SEQUENCE: 58

Met Ser Ser Pro Asp Ala Asp Gln Thr Ala Pro Glu Val Leu Arg Gln
 1               5                  10                  15

Trp Gln Ala Leu Ala Glu Glu Val Arg Glu His Gln Phe Arg Tyr Tyr
             20                  25                  30

Val Arg Asp Ala Pro Ile Ile Ser Asp Ala Glu Phe Asp Glu Leu Leu
             35                  40                  45

Arg Arg Leu Glu Ala Leu Glu Glu Gln His Pro Glu Leu Arg Thr Pro
 50                  55                  60

Asp Ser Pro Thr Gln Leu Val Gly Gly Ala Gly Phe Ala Thr Asp Phe
 65                  70                  75                  80
```

```
Glu Pro Val Asp His Leu Glu Arg Met Leu Ser Leu Asp Asn Ala Phe
                 85                  90                  95

Thr Ala Asp Glu Leu Ala Ala Trp Ala Gly Arg Ile His Ala Glu Val
            100                 105                 110

Gly Asp Ala Ala His Tyr Leu Cys Glu Leu Lys Ile Asp Gly Val Ala
            115                 120                 125

Leu Ser Leu Val Tyr Arg Glu Gly Arg Leu Thr Arg Ala Ser Thr Arg
        130                 135                 140

Gly Asp Gly Arg Thr Gly Glu Asp Val Thr Leu Asn Ala Arg Thr Ile
145                 150                 155                 160

Ala Asp Val Pro Glu Arg Leu Thr Pro Gly Asp Asp Tyr Pro Val Pro
                165                 170                 175

Glu Val Leu Glu Val Arg Gly Glu Val Phe Phe Arg Leu Asp Asp Phe
            180                 185                 190

Gln Ala Leu Asn Ala Ser Leu Val Glu Gly Lys Ala Pro Phe Ala
        195                 200                 205

Asn Pro Arg Asn Ser Ala Ala Gly Ser Leu Arg Gln Lys Asp Pro Ala
    210                 215                 220

Val Thr Ala Arg Arg Leu Arg Met Ile Cys His Gly Leu Gly His
225                 230                 235                 240

Val Glu Gly Phe Arg Pro Ala Thr Leu His Gln Ala Tyr Leu Ala Leu
                245                 250                 255

Arg Ala Trp Gly Leu Pro Val Ser Glu His Thr Leu Ala Thr Asp
            260                 265                 270

Leu Ala Gly Val Arg Glu Arg Ile Asp Tyr Trp Gly Glu His Arg His
        275                 280                 285

Glu Val Asp His Glu Ile Asp Gly Val Val Lys Val Asp Glu Val
    290                 295                 300

Ala Leu Gln Arg Arg Leu Gly Ser Thr Ser Arg Ala Pro Arg Trp Ala
305                 310                 315                 320

Ile Ala Tyr Lys Tyr Pro Pro Glu Glu Ala Gln Thr Lys Leu Leu Asp
                325                 330                 335

Ile Arg Val Asn Val Gly Arg Thr Gly Arg Ile Thr Pro Phe Ala Phe
            340                 345                 350

Met Thr Pro Val Lys Val Ala Gly Ser Thr Val Gly Gln Ala Thr Leu
        355                 360                 365

His Asn Ala Ser Glu Ile Lys Arg Lys Gly Val Leu Ile Gly Asp Thr
    370                 375                 380

Val Val Ile Arg Lys Ala Gly Asp Val Ile Pro Glu Val Leu Gly Pro
385                 390                 395                 400

Val Val Glu Leu Arg Asp Gly Ser Glu Arg Glu Phe Ile Met Pro Thr
                405                 410                 415

Thr Cys Pro Glu Cys Gly Ser Pro Leu Ala Pro Glu Lys Glu Gly Asp
            420                 425                 430

Ala Asp Ile Arg Cys Pro Asn Ala Arg Gly Cys Pro Gly Gln Leu Arg
        435                 440                 445

Glu Arg Val Phe His Val Ala Ser Arg Asn Gly Leu Asp Ile Glu Val
    450                 455                 460

Leu Gly Tyr Glu Ala Gly Val Ala Leu Leu Gln Ala Lys Val Ile Ala
465                 470                 475                 480

Asp Glu Gly Glu Leu Phe Ala Leu Thr Glu Arg Asp Leu Leu Arg Thr
                485                 490                 495

Asp Leu Phe Arg Thr Lys Ala Gly Glu Leu Ser Ala Asn Gly Lys Arg
```

```
                   500              505              510
Leu Leu Val Asn Leu Asp Lys Ala Lys Ala Pro Leu Trp Arg Val
            515              520              525
Leu Val Ala Leu Ser Ile Arg His Val Gly Pro Thr Ala Arg Ala
            530              535              540
Leu Ala Thr Glu Phe Gly Ser Leu Asp Ala Ile Ala Ala Ser Thr
545              550              555              560
Asp Gln Leu Ala Ala Val Glu Gly Val Gly Pro Thr Ile Ala Ala Ala
                565              570              575
Val Thr Glu Trp Phe Ala Val Asp Trp His Arg Glu Ile Val Asp Lys
                580              585              590
Trp Arg Ala Ala Gly Val Arg Met Val Asp Glu Arg Asp Glu Ser Val
            595              600              605
Pro Arg Thr Leu Ala Gly Leu Thr Ile Val Val Thr Gly Ser Leu Thr
            610              615              620
Gly Phe Ser Arg Asp Asp Ala Lys Glu Ala Ile Val Ala Arg Gly Gly
625              630              635              640
Lys Ala Ala Gly Ser Val Ser Lys Lys Thr Asn Tyr Val Val Ala Gly
                645              650              655
Asp Ser Pro Gly Ser Lys Tyr Asp Lys Ala Val Glu Leu Gly Val Pro
                660              665              670
Ile Leu Asp Glu Asp Gly Phe Arg Arg Leu Leu Ala Asp Gly Pro Ala
            675              680              685
Ser Arg Thr
    690

<210> SEQ ID NO 59
<211> LENGTH: 676
<212> TYPE: PRT
<213> ORGANISM: Enterococcus faecalis (strain ATCC 700802/V583)

<400> SEQUENCE: 59

Met Glu Gln Gln Pro Leu Thr Leu Thr Ala Ala Thr Arg Ala Gln
1               5               10              15
Glu Leu Arg Lys Gln Leu Asn Gln Tyr Ser His Glu Tyr Tyr Val Lys
            20              25              30
Asp Gln Pro Ser Val Glu Asp Tyr Val Tyr Asp Arg Leu Tyr Lys Glu
            35              40              45
Leu Val Asp Ile Glu Thr Glu Phe Pro Asp Leu Ile Thr Pro Asp Ser
    50              55              60
Pro Thr Gln Arg Val Gly Gly Lys Val Leu Ser Gly Phe Glu Lys Ala
65              70              75              80
Pro His Asp Ile Pro Met Tyr Ser Leu Asn Asp Gly Phe Ser Lys Glu
                85              90              95
Asp Ile Phe Ala Phe Asp Glu Arg Val Arg Lys Ala Ile Gly Lys Pro
            100             105             110
Val Ala Tyr Cys Cys Glu Leu Lys Ile Asp Gly Leu Ala Ile Ser Leu
            115             120             125
Arg Tyr Glu Asn Gly Val Phe Val Arg Gly Ala Thr Arg Gly Asp Gly
    130             135             140
Thr Val Gly Glu Asn Ile Thr Glu Asn Leu Arg Thr Val Arg Ser Val
145             150             155             160
Pro Met Arg Leu Thr Glu Pro Ile Ser Val Glu Val Arg Gly Glu Cys
                165             170             175
```

```
Tyr Met Pro Lys Gln Ser Phe Val Ala Leu Asn Glu Glu Arg Glu Glu
            180                 185                 190

Asn Gly Gln Asp Ile Phe Ala Asn Pro Arg Asn Ala Ala Ala Gly Ser
        195                 200                 205

Leu Arg Gln Leu Asp Thr Lys Ile Val Ala Lys Arg Asn Leu Asn Thr
    210                 215                 220

Phe Leu Tyr Thr Val Ala Asp Phe Gly Pro Met Lys Ala Lys Thr Gln
225                 230                 235                 240

Phe Glu Ala Leu Glu Glu Leu Ser Ala Ile Gly Phe Arg Thr Asn Pro
                245                 250                 255

Glu Arg Gln Leu Cys Gln Ser Ile Asp Glu Val Trp Ala Tyr Ile Glu
            260                 265                 270

Glu Tyr His Glu Lys Arg Ser Thr Leu Pro Tyr Glu Ile Asp Gly Ile
        275                 280                 285

Val Ile Lys Val Asn Glu Phe Ala Leu Gln Asp Glu Leu Gly Phe Thr
    290                 295                 300

Val Lys Ala Pro Arg Trp Ala Ile Ala Tyr Lys Phe Pro Pro Glu Glu
305                 310                 315                 320

Ala Glu Thr Val Val Glu Asp Ile Glu Trp Thr Ile Gly Arg Thr Gly
                325                 330                 335

Val Val Thr Pro Thr Ala Val Met Ala Pro Val Arg Val Ala Gly Thr
            340                 345                 350

Thr Val Ser Arg Ala Ser Leu His Asn Ala Asp Phe Ile Gln Met Lys
        355                 360                 365

Asp Ile Arg Leu Asn Asp His Val Ile Ile Tyr Lys Ala Gly Asp Ile
370                 375                 380

Ile Pro Glu Val Ala Gln Val Leu Val Glu Lys Arg Ala Ala Asp Ser
385                 390                 395                 400

Gln Pro Tyr Glu Met Pro Thr His Cys Pro Ile Cys His Ser Glu Leu
                405                 410                 415

Val His Leu Asp Glu Glu Val Ala Leu Arg Cys Ile Asn Pro Lys Cys
            420                 425                 430

Pro Ala Gln Ile Lys Glu Gly Leu Asn His Phe Val Ser Arg Asn Ala
        435                 440                 445

Met Asn Ile Asp Gly Leu Gly Pro Arg Val Leu Ala Gln Met Tyr Asp
450                 455                 460

Lys Gly Leu Val Lys Asp Val Ala Asp Leu Tyr Phe Leu Thr Glu Glu
465                 470                 475                 480

Gln Leu Met Thr Leu Asp Lys Ile Lys Glu Lys Ser Ala Asn Asn Ile
                485                 490                 495

Tyr Thr Ala Ile Gln Gly Ser Lys Glu Asn Ser Val Glu Arg Leu Ile
            500                 505                 510

Phe Gly Leu Gly Ile Arg His Val Gly Ala Lys Ala Lys Ile Leu
        515                 520                 525

Ala Glu His Phe Gly Asp Leu Pro Thr Leu Ser Arg Ala Thr Ala Glu
    530                 535                 540

Glu Ile Val Ala Leu Asp Ser Ile Gly Glu Thr Ile Ala Asp Ser Val
545                 550                 555                 560

Val Thr Tyr Phe Glu Asn Glu Val His Glu Leu Met Ala Glu Leu
                565                 570                 575

Glu Lys Ala Gln Val Asn Leu Thr Tyr Lys Gly Leu Arg Thr Glu Gln
            580                 585                 590

Leu Ala Glu Val Glu Ser Pro Phe Lys Asp Lys Thr Val Val Leu Thr
```

```
                595                 600                 605
Gly Lys Leu Ala Gln Tyr Thr Arg Glu Glu Ala Lys Glu Lys Ile Glu
    610                 615                 620

Asn Leu Gly Gly Lys Val Thr Gly Ser Val Ser Lys Lys Thr Asp Ile
625                 630                 635                 640

Val Val Ala Gly Glu Asp Ala Gly Ser Lys Leu Thr Lys Ala Glu Ser
                645                 650                 655

Leu Gly Val Thr Val Trp Asn Glu Gln Glu Met Val Asp Ala Leu Asp
            660                 665                 670

Ala Ser His Phe
        675

<210> SEQ ID NO 60
<211> LENGTH: 670
<212> TYPE: PRT
<213> ORGANISM: Haemophilus influenzae (strain ATCC 51907/DSM 11121/
      KW20/Rd)

<400> SEQUENCE: 60

Met Thr Asn Ile Gln Thr Gln Leu Asp Asn Leu Arg Lys Thr Leu Arg
1               5                   10                  15

Gln Tyr Glu Tyr Glu Tyr His Val Leu Asp Asn Pro Ser Val Pro Asp
            20                  25                  30

Ser Glu Tyr Asp Arg Leu Phe His Gln Leu Lys Ala Leu Glu Leu Glu
        35                  40                  45

His Pro Glu Phe Leu Thr Ser Asp Ser Pro Thr Gln Arg Val Gly Ala
    50                  55                  60

Lys Pro Leu Ser Gly Phe Ser Gln Ile Arg His Glu Ile Pro Met Leu
65                  70                  75                  80

Ser Leu Asp Asn Ala Phe Ser Asp Ala Glu Phe Asn Ala Phe Val Lys
                85                  90                  95

Arg Ile Glu Asp Arg Leu Ile Leu Pro Lys Pro Leu Thr Phe Cys
            100                 105                 110

Cys Glu Pro Lys Leu Asp Gly Leu Ala Val Ser Ile Leu Tyr Val Asn
        115                 120                 125

Gly Glu Leu Thr Gln Ala Ala Thr Arg Gly Asp Gly Thr Thr Gly Glu
    130                 135                 140

Asp Ile Thr Ala Asn Ile Arg Thr Ile Arg Asn Val Pro Leu Gln Leu
145                 150                 155                 160

Leu Thr Asp Asn Pro Pro Ala Arg Leu Glu Val Arg Gly Glu Val Phe
                165                 170                 175

Met Pro His Ala Gly Phe Glu Arg Leu Asn Lys Tyr Ala Leu Glu His
            180                 185                 190

Asn Glu Lys Thr Phe Ala Asn Pro Arg Asn Ala Ala Ala Gly Ser Leu
        195                 200                 205

Arg Gln Leu Asp Pro Asn Ile Thr Ser Lys Arg Pro Leu Val Leu Asn
    210                 215                 220

Ala Tyr Gly Ile Gly Ile Ala Glu Gly Val Asp Leu Pro Thr Thr His
225                 230                 235                 240

Tyr Ala Arg Leu Gln Trp Leu Lys Ser Ile Gly Ile Pro Val Asn Pro
                245                 250                 255

Glu Ile Arg Leu Cys Asn Gly Ala Asp Glu Val Leu Gly Phe Tyr Arg
            260                 265                 270

Asp Ile Gln Asn Lys Arg Ser Ser Leu Gly Tyr Asp Ile Asp Gly Thr
        275                 280                 285
```

```
Val Leu Lys Ile Asn Asp Ile Ala Leu Gln Asn Glu Leu Gly Phe Ile
    290                 295                 300

Ser Lys Ala Pro Arg Trp Ala Ile Ala Tyr Lys Phe Pro Ala Gln Glu
305                 310                 315                 320

Glu Leu Thr Leu Leu Asn Asp Val Glu Phe Gln Val Gly Arg Thr Gly
                325                 330                 335

Ala Ile Thr Pro Val Ala Lys Leu Glu Pro Val Phe Val Ala Gly Val
            340                 345                 350

Thr Val Ser Asn Ala Thr Leu His Asn Gly Asp Glu Ile Glu Arg Leu
        355                 360                 365

Asn Ile Ala Ile Gly Asp Thr Val Val Ile Arg Arg Ala Gly Asp Val
    370                 375                 380

Ile Pro Gln Ile Ile Gly Val Leu His Glu Arg Pro Asp Asn Ala
385                 390                 395                 400

Lys Pro Ile Ile Phe Pro Thr Asn Cys Pro Val Cys Asp Ser Gln Ile
                405                 410                 415

Ile Arg Ile Glu Gly Glu Ala Val Ala Arg Cys Thr Gly Gly Leu Phe
            420                 425                 430

Cys Ala Ala Gln Arg Lys Glu Ala Leu Lys His Phe Val Ser Arg Lys
        435                 440                 445

Ala Met Asp Ile Asp Gly Val Gly Gly Lys Leu Ile Glu Gln Leu Val
    450                 455                 460

Asp Arg Glu Leu Ile His Thr Pro Ala Asp Leu Phe Lys Leu Asp Leu
465                 470                 475                 480

Thr Thr Leu Thr Arg Leu Glu Arg Met Gly Ala Lys Ser Ala Glu Asn
                485                 490                 495

Ala Leu Asn Ser Leu Glu Asn Ala Lys Ser Thr Thr Leu Ala Arg Phe
            500                 505                 510

Ile Phe Ala Leu Gly Ile Arg Glu Val Gly Glu Ala Thr Ala Leu Asn
        515                 520                 525

Leu Ala Asn His Phe Lys Thr Leu Asp Ala Leu Lys Asp Ala Asn Leu
    530                 535                 540

Glu Glu Leu Gln Gln Val Pro Asp Val Gly Glu Val Val Ala Asn Arg
545                 550                 555                 560

Ile Phe Ile Phe Trp Arg Glu Ala His Asn Val Ala Val Val Glu Asp
                565                 570                 575

Leu Ile Ala Gln Gly Val His Trp Glu Thr Val Glu Val Lys Glu Ala
            580                 585                 590

Ser Glu Asn Leu Phe Lys Asp Lys Thr Val Val Leu Thr Gly Thr Leu
        595                 600                 605

Thr Gln Met Gly Arg Asn Glu Ala Lys Ala Leu Leu Gln Gln Leu Gly
    610                 615                 620

Ala Lys Val Ser Gly Ser Val Ser Ser Lys Thr Asp Phe Val Ile Ala
625                 630                 635                 640

Gly Asp Ala Ala Gly Ser Lys Leu Ala Lys Ala Gln Glu Leu Asn Ile
                645                 650                 655

Thr Val Leu Thr Glu Glu Glu Phe Leu Ala Gln Ile Thr Arg
            660                 665                 670

<210> SEQ ID NO 61
<211> LENGTH: 667
<212> TYPE: PRT
<213> ORGANISM: Staphylococcus aureus
```

<400> SEQUENCE: 61

Met Ala Asp Leu Ser Ser Arg Val Asn Glu Leu His Asp Leu Leu Asn
1               5                   10                  15
Gln Tyr Ser Tyr Glu Tyr Tyr Val Glu Asp Asn Pro Ser Val Pro Asp
            20                  25                  30
Ser Glu Tyr Asp Lys Leu Leu His Glu Leu Ile Lys Ile Glu Glu Glu
        35                  40                  45
His Pro Glu Tyr Lys Thr Val Asp Ser Pro Thr Val Arg Val Gly Gly
    50                  55                  60
Glu Ala Gln Ala Ser Phe Asn Lys Val Asn His Asp Thr Pro Met Leu
65                  70                  75                  80
Ser Leu Gly Asn Ala Phe Asn Glu Asp Asp Leu Arg Lys Phe Asp Gln
                85                  90                  95
Arg Ile Arg Glu Gln Ile Gly Asn Val Glu Tyr Met Cys Glu Leu Lys
            100                 105                 110
Ile Asp Gly Leu Ala Val Ser Leu Lys Tyr Val Asp Gly Tyr Phe Val
        115                 120                 125
Gln Gly Leu Thr Arg Gly Asp Gly Thr Thr Gly Glu Asp Ile Thr Glu
    130                 135                 140
Asn Leu Lys Thr Ile His Ala Ile Pro Leu Lys Met Lys Glu Pro Leu
145                 150                 155                 160
Asn Val Glu Val Arg Gly Glu Ala Tyr Met Pro Arg Arg Ser Phe Leu
                165                 170                 175
Arg Leu Asn Glu Glu Lys Glu Lys Asn Asp Glu Gln Leu Phe Ala Asn
            180                 185                 190
Pro Arg Asn Ala Ala Ala Gly Ser Leu Arg Gln Leu Asp Ser Lys Leu
        195                 200                 205
Thr Ala Lys Arg Lys Leu Ser Val Phe Ile Tyr Ser Val Asn Asp Phe
210                 215                 220
Thr Asp Phe Asn Ala Arg Ser Gln Ser Glu Ala Leu Asp Glu Leu Asp
225                 230                 235                 240
Lys Leu Gly Phe Thr Thr Asn Lys Asn Arg Ala Arg Val Asn Asn Ile
                245                 250                 255
Asp Gly Val Leu Glu Tyr Ile Glu Lys Trp Thr Ser Gln Arg Glu Ser
            260                 265                 270
Leu Pro Tyr Asp Ile Asp Gly Ile Val Ile Lys Val Asn Asp Leu Asp
        275                 280                 285
Gln Gln Asp Glu Met Gly Phe Thr Gln Lys Ser Pro Arg Trp Ala Ile
    290                 295                 300
Ala Tyr Lys Phe Pro Ala Glu Glu Val Val Thr Lys Leu Leu Asp Ile
305                 310                 315                 320
Glu Leu Ser Ile Gly Arg Thr Gly Val Val Thr Pro Thr Ala Ile Leu
                325                 330                 335
Glu Pro Val Lys Val Ala Gly Thr Thr Val Ser Arg Ala Ser Leu His
            340                 345                 350
Asn Glu Asp Leu Ile His Asp Arg Asp Ile Arg Ile Gly Asp Ser Val
        355                 360                 365
Val Val Lys Lys Ala Gly Asp Ile Ile Pro Glu Val Val Arg Ser Ile
    370                 375                 380
Pro Glu Arg Arg Pro Glu Asp Ala Val Thr Tyr His Met Pro Thr His
385                 390                 395                 400
Cys Pro Ser Cys Gly His Glu Leu Val Arg Ile Glu Gly Glu Val Ala
                405                 410                 415

```
Leu Arg Cys Ile Asn Pro Lys Cys Gln Ala Gln Leu Val Glu Gly Leu
            420                 425                 430

Ile His Phe Val Ser Arg Gln Ala Met Asn Ile Asp Gly Leu Gly Thr
            435                 440                 445

Lys Ile Ile Gln Gln Leu Tyr Gln Ser Glu Leu Ile Lys Asp Val Ala
        450                 455                 460

Asp Ile Phe Tyr Leu Thr Glu Glu Asp Leu Leu Pro Leu Asp Arg Met
465                 470                 475                 480

Gly Gln Lys Lys Val Asp Asn Leu Leu Ala Ala Ile Gln Gln Ala Lys
                485                 490                 495

Asp Asn Ser Leu Glu Asn Leu Leu Phe Gly Leu Gly Ile Arg His Leu
            500                 505                 510

Gly Val Lys Ala Ser Gln Val Leu Ala Glu Lys Tyr Glu Thr Ile Asp
        515                 520                 525

Arg Leu Leu Thr Val Thr Glu Ala Glu Leu Val Glu Ile His Asp Ile
        530                 535                 540

Gly Asp Lys Val Ala Gln Ser Val Val Thr Tyr Leu Glu Asn Glu Asp
545                 550                 555                 560

Ile Arg Ala Leu Ile Gln Lys Leu Lys Asp Lys His Val Asn Met Ile
            565                 570                 575

Tyr Lys Gly Ile Lys Thr Ser Asp Ile Glu Gly His Pro Glu Phe Ser
            580                 585                 590

Gly Lys Thr Ile Val Leu Thr Gly Lys Leu His Gln Met Thr Arg Asn
        595                 600                 605

Glu Ala Ser Lys Trp Leu Ala Ser Gln Gly Ala Lys Val Thr Ser Ser
        610                 615                 620

Val Thr Lys Asn Thr Asp Val Val Ile Ala Gly Glu Asp Ala Gly Ser
625                 630                 635                 640

Lys Leu Thr Lys Ala Gln Ser Leu Gly Ile Glu Ile Trp Thr Glu Gln
            645                 650                 655

Gln Phe Val Asp Lys Gln Asn Glu Leu Asn Ser
            660                 665

<210> SEQ ID NO 62
<211> LENGTH: 652
<212> TYPE: PRT
<213> ORGANISM: Streptococcus pneumoniae (strain P1031)

<400> SEQUENCE: 62

Met Asn Lys Arg Met Asn Glu Leu Val Ala Leu Leu Asn Arg Tyr Ala
1               5                   10                  15

Thr Glu Tyr Tyr Thr Ser Asp Asn Pro Ser Val Ser Asp Ser Glu Tyr
            20                  25                  30

Asp Arg Leu Tyr Arg Glu Leu Val Glu Leu Glu Thr Ala Tyr Pro Glu
        35                  40                  45

Gln Val Leu Ala Asp Ser Pro Thr His Arg Val Gly Gly Lys Val Leu
    50                  55                  60

Asp Gly Phe Glu Lys Tyr Ser His Gln Tyr Pro Leu Tyr Ser Leu Gln
65                  70                  75                  80

Asp Ala Phe Ser Arg Glu Glu Leu Asp Ala Phe Asp Ala Arg Val Arg
                85                  90                  95

Lys Glu Val Ala His Pro Thr Tyr Ile Cys Glu Leu Lys Ile Asp Gly
            100                 105                 110

Leu Ser Ile Ser Leu Thr Tyr Glu Lys Gly Ile Leu Val Ala Gly Val
```

```
                115                 120                 125
Thr Arg Gly Asp Gly Ser Ile Gly Glu Asn Ile Thr Glu Asn Leu Lys
130                 135                 140

Arg Val Lys Asp Ile Pro Leu Thr Leu Pro Glu Glu Leu Asp Ile Thr
145                 150                 155                 160

Val Arg Gly Glu Cys Tyr Met Pro Arg Ala Ser Phe Asp Gln Val Asn
                165                 170                 175

Gln Ala Arg Gln Glu Asn Gly Glu Pro Glu Phe Ala Asn Pro Arg Asn
            180                 185                 190

Ala Ala Ala Gly Thr Leu Arg Gln Leu Asp Thr Ala Val Val Ala Lys
        195                 200                 205

Arg Asn Leu Ala Thr Phe Leu Tyr Gln Glu Ala Ser Pro Ser Thr Arg
210                 215                 220

Asp Ser Gln Glu Lys Gly Leu Lys Tyr Leu Gln Leu Gly Phe Val
225                 230                 235                 240

Val Asn Pro Lys Arg Ile Leu Ala Glu Asn Ile Asp Glu Ile Trp Asn
                245                 250                 255

Phe Ile Gln Glu Val Gly Gln Glu Arg Glu Asn Leu Pro Tyr Asp Ile
            260                 265                 270

Asp Gly Val Val Ile Lys Val Asn Asp Leu Ala Ser Gln Glu Glu Leu
        275                 280                 285

Gly Phe Thr Val Lys Ala Pro Lys Trp Ala Val Ala Tyr Lys Phe Pro
290                 295                 300

Ala Glu Glu Lys Glu Ala Gln Leu Leu Ser Val Asp Trp Thr Val Gly
305                 310                 315                 320

Arg Thr Gly Val Val Thr Pro Thr Ala Asn Leu Thr Pro Val Gln Leu
                325                 330                 335

Ala Gly Thr Thr Val Ser Arg Ala Thr Leu His Asn Val Asp Tyr Ile
            340                 345                 350

Ala Glu Lys Asp Ile Arg Lys Asp Asp Thr Val Ile Val Tyr Lys Ala
        355                 360                 365

Gly Asp Ile Ile Pro Ala Val Leu Arg Val Val Glu Ser Lys Arg Val
370                 375                 380

Ser Glu Glu Lys Leu Asp Ile Pro Thr Asn Cys Pro Ser Cys Asn Ser
385                 390                 395                 400

Asp Leu Leu His Phe Glu Asp Glu Val Ala Leu Arg Cys Ile Asn Pro
                405                 410                 415

Arg Cys Pro Ala Gln Ile Met Glu Gly Leu Ile His Phe Ala Ser Arg
            420                 425                 430

Asp Ala Met Asn Ile Thr Gly Leu Gly Pro Ser Ile Val Glu Lys Leu
        435                 440                 445

Phe Ala Ala Asn Leu Val Lys Asp Val Ala Asp Ile Tyr Arg Leu Gln
450                 455                 460

Glu Glu Asp Phe Leu Leu Leu Glu Gly Val Lys Glu Lys Ser Ala Ala
465                 470                 475                 480

Lys Leu Tyr Gln Ala Ile Gln Ala Ser Lys Glu Asn Ser Ala Glu Lys
                485                 490                 495

Leu Leu Phe Gly Leu Gly Ile Arg His Val Gly Ser Lys Ala Ser Gln
            500                 505                 510

Leu Leu Leu Gln Tyr Phe His Ser Ile Glu Asn Leu Tyr Gln Ala Asp
        515                 520                 525

Ser Glu Glu Val Ala Ser Ile Glu Ser Leu Gly Gly Val Ile Ala Lys
530                 535                 540
```

-continued

```
Ser Leu Gln Thr Tyr Phe Ala Thr Glu Gly Ser Glu Ile Leu Leu Arg
545                 550                 555                 560

Glu Leu Lys Glu Thr Gly Val Asn Leu Asp Tyr Lys Gly Gln Thr Val
                565                 570                 575

Val Ala Asp Ala Ala Leu Ser Gly Leu Thr Val Val Leu Thr Gly Lys
            580                 585                 590

Leu Glu Arg Leu Lys Arg Ser Glu Ala Lys Ser Lys Leu Glu Ser Leu
        595                 600                 605

Gly Ala Lys Val Thr Gly Ser Val Ser Lys Lys Thr Asp Leu Val Val
        610                 615                 620

Val Gly Ala Asp Ala Gly Ser Lys Leu Gln Lys Ala Gln Glu Leu Gly
625                 630                 635                 640

Ile Gln Val Arg Asp Glu Ala Trp Leu Glu Ser Leu
                645                 650
```

PROCESSES FOR THE PRODUCTION OF OLIGONUCLEOTIDES

CROSS REFERENCE TO RELATED APPLICATION

This application is a continuation of U.S. application Ser. No. 15/643,535, filed 7 Jul. 2017, now U.S. Pat. No. 10,640,812, issued 5 May 2020, which claims the benefit of U.K. Provisional Application No. GB 1612011.5, filed 11 Jul. 2016.

FIELD OF THE INVENTION

The invention relates to novel processes for the production of oligonucleotides that are suitable for use in the production of chemically modified oligonucleotides, such as those used in therapy.

BACKGROUND TO THE INVENTION

The chemical synthesis of oligonucleotides and modified oligonucleotides via phosphoramidite chemistry is well established and has been the method of choice for synthesizing these defined sequence biopolymers for several decades. The synthetic process is usually run as a solid phase synthesis whereby single nucleotides are added sequentially with the addition of each nucleotide requiring a cycle of several chemical steps to add and deprotect the growing oligonucleotide ("oligo") in preparation for the subsequent step. At the end of the sequential addition of nucleotides the oligo is released from the solid phase support, further deprotection takes place, and then the crude oligonucleotide is further purified by column chromatography.

While this method may be considered routine and can be automated, there are several shortcomings to this methodology, especially if the goal is to prepare oligonucleotides at large scale as would be needed for oligonucleotide therapeutics. These shortcomings include, but are not limited to:
1) Practical limitations inherent in the use of chromatography making it unsuitable for purifying large quantities of oligonucleotide. The use of chromatography at large scale is expensive and is difficult to achieve due to the limitations on column size and performance.
2) The number of errors accumulates with the length of the oligonucleotide being synthesized. Accordingly, the linear sequential nature of the current process results in a geometric decrease in yield. For example, if the yield for each cycle of nucleotide addition is 99% then the yield of a 20 mer would be 83%.
3) Scale limitations with synthetic oligonucleotide synthesizers and downstream purification and isolation equipment: at present the maximum amount of product that can be produced in a single batch is in the order of 10 kg.

There is a need, therefore, to both reduce (or ideally eliminate) column chromatography and perform the synthesis in a way which is not purely sequential in order to increase yield.

DNA polymerase is often used to synthesize oligonucleotides for use in molecular biology and similar applications. However, DNA polymerase is unsuitable for synthesizing therapeutic oligonucleotides because of both the relatively short lengths of the oligonucleotides and the need to discriminate between nucleotides with different deoxyribose or ribose modifications. For example, therapeutic oligonucleotides are often in the range of 20 to 25 nucleotides. DNA polymerase needs at least 7 or 8 nucleotides, and optimally 18 to 22 nucleotides, as a primer in each direction so there is little to be gained in trying to synthesize a therapeutic oligo if the primers are similar in size to the desired product. Also, DNA polymerase requires all nucleotides to be present in the reaction and it relies on Watson-Crick base pairing to align incoming nucleotides. Thus it is unable to discriminate between any ordering of deoxyribose or ribose modifications, such as those required by a gapmer, and the result would be a mix of deoxyribose or ribose modifications at a given position.

SUMMARY OF THE INVENTION

The invention provides a process for producing a single stranded oligonucleotide product having at least one modified nucleotide residue, comprising:
  a) providing a template oligonucleotide (I) complimentary to the sequence of the product, said template having properties that allow it to be separated from the product;
  b) providing a pool of oligonucleotides (II);
  c) contacting (I) and (II) in conditions to allow annealing;
  d) changing the conditions to separate any impurities, comprising denaturing the annealed template and impurity oligonucleotide strands and separating the impurities; and
  e) changing the conditions to separate the product, comprising denaturing the annealed template and product oligonucleotide strands and separating the product.

Such a process may be used to isolate a single stranded oligonucleotide product from impurities, e.g. as a purification process.

The invention further provides a process for producing a single stranded oligonucleotide product having at least one modified nucleotide residue, comprising:
  a) providing a template oligonucleotide (I) complimentary to the sequence of the product, said template having properties that allow it to be separated from the product;
  b) providing a pool of oligonucleotides (II) containing oligonucleotides that are segments of the product sequence, wherein at least one segment contains at least one modified nucleotide residue;
  c) contacting (I) and (II) in conditions to allow annealing;
  d) joining the segment oligonucleotides to form the product;
  e) changing the conditions to separate any impurities, comprising denaturing the annealed template and impurity oligonucleotide strands and separating the impurities; and
  f) changing the conditions to separate the product, comprising denaturing the annealed template and product oligonucleotide strands and separating the product.

Such a process may be used to generate a single stranded oligonucleotide product and isolate it from impurities, e.g. as a manufacturing and purification process.

The invention also encompasses modified oligonucleotides made by such methods and ligases for use in such methods.

DESCRIPTION OF FIGURES

FIG. 15A is a chromatogram of the retentate solution, which remained in the filtration cell and contained mainly tri-template hub, after two diafiltration volumes; and chromatogram FIG. 15B is of the permeate, solution enriched in the product, after two diafiltration volumes.

FIG. 16A is a chromatogram of the retentate solution, which contained mainly tri-template hub and product, after 20 diafiltration volumes; and FIG. 16B is a chromatogram of the permeate, which contained mainly segment oligonucleotides, after 20 diafiltration volumes.

FIG. 17A shows a chromatogram of the retentate solution, which contained tri-template hub only, after 20 diafiltration volumes; and FIG. 17B is a chromatogram of the permeate solution, which contained the product only, after 2 diafiltration volumes.

DETAILED DESCRIPTION OF THE INVENTION

Definitions

Figure 1:
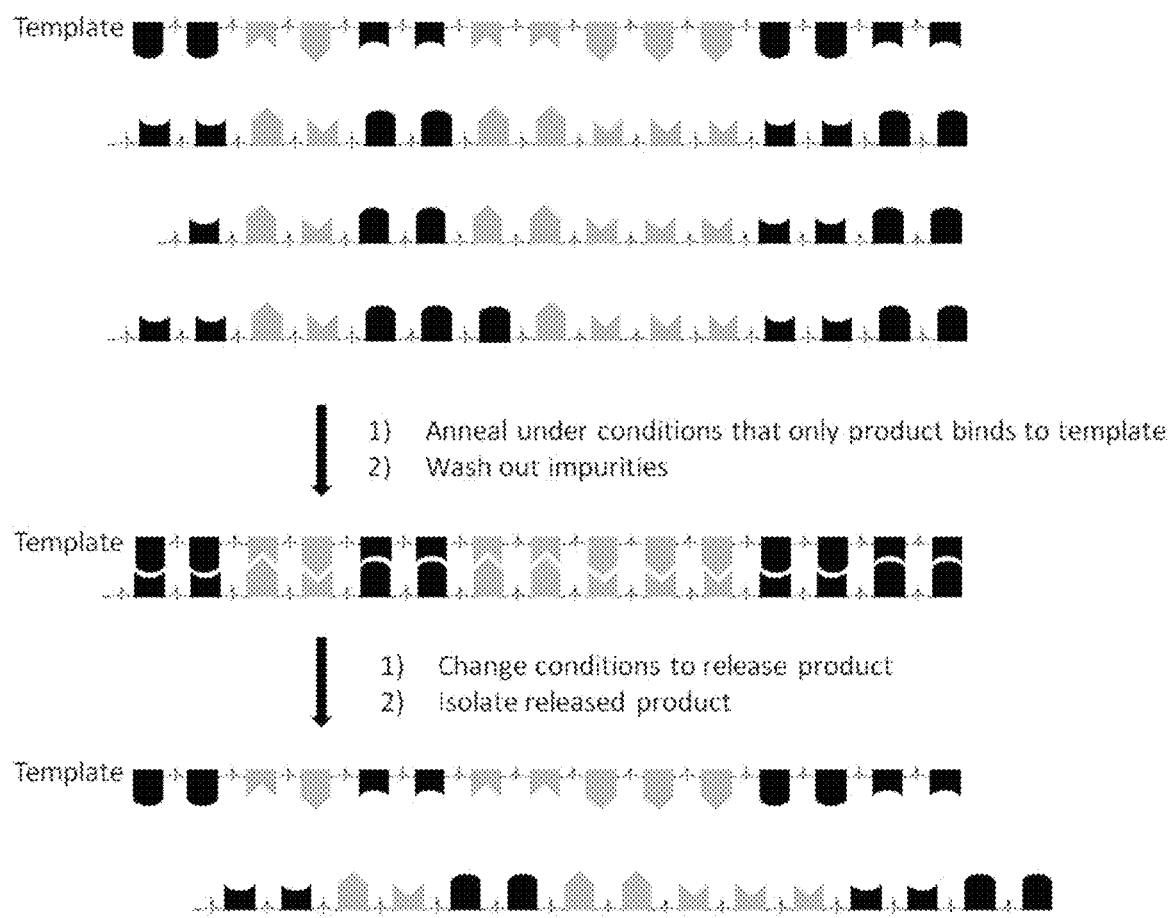
FIG. 1 Schematic of the process of the invention, including a step of changing the conditions to remove impurities, e.g. a washing step.
Figure 2:
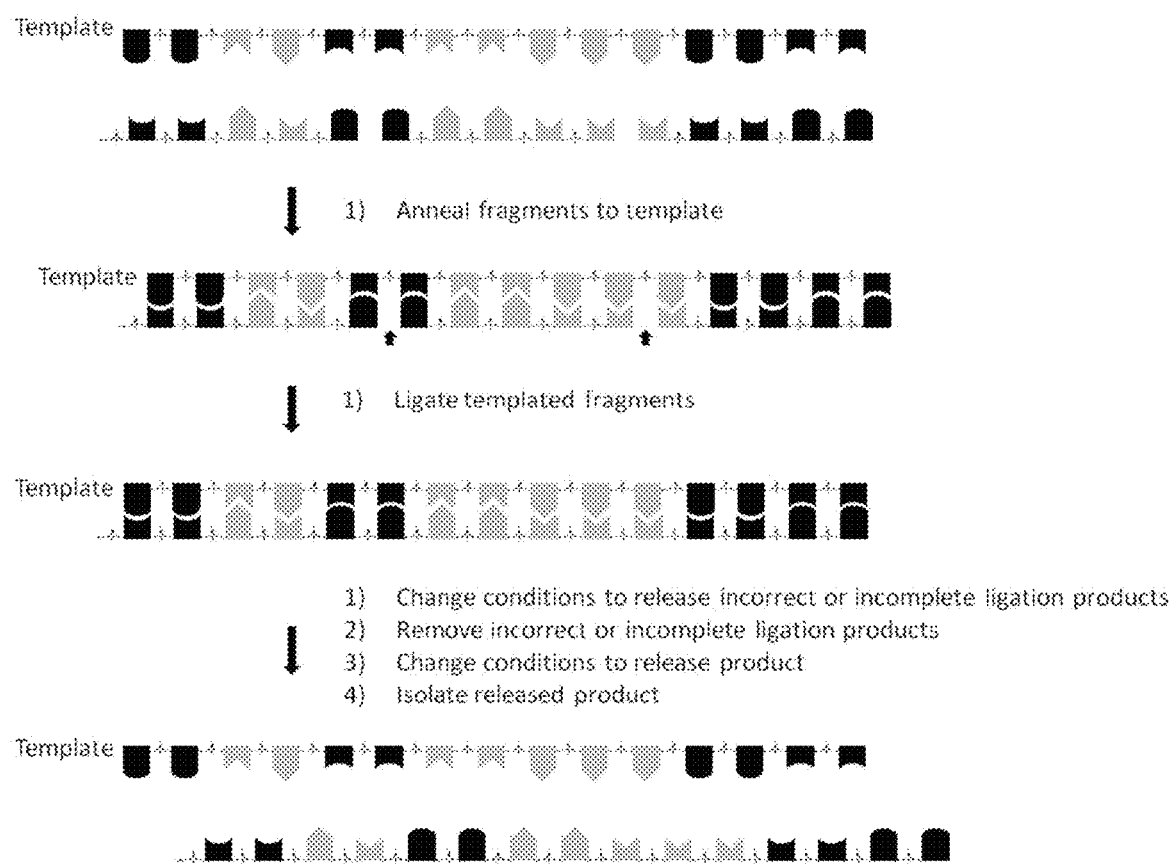
FIG. 2 Schematic of the process of the invention, including the steps of joining/ligating the segment oligonucleotides to form the product and changing the conditions to remove impurities.

As used herein, the term "oligonucleotide", or "oligo" for short, means a polymer of nucleotide residues, either deoxyribonucleotides (wherein the resulting oligonucleotide is DNA), ribonucleotides (wherein the resulting oligonucleotide is RNA), or a mixture thereof. An oligonucleotide may be entirely composed of nucleotide residues as found in nature or may contain at least one nucleotide, or at least one linkage between nucleotides, that has been modified. Oligonucleotides can be single stranded or double stranded. An oligonucleotide of the invention may be conjugated to another molecule, e.g. N-Acetylgalactosamine (GalNAc) or multiples thereof (GalNAc clusters).

As used herein, the term "therapeutic oligonucleotide" means an oligonucleotide that has a therapeutic application. Such an oligonucleotide typically contains one or more modified nucleotide residues or linkages. Therapeutic oligonucleotides act via one of several different mechanisms, including, but not limited to, antisense, splice-switching or exon-skipping, immunostimulation and RNA interference (RNAi), e.g. via microRNA (miRNA) and small interfering RNA (siRNA). A therapeutic oligonucleotide may be an aptamer. Therapeutic oligonucleotides will usually, but not always, have a defined sequence.

As used herein, the term "template" means an oligonucleotide with a sequence that is 100% complementary to the sequence of the target (or product) oligonucleotide.

Unless otherwise specified, as used herein, the term "complementary" means 100% complementary.

As used herein, the term "product" means the desired oligonucleotide, having a specific sequence, also referred to herein as a "target oligonucleotide".

As used herein, the term "pool" refers to a group of oligonucleotides that may vary in sequence, may be shorter or longer than the target sequence, and may not have the same sequence as the target sequence. The pool of oligonucleotides may be the product of oligonucleotide synthesis, e.g. solid phase chemical synthesis via phosphoramidite chemistry, used with or without purification. The pool of oligonucleotides may be composed of segments of the target sequence. Each segment itself may be present as a pool of that segment and may be the product of oligonucleotide synthesis, e.g. solid phase chemical synthesis via phosphoramidite chemistry.

As used herein, the term "annealing" means the hybridisation of complementary oligonucleotides in a sequence specific manner. "Conditions to allow for annealing" will depend on the $T_m$ of the hybridised complementary oligonucleotides and will be readily apparent to a person skilled in the art. For example, the temperature for annealing may be below the $T_m$ of the hybridised oligonucleotides. Alternatively, the temperature for annealing may be close to the $T_m$ of the hybridised oligonucleotides, e.g. +/−1, 2 or 3° C. The temperature for annealing is, in general, not higher than 10° C. above the $T_m$ of the hybridised oligonucleotides. Specific conditions to allow for annealing are as outlined in the examples section.

As used herein, the term "denaturing" in relation to a double stranded oligonucleotide is used to mean that the complementary strands are no longer annealed. Denaturing occurs as a result of changing the conditions and is sometimes referred to herein as separating the oligonucleotide strands. Such strand separation can be done for example, by raising the temperature, changing the pH, or changing the salt concentration of the buffering solution. Denaturing a double stranded oligonucleotide (a "duplex") results in a single stranded oligonucleotide which could be a product or impurity being "released" from the template.

Figure 6:
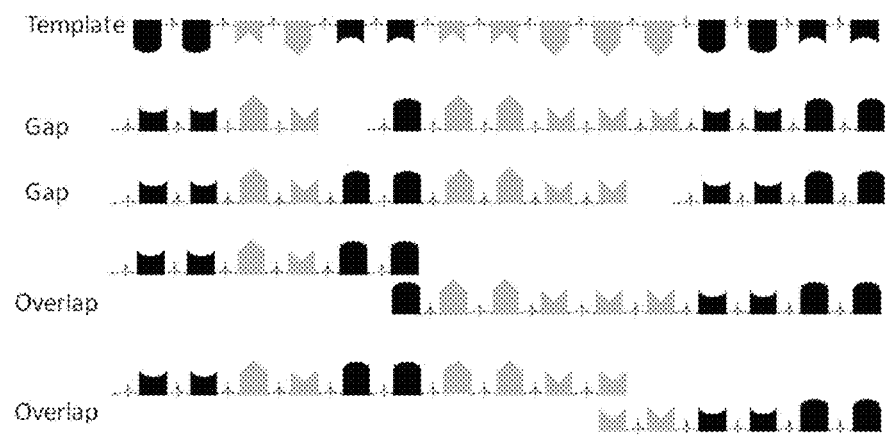
FIG. 6 Examples of impurities which may be generated during the process of the invention.
Figure 6:
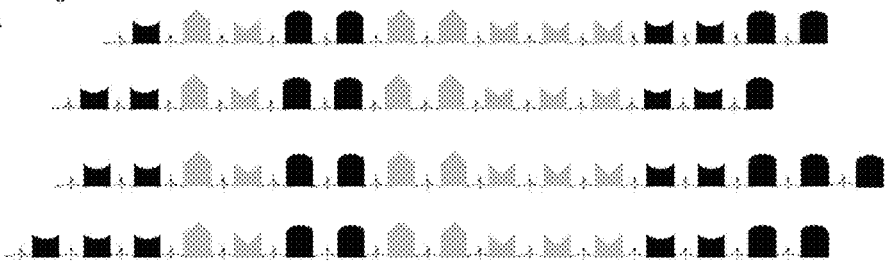

As used herein, the term "impurity" or "impurities" means oligonucleotides that do not have the desired product sequence. These oligonucleotides may include oligonucleotides that are shorter than the product (for example 1, 2, 3, 4, 5 or more nucleotide residues shorter), or that are longer than the product (for example 1, 2, 3, 4, 5 or more nucleotide residues longer). Where the production process includes a step whereby linkages are formed between segments, impurities include oligonucleotides that are remaining if one or more of the linkages fail to form. Impurities also include oligonucleotides where incorrect nucleotides have been incorporated, resulting in a mis-match when compared to the template. An impurity may have one or more of the characteristics described above. FIG. 6 shows some of the impurities that may occur.

As used herein, the term "segment" is a smaller portion of a longer oligonucleotide, in particular a smaller portion of a product or target oligonucleotide. For a given product, when all of its segments are annealed to its template and ligated together, the product is formed.

As used herein, the term "enzymatic ligation" means that the link between two adjacent nucleotides is formed enzymatically. This linkage may be a naturally occurring phosphodiester bond (PO), or a modified linkage including, but not limited to, phosphorothioate (PS) or phosphoramidate (PA).

As used herein, the term "ligase" means an enzyme that catalyses the joining, i.e. covalent joining, of two oligonucleotide molecules, e.g. by formation of a phosphodiester bond between the 3' end of one oligonucleotide (or segment) and the 5' end of the same or another oligonucleotide (or segment). These enzymes are often referred to as DNA ligases or RNA ligases and utilise cofactors: ATP (eukaryotic, viral and archael DNA ligases) or NAD (prokaryotic DNA ligases). Despite their occurrence in all organisms, DNA ligases show a wide diversity of amino acid sequences, molecular sizes and properties (Nucleic Acids Research, 2000, Vol. 28, No. 21, 4051-4058). They are usually members of the Enzyme Class EC 6.5 as defined by the International Union of Biochemistry and Molecular Biology, i.e. ligases used to form phosphoric ester bonds. Within the scope of the invention is a ligase capable of joining an unmodified oligonucleotide to another unmodified oligonucleotide, a ligase capable of joining an unmodified oligonucleotide to a modified oligonucleotide (i.e. a modified 5' oligonucleotide to an unmodified 3' oligonucleotide, and an unmodified 5' oligonucleotide to a modified 3' oligonucleotide), as well as a ligase capable of joining a modified oligonucleotide to another modified oligonucleotide.

As used herein, a "thermostable ligase" is a ligase that is active at elevated temperatures, i.e. above human body temperature, i.e. above 37° C. A thermostable ligase may be active at, for example, 40° C.-65° C.; or 40° C.-90° C.; and so forth.

As used herein, the term "modified nucleotide residue" or "modified oligonucleotide" means a nucleotide residue or oligonucleotide which contains at least one aspect of its chemistry that differs from a naturally occurring nucleotide residue or oligonucleotide. Such modifications can occur in any part of the nucleotide residue, e.g. sugar, base or phosphate. Examples of modifications of nucleotides are disclosed below.

As used herein, the term "modified ligase" means a ligase which differs from a naturally occurring, "wild-type", ligase by one or more amino acid residues. Such ligases are not found in nature. Such ligases are useful in the novel processes of the invention. Examples of modified ligases are disclosed below. The terms "modified ligase" and "mutant ligase" are used interchangeably.

As used herein, the term "gapmer" means an oligonucleotide having an internal "gap segment" flanked by two external "wing segments", wherein the gap segment consists of a plurality of nucleotides that support RNase H cleavage and each wing segment consists of one or more nucleotides that are chemically distinct to the nucleotides within the gap segment.

As used herein, the term "support material" means a high molecular weight compound or material that increases the molecular weight of the template, thereby allowing it to be retained when the impurities and products are separated from the reaction mixture.

As used herein "Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein. The query sequence may be 100% identical to the subject sequence, or it may include up to a certain integer number of nucleotide alterations as compared to the subject sequence such that the % identity is less than 100%. For example, the query sequence is at least 80, 85, 90, 95, 96, 97, 98, or 99% identical to the subject sequence.

STATEMENT OF THE INVENTION

In one aspect of the invention, there is provided a process for producing a single stranded oligonucleotide product having at least one modified nucleotide residue, comprising:
 a) providing a template oligonucleotide (I) complimentary to the sequence of the product, said template having properties that allow it to be separated from the product;
 b) providing a pool of oligonucleotides (II);
 c) contacting (I) and (II) in conditions to allow annealing;
 d) changing the conditions to separate any impurities, comprising denaturing the annealed template and impurity oligonucleotide strands and separating the impurities; and
 e) changing the conditions to separate the product, comprising denaturing the annealed template and product oligonucleotide strands and separating the product.

Such a process may be used to purify the product from impurities, e.g. a pool of oligonucleotides produced by chemical synthesis via phosphoramidite chemistry, e.g. solid phase chemical synthesis via phosphoramidite chemistry.

In a further embodiment of the invention there is provided a process comprising:

a) providing a template oligonucleotide (I) complimentary to the sequence of the product, said template having properties that allow it to be separated from the product;
b) providing a pool of oligonucleotides (II) that contains short oligonucleotides which are segments of the target sequence, wherein at least one segment contains at least one modified nucleotide residue;
c) contacting (I) and (II) in conditions to allow annealing;
d) joining the segment oligonucleotides;
e) changing the conditions to separate any impurities, comprising denaturing the annealed template and impurity oligonucleotide strands and separating the impurities; and
f) changing the conditions to separate the product, comprising denaturing the annealed template and product oligonucleotide strands and separating the product.

In an embodiment of the invention, there are substantially no nucleotides in the reaction vessel. In an embodiment of the invention, there are no nucleotides in the reaction vessel. In particular, the reaction vessel does not comprise a pool of nucleotides, i.e. the reaction is substantially free, preferably free, of nucleotides.

Another embodiment of the invention provides a process as previously described herein, whereby the denaturation results from a temperature increase.

One embodiment of the invention provides a process as previously disclosed herein, wherein the segment oligonucleotides are joined by enzymatic ligation. In a further embodiment the enzymatic ligation is carried out by a ligase.

Another embodiment of the invention provides a process as previously disclosed herein, whereby the segment oligonucleotides are joined by chemical ligation. In a further embodiment, the chemical ligation is a click chemistry reaction. In an embodiment of the invention, chemical ligation of segment oligonucleotides takes place in templated reactions that produce phosphoramidate linkages as detailed by Kalinowski et al. in ChemBioChem 2016, 17, 1150-1155.

Yet another embodiment of the invention provides a process as previously disclosed herein, whereby the segment oligonucleotides are 3 to 15 nucleotides long. In a further embodiment of the invention the segments are 5 to 10 nucleotides long. In a further embodiment of the invention the segments are 5 to 8 nucleotides long. In a further embodiment of the invention the segments are 5, 6, 7 or 8 nucleotides long. In a particular embodiment there are three segment oligonucleotides: a 5' segment that is 7 nucleotides long, a central segment that is 6 nucleotides long and a 3' segment that is 7 nucleotides long, which when ligated together form an oligonucleotide that is 20 nucleotides long (a "20-mer"). In a particular embodiment there are three segment oligonucleotides: a 5' segment that is 6 nucleotides long, a central segment that is 8 nucleotides long and a 3' segment that is 6 nucleotides long, which when ligated together form an oligonucleotide that is 20 nucleotides long (a "20-mer"). In a particular embodiment there are three segment oligonucleotides: a 5' segment that is 5 nucleotides long, a central segment that is 10 nucleotides long and a 3' segment that is 5 nucleotides long, which when ligated together form an oligonucleotide that is 20 nucleotides long (a "20-mer"). In a particular embodiment there are four segment oligonucleotides: a 5' segment that is 5 nucleotides long, a 5'-central segment that is 5 nucleotides long, a central-3' segment that is 5 nucleotides long, and a 3' segment that is 5 nucleotides long, which when ligated together form an oligonucleotide that is 20 nucleotides long (a "20-mer").

One embodiment of the invention provides a process as previously described herein, whereby the product is 10 to 200 nucleotides long. In a further embodiment of the invention the product is 15 to 30 nucleotides long. In an embodiment of the invention the product is 21, 22, 23, 24, 25, 26, 27, 28, 29 or 30 nucleotides long. In an embodiment of the invention the product is 20 nucleotides long, a "20-mer". In an embodiment of the invention the product is 21 nucleotides long, a "21-mer". In an embodiment of the invention the product is 22 nucleotides long, a "22-mer". In an embodiment of the invention the product is 23 nucleotides long, a "23-mer". In an embodiment of the invention the product is 24 nucleotides long, a "24-mer". In an embodiment of the invention the product is 25 nucleotides long, a "25-mer". In an embodiment of the invention the product is 26 nucleotides long, a "26-mer". In an embodiment of the invention the product is 27 nucleotides long, a "27-mer". In an embodiment of the invention the product is 28 nucleotides long, a "28-mer". In an embodiment of the invention the product is 29 nucleotides long, a "29-mer". In an embodiment of the invention the product is 30 nucleotides long, a "30-mer".

In an embodiment of the invention, the process is a process for producing a therapeutic oligonucleotide. In an embodiment of the invention, the process is a process for producing a single stranded therapeutic oligonucleotide. In an embodiment of the invention, the process is a process for producing a double stranded therapeutic oligonucleotide.

Another embodiment of the invention provides a process as previously disclosed herein, wherein the property that allows the template to be separated from the product is that the template is attached to a support material. In a further embodiment of the invention, the support material is a soluble support material. In a yet further embodiment of the invention the soluble support material is selected from the group consisting of: polyethylene glycol, a soluble organic polymer, DNA, a protein, a dendrimer, a polysaccharide, an oligosaccharide, and a carbohydrate. In an embodiment of the invention the support material is polyethylene glycol (PEG). In a further embodiment of the invention, the support material is an insoluble support material. In a further embodiment of the invention the support material is a solid support material. In a yet further embodiment, the solid support material is selected from the group consisting of: a glass bead, a polymeric bead, a fibrous support, a membrane, a streptavidin coated bead and cellulose. In an embodiment the solid support material is a streptavidin coated bead. In a further embodiment, the solid support material is part of the reaction vessel itself, e.g. a reaction wall.

Figure 3:
FIG. 3 Schematic of multiple template configurations.
Figure 3:
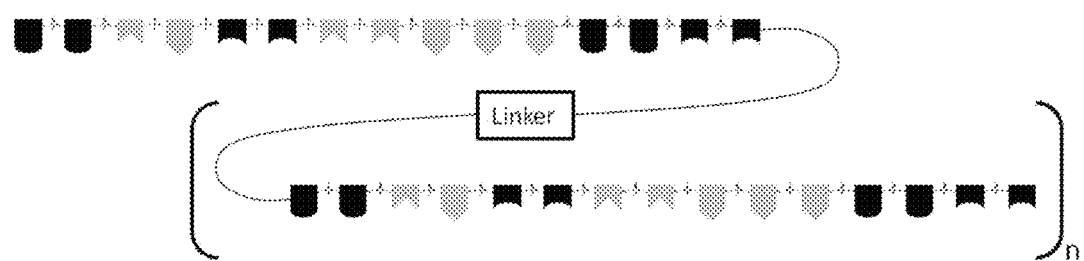
Figure 4:
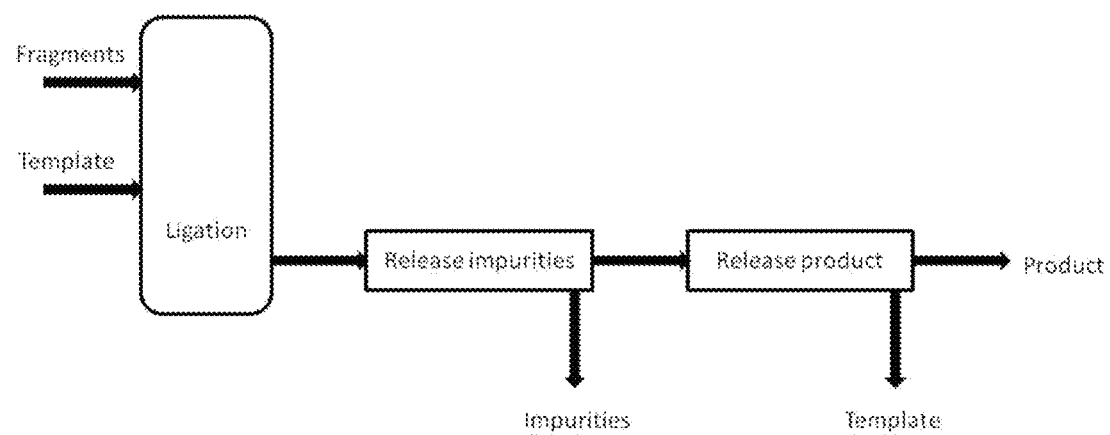
FIG. 4 Basic schematic of the process of the invention being carried out in a flow system.
Figure 5A:
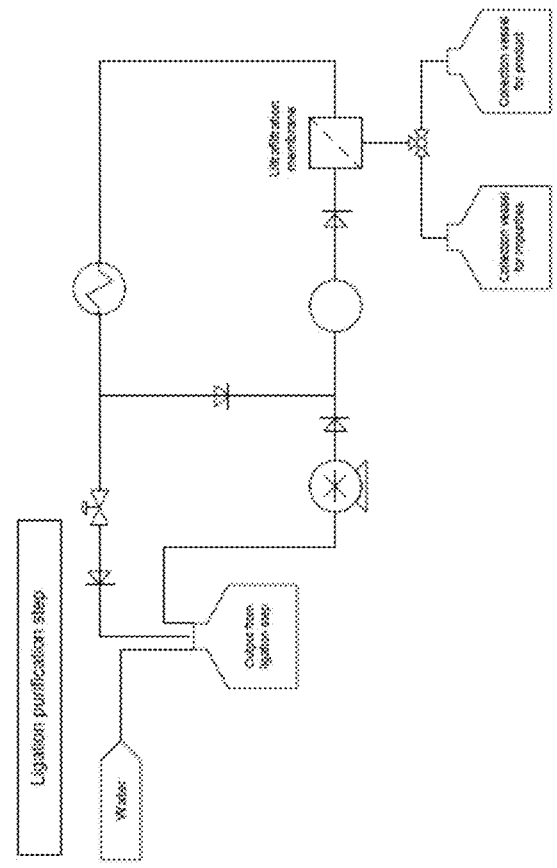
FIG. 5A, FIG. 5B, FIG. 5C and FIG. 5D Detailed schematic of the process of the invention being carried out in a flow system: ligation chemistry section (FIG. 5A), ligation purification section (FIG. 5B), and alternative ligation chemistry section (FIG. 5C), and alternative purification section (FIG. 5D). N.B. sections FIG. 5A and FIG. 5B (alternatively FIG. 5C and FIG. 5D) can be performed in a single step e.g. collection vessel in FIG. 5A=output from ligation step in FIG. 5B.
Figure 5B:
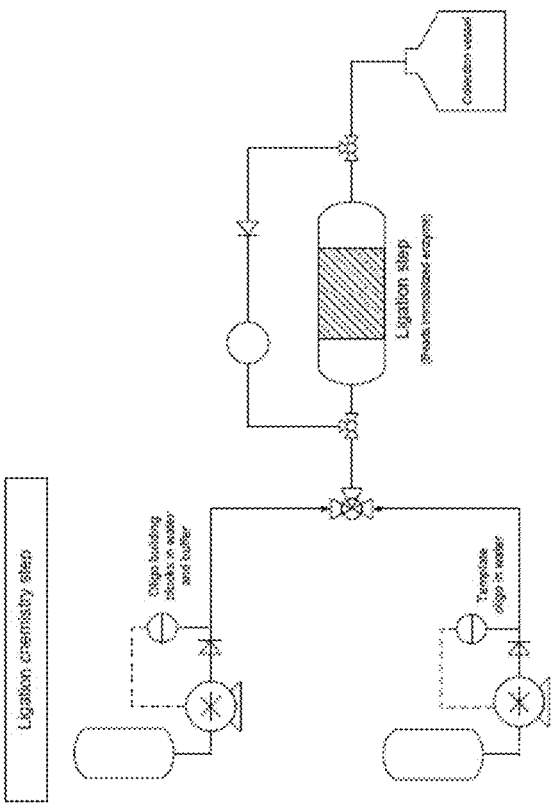
Figure 5D:
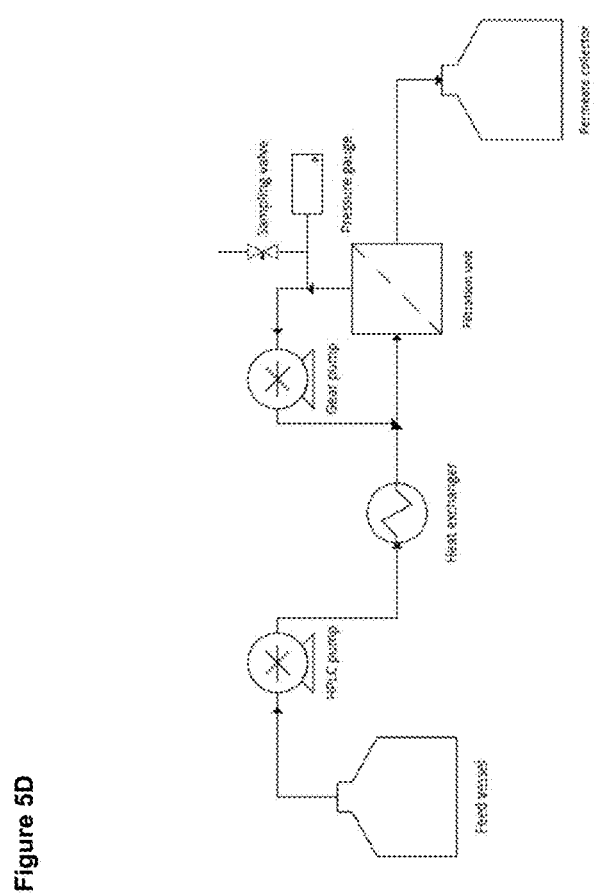
Figure 5C:
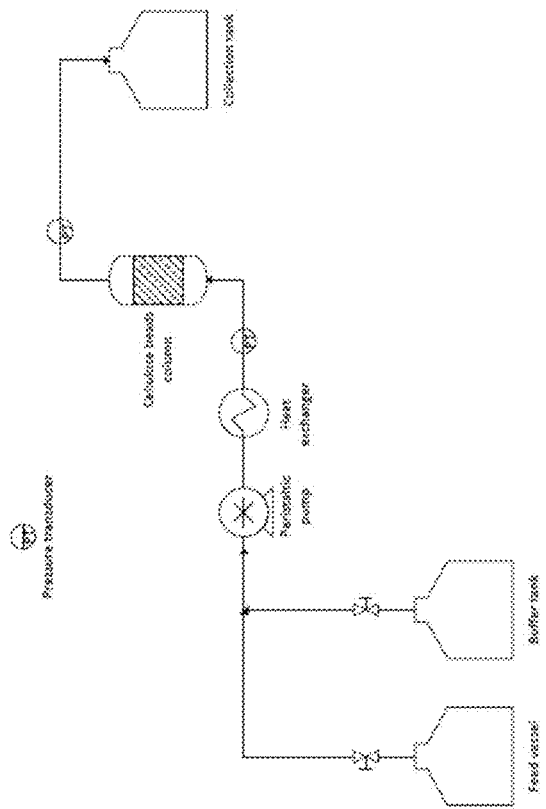

One embodiment of the invention provides a process as previously disclosed herein, wherein multiple, repeated copies of the template are attached in a continuous manner via a single attachment point to the support material. The multiple repeated copies of the template may be separated by a linker, e.g. as shown in FIG. 3. The multiple repeated copies of the template may be direct repeats, e.g. they are not separated by a linker.

Yet another embodiment of the invention provides a process as previously disclosed herein, wherein the property that allows the template to be separated from the product is the molecular weight of the template. For example, repeated copies of the template sequence may be present on a single oligonucleotide, with or without a linker sequence.

Another embodiment of the invention provides a process as previously disclosed herein, wherein the template, or the template and support material, are recycled for use in future reactions, for example as detailed below. Another embodiment of the invention provides a process as previously disclosed herein, wherein the reaction is carried out using a continuous or semi-continuous flow process, for example as shown in FIG. 4 or FIGS. 5A, 5B, 5C and 5D.

In an embodiment of the invention, the process is for large scale manufacture of oligonucleotides, in particular therapeutic oligonucleotides. In the context of the present invention large scale manufacture of oligonucleotides means manufacture at a scale greater than or equal to 1 litre, e.g. the process is carried out in a 1 L or larger reactor. Alternatively or in addition, in the context of the present invention large scale manufacture of oligonucleotides means manufacture at gram scale of product, in particular the production of greater than or equal to 10 grams of product. In an embodiment of the invention, the amount of oligonucleotide product produced is at gram scale. In an embodiment of the invention the amount of product produced is greater than or equal to: 1, 2, 3, 4, 5, 6, 7, 8, 9, 10, 20, 30, 40, 50, 60, 70, 80, 90 or 100 grams. In an embodiment of the invention, the amount of oligonucleotide product produced is greater than or equal to: 150, 200, 250, 300, 350, 400, 450, 500, 550, 600, 650, 700, 750, 800, 850, 900, 950 grams. In an embodiment of the invention, the amount of oligonucleotide product produced is 500 grams or greater. In an embodiment of the invention, the oligonucleotide product produced is at kilogram scale. In an embodiment of the invention, the amount of oligonucleotide product produced is 1 kg or more. In an embodiment of the invention, the amount of oligonucleotide product produced is greater than or equal to: 1, 2, 3, 4, 5, 6, 7, 8, 9, 10 kg. In an embodiment of the invention, the amount of oligonucleotide product produced is greater than or equal to: 15, 20, 25, 30, 35, 40, 45, 50, 55, 60, 65, 70, 75, 80, 85, 90, 95 or 100 kg.

In an embodiment of the invention, the amount of product produced is between 10 grams and 100 kg. In an embodiment of the invention, the amount of product produced is between 10 grams and 50 kg. In an embodiment of the invention, the amount of product produced is between 100 grams and 100 kg. In an embodiment of the invention, the amount of product produced is between 100 grams and 50 kg. In an embodiment of the invention, the amount of product produced is between 500 grams and 100 kg. In an embodiment of the invention, the amount of product produced is between 500 grams and 50 kg. In an embodiment of the invention, the amount of product produced is between 1 kg and 50 kg. In an embodiment of the invention, the amount of product produced is between 10 kg and 50 kg.

In an embodiment of the invention, oligonucleotide manufacture takes place at a scale greater than or equal to: 2, 3, 4, 5, 6, 7, 8, 9, 10 litres, e.g. in a 2, 3, 4, 5, 6, 7, 8, 9 or 10 L reactor. In an embodiment of the invention, oligonucleotide manufacture takes place at a scale greater than or equal to: 20, 25, 30, 35, 40, 45, 50, 55, 60, 65 70, 75, 80, 85, 90, 95, 100 litres, e.g. in a 20, 25, 30, 35, 40, 45, 50, 55, 60, 65 70, 75, 80, 85, 90, 95, 100 L reactor. In an embodiment of the invention, oligonucleotide manufacture takes place at a scale greater than or equal to: 150, 200, 250, 300, 350, 400, 450, 500, 550, 600, 650, 700, 750, 800, 850, 900, 950, 1000 litres, e.g. in 150, 200, 250, 300, 350, 400, 450, 500, 550, 600, 650, 700, 750, 800, 850, 900, 950, 1000 L reactor.

In an embodiment of the invention, the reactor volume is about 10,000 L, about 5000 L, about 2000 L, about 1000 L, about 500 L, about 125 L, about 50 L, about 20 L, about 10 L, or about 5 L.

In an embodiment of the invention, the reactor volume is between 5 and 10,000 L, between 10 and 5000 L, between 20 and 2000 L, or between 50 and 1000 L.

An oligonucleotide in accordance with the present invention may have at least one backbone modification, and/or at least one sugar modification and/or at least one base modification compared to an RNA or DNA-based oligonucleotide.

One embodiment of the invention provides a process as previously disclosed herein, wherein the product contains at least 1 modified nucleotide residue. In a further embodiment the modification is at the 2' position of the sugar moiety.

Oligonucleotides used in the process of the invention may include sugar modifications, i.e. a modified version of the ribosyl moiety, such as 2'-O-modified RNA such as 2'-O-alkyl or 2'-O-(substituted) alkyl e.g. 2'-O-methyl, 2'-O-(2-cyanoethyl), 2'-O-(2-methoxy) ethyl (2'-MOE), 2'-O-(2-thiomethyl) ethyl, 2'-O-butyryl, 2'-O-propargyl, 2'-O-allyl, 2'-O-(3-amino) propyl, 2'-O-(3-(dimethylamino) propyl), 2'-O-(2-amino) ethyl, 2'-O-(2-(dimethylamino)ethyl); 2'-deoxy (DNA); 2'-O-(haloalkoxy) methyl (Arai K. et al. Bioorg. Med. Chem. 2011, 21, 6285) e.g. 2'-O-(2-chloroethoxy) methyl (MCEM), 2'-O-(2,2-dichloroethoxy) methyl (DCEM); 2'-O-alkoxycarbonyl e.g. 2'-O-[2-(methoxycarbonyl) ethyl] (MOCE), 2'-O-[2-(N-methylcarbamoyl) ethyl] (MCE), 2'-O-[2-(N, N-dimethylcarbamoyl) ethyl] (DCME); 2'-halo e.g. 2'-F, FANA (2'-F arabinosyl nucleic acid); carbasugar and azasugar modifications; 3'-O-alkyl e.g. 3'-O-methyl, 3'-O-butyryl, 3'-O-propargyl; and their derivatives.

In an embodiment of the invention, the sugar modification is selected from the group consisting of 2'-Fluoro (2'-F), 2'-O-methyl (2'-OMe), 2'-O-methoxyethyl (2'-MOE), and 2'-amino. In a yet further embodiment, the modification is 2'-MOE.

Other sugar modifications include "bridged" or "bicylic" nucleic acid (BNA), e.g. locked nucleic acid (LNA), xylo-LNA, α-L-LNA, β-D-LNA, cEt (2'-O,4'-C constrained ethyl) LNA, cMOEt (2'-O,4'-C constrained methoxyethyl) LNA, ethylene-bridged nucleic acid (ENA), tricyclo DNA; unlocked nucleic acid (UNA); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PPMO, PMOPlus, PMO-x); and their derivatives.

Oligonucleotides used in the process of the invention may include other modifications, such as peptide-base nucleic acid (PNA), boron modified PNA, pyrrolidine-based oxypeptide nucleic acid (POPNA), glycol- or glycerol-based nucleic acid (GNA), threose-based nucleic acid (TNA), acyclic threoninol-based nucleic acid (aTNA), oligonucleotides with integrated bases and backbones (ONIBs), pyrrolidine-amide oligonucleotides (POMs); and their derivatives.

In an embodiment of the invention, the modified oligonucleotide comprises a phosphorodiamidate morpholino oligomer (PMO), a locked nucleic acid (LNA), a peptide nucleic acid (PNA), a bridged nucleic acid (BNA) such as(S)-cEt-BNA, or a SPIEGELMER®.

In a further embodiment, the modification is in the nucleobase. Base modifications include modified versions of the natural purine and pyrimidine bases (e.g. adenine, uracil, guanine, cytosine, and thymine), such as inosine, hypoxanthine, orotic acid, agmatidine, lysidine, 2-thiopyrimidine (e.g. 2-thiouracil, 2-thiothymine), G-clamp and its derivatives, 5-substituted pyrimidine (e.g. 5-methylcytosine, 5-methyluracil, 5-halouracil, 5-propynyluracil, 5-propynylcytosine, 5-aminomethyluracil, 5-hydroxymethyluracil, 5-aminomethylcytosine, 5-hydroxymethylcytosine, Super T), 2,6-diaminopurine, 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; N2-cyclopentylguanine (cPent-G), N2-cyclopentyl-2-aminopurine (cPent-AP), and N2-propyl-2-aminopurine (Pr-AP), or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173. cPent-G, cPent-AP and Pr-AP were shown to reduce immunostimulatory effects when incorporated in siRNA (Peacock H. et al. J. Am. Chem. Soc. (2011), 133, 9200).

In an embodiment of the invention, the nucleobase modification is selected from the group consisting of 5-methyl pyrimidines, 7-deazaguanosines and abasic nucleotides. In an embodiment, the modification is a 5-methyl cytosine.

Oligonucleotides used in the process of this invention may include a backbone modification, e.g. a modified version of the phosphodiester present in RNA, such as phosphorothioate (PS), phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methylboranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, triazole, oxalyl, carbamate, methyleneimino (MMI), and thioacetamido nucleic acid (TANA); and their derivatives.

In a further embodiment, the modification is in the backbone and is selected from the group consisting of: phosphorothioate (PS), phosphoramidate (PA) and phosphorodiamidate. In an embodiment of the invention, the modified oligonucleotide is a phosphorodiamidate morpholino oligomer (PMO). A PMO has a backbone of methylenemorpholine rings with phosphorodiamidate linkages. In an embodiment of the invention the product has a phosphorothioate (PS) backbone.

In an embodiment of the invention, the oligonucleotide comprises a combination of two or more modifications as disclosed above. A person skilled in the art will appreciate that there are many synthetic derivatives of oligonucleotides.

In an embodiment of the invention, the product is a gapmer. In an embodiment of the invention the 5' and 3' wings of the gapmer comprise or consist of 2'-MOE modified nucleotides. In an embodiment of the invention the gap segment of the gapmer comprises or consists of nucleotides containing hydrogen at the 2' position of the sugar moiety, i.e. is DNA-like. In an embodiment of the invention the 5' and 3' wings of the gapmer consist of 2'MOE modified nucleotides and the gap segment of the gapmer consists of nucleotides containing hydrogen at the 2' position of the sugar moiety (i.e. deoxynucleotides). In an embodiment of the invention the 5' and 3' wings of the gapmer consist of 2'MOE modified nucleotides and the gap segment of the gapmer consists of nucleotides containing hydrogen at the 2' position of the sugar moiety (i.e. deoxynucleotides) and the linkages between all of the nucleotides are phosphorothioate linkages.

One embodiment of the invention provides a process as previously described herein, wherein the resulting product is greater than 90% pure. In a further embodiment, the product is greater than 95% pure. In a further embodiment, the product is greater than 96% pure. In a further embodiment, the product is greater than 97% pure. In a further embodiment, the product is greater than 98% pure. In a further embodiment, the product is greater than 99% pure. Purity of an oligonucleotide may be determined using any suitable method, e.g. high performance liquid chromatography (HPLC) or mass spectrometry (MS), in particular liquid chromatography-MS (LC-MS), HPLC-MS or capillary electrophoresis mass spectrometry (CEMS).

Yet another embodiment of the invention provides a process for producing double stranded oligonucleotides, wherein 2 complimentary single stranded oligonucleotides are produced by the method of any preceding embodiment and then mixed under conditions to allow annealing. In an embodiment, the product is a siRNA.

One embodiment of the invention provides an oligonucleotide produced by a process previously described herein. In an embodiment of the invention, the oligonucleotide produced is RNA. In an embodiment of the invention, the oligonucleotide produced is DNA. In an embodiment of the invention, the oligonucleotide produced comprises both RNA and DNA. In a further embodiment of the invention the oligonucleotide produced is a modified oligonucleotide. In an embodiment of the invention the oligonucleotide produced is an antisense oligonucleotide. In an embodiment of the invention the oligonucleotide produced is an aptamer. In an embodiment of the invention the oligonucleotide produced is a miRNA. In an embodiment of the invention, the product is a therapeutic oligonucleotide.

The invention herein disclosed utilises the properties of oligonucleotide binding to provide an improved process for their production. By providing a template oligonucleotide with 100% complementarity to the target sequence, and controlling the reaction conditions so that the product can be released and separated under specific conditions, a product with a high degree of purity can be obtained.

Releasing the Product (or Impurity) from the Template, i.e. Denaturing Product (or Impurity): Template Duplex, and Separating the Product (or Impurity)

Releasing the product (or where the process includes an additional step of impurity release, any impurities) from the template requires the Watson-Crick base pairing between the template oligonucleotide strand and the product (or impurity) to be broken. The product (or impurity) can then be separated from the template. This can occur as two separate steps, or as one combined step.

Releasing and separating the product (or impurity) can occur as one step, if the process is carried out in a column reactor. Running in a buffer that alters the pH or salt concentration, or contains a chemical agent that disrupts the base pairing (such as formamide or urea) will cause denaturation of the oligonucleotide strands, and the product (or impurity) will be eluted in the buffer.

When the process is carried out in other reaction vessels, the release and separation of the product (or impurity) can occur as a two-step process. First, the Watson-Crick base pairs are disrupted to separate the strands, and then the product (or impurity) is removed from the reaction vessel. When releasing and separating the product is carried out as a two-step process, the breaking of the Watson-Crick base pairs can be achieved by altering the buffer conditions (pH, salt) or introducing a chemical disrupting agent (formamide, urea). Alternatively, raising the temperature will also cause the dissociation of the two strands. The product (or impurities) can then be removed from the reaction vessel via methods including molecular weight based separation, charge based separation, hydrophobicity based separation, specific sequence based separation or a combination of these methods.

When the process is carried out in a continuous or semi-continuous flow reactor the release and separation of the product (or impurity) can be in either one step or two steps. For example, releasing and separating the product (or impurity) in one step could be effected by increasing the temperature to cause dissociation of the two strands and separating the released strands on the basis of molecular weight in the same part of the reactor that is used to elevate the temperature. Releasing and separating the product (or impurity) in two steps could be effected by increasing the temperature to cause dissociation of the two strands in one part of the reactor and separating the released strands on the basis of molecular weight in a different part of the reactor.

Specifically Releasing and Separating Impurities from the Template, but Retaining the Product on the Template Impurities arise when an incorrect nucleotide is incorporated into the oligonucleotide strand during chain extension, or when the chain extension reaction terminates early. Impurities also arise when the reaction includes the step of ligating segment oligonucleotides and one or more of the ligation steps fail to happen. The kinds of impurities which can arise are illustrated in FIG. 6.

The properties of Watson-Crick base pairing can be exploited to specifically release any impurities bound to the template prior to the release of the product. Each double stranded oligonucleotide will dissociate under specific conditions, and those conditions are different for sequences which do not have 100% complementarity when compared to sequences with 100% complementarity. Determining such conditions is within the remit of a skilled person.

A common way of denaturing oligonucleotides is by raising the temperature. The temperature at which half of the base pairs are dissociated, i.e. when 50% of the duplex is in the single-stranded state, is called the melting temperature, $T_m$. The most reliable and accurate means of determining the melting temperature is empirically. However, this is cumbersome and not usually necessary. Several formulas can be used to calculate $T_m$ values (Nucleic Acids Research 1987, 15 (13): 5069-5083; PNAS 1986, 83 (11): 3746-3750; *Biopolymers* 1997, 44 (3): 217-239) and numerous melting temperature calculators can be found on-line, hosted by reagent suppliers and universities. It is known that for a given oligonucleotide sequence, a variant with all phosphorothioate linkages will melt at a lower temperature than a variant with all phosphodiester linkages. Increasing the number of phosphorothioate linkages in an oligonucleotide tends to lower the $T_m$ of the oligonucleotide for its intended target.

To specifically separate the impurities from a reaction mixture, first the melting temperature of the product: template duplex is calculated. Then the reaction vessel is heated to a first temperature, e.g. a temperature below the melting temperature of the product: template duplex, for example 1, 2, 3, 4, 5, 6, 7, 8, 9 or 10 degrees centigrade below the melting temperature. This will cause the denaturing of oligonucleotides which are not the product, i.e. are not 100% complimentary to the template, from the template. These can then be removed from the reaction vessel using one of the methods disclosed above, e.g. molecular weight based separation, charge based separation, hydrophobicity based separation, specific sequence based separation or a combination of these methods. Then the reaction vessel will be raised to a second, higher, temperature, e.g. above the calculated melting temperature, for example 1, 2, 3, 4, 5, 6, 7, 8, 9 or 10 degrees centigrade above the melting temperature, to cause the denaturing of the product from the template. The product can then be removed from the reaction vessel using one of the methods disclosed above, e.g. molecular weight based separation, charge based separation, hydrophobicity-based separation, specific sequence based separation or a combination of these methods.

A similar process can be used when the disrupting agent is an agent which causes a change in pH, salt concentration or a chemical disrupting agent. The disrupting agent is increased in concentration until just below the concentration at which the product would dissociate, to cause the denaturing of oligonucleotides which are not the product from the template. These impurities can then be removed from the reaction vessel using one of the methods disclosed above. The disrupting agent is then increased in concentration to above the concentration at which the product dissociates from the template. The product can then be removed from the reaction vessel using one of the methods disclosed above.

The product obtained from a process such as disclosed above has a high degree of purity without the need for further purification steps. For example, the product obtained is greater than 95% pure.

Properties of the Template

The template requires a property which allows it to be retained in the reaction vessel when the product is removed, to prevent it from becoming an impurity in the product. In other words, the template has properties that allow it to be separated from the product. In one embodiment of the invention, this retention is achieved by coupling the template to a supporting material. This coupling results in a template-support complex which has a high molecular weight, and can therefore be retained in the reaction vessel when impurities and product are removed, for example by filtration. The template can be coupled to a solid support material such as polymeric beads, fibrous supports, membranes, streptavidin coated beads and cellulose. The template can also be coupled to a soluble support material such as polyethylene glycol, a soluble organic polymer, DNA, a protein, a dendrimer, a polysaccharide, an oligosaccharide and a carbohydrate.

Each support material can have multiple points where a template can be attached, and each attachment point can have multiple templates attached, e.g. in the manner shown in FIG. 3.

The template may have a high molecular weight itself, without being attached to a support material, for example, it may be a molecule with multiple copies of the template, e.g. separated by a linker, in the manner shown in FIG. 3.

The ability to retain the template in the reaction vessel also allows the template to be recycled for future reactions, either by being recovered or by use in a continuous or semi-continuous flow process.

Methods of Separating the Template from the Product (or Impurities)

The properties of the template, as disclosed above, allow separation of the template and product, or separation of the template bound product and impurities. Molecular weight based separation, charge based separation, hydrophobicity based separation, specific sequence based separation or a combination of these methods can be used.

In the case where the template is attached to a solid support, separation of the template from the product or separation of impurities from the product bound to the template is achieved by washing the solid support under appropriate conditions. In cases where the template is coupled to a soluble support or is itself composed of repeating template sequences, separation of template from product or separation of template bound product from impurities can be achieved by means of a molecular weight based separation. This can be achieved by using techniques such as ultra-filtration or nano-filtration where the filter material is chosen so that the larger molecule is retained by the filter and the smaller molecule passes through. In cases where a single separation step of impurity from template product complex or separation of product from template is not efficient enough, multiple sequential filtration steps can be employed to increase separation efficiency and so generate a product that meets the desired purity.

It is desirable to provide a process for separation of such oligonucleotides which is efficient and applicable on an industrial production scale. "Therapeutic oligonucleotides: The state of the art in purification technologies" Sanghvi et. al. Current Opinion in Drug Discovery (2004) Vol. 7 No. 8 reviews processes used for oligonucleotide purification.

WO-A-01/55160 discloses purification of oligonucleotides by forming imine linkages with contaminants then removing the imine-linked impurities with chromatography or other techniques. "Size Fractionation of DNA Fragments Ranging from 20 to 30000 Base Pairs by Liquid/Liquid chromatography" Muller et al. Eur. J. Biochem (1982) 128-238 discloses use of a solid column of microcrystalline cellulose on which has been deposited a PEG/dextran phase for separation of nucleotide sequences. "Separation and identification of oligonucleotides by hydrophilic interaction chromatography." Easter et. al. The Analyst (2010); 135 (10) discloses separation of oligonucleotides using a variant of HPLC employing a solid silica support phase. "Fractionation of oligonucleotides of yeast soluble ribonucleic acids by countercurrent distribution" Doctor et al. Biochemistry (1965) 4 (1) 49-54 discloses use of a dry solid column packed with dry DEAE-cellulose. "Oligonucleotide composition of a yeast lysine transfer ribonucleic acid" Madison et al; Biochemistry, 1974, 13 (3) discloses use of solid phase chromatography for separation of nucleotide sequences.

Liquid-liquid chromatography is a known separation method. "Countercurrent Chromatography The Support-Free Liquid Stationary Phase" Billardello, B.; Berthod, A; Wilson & Wilson's Comprehensive Analytical Chemistry 38; Berthod, A., Ed.; Elsevier Science B.V.: Amsterdam (2002) pp 177-200 provides a useful general description of liquid-liquid chromatography. Various liquid-liquid chromatography techniques are known. One technique is liquid-liquid counter current chromatography (termed herein "CCC"). Another known technique is centrifugal partition chromatography (termed herein "CPC").

The above disclosed methods and those methods set out in WO 2013/030263 may be used to separate a product oligonucleotide e.g. from the template and/or an impurity.

Oligonucleotides Used as Starting Materials

The oligonucleotides used as a starting material for the processes of the invention are herein described as being a "pool" and a definition thereof is provided above. The pool is a non-homogenous set of oligonucleotides. The oligonucleotides which form the pool will have been produced by other oligonucleotide production methods, and will therefore likely contain a high degree of impurities. Therefore when this pool of oligonucleotides is applied to a process of the invention, the ability to specifically remove impurities as described herein results in a purification step occurring.

The pool can contain oligonucleotides which are intended to be the same length as the template oligonucleotide (although will contain impurities of differing lengths, as well as incorrectly incorporated residues). The pool can also be composed of segments of the product oligonucleotides, which are joined together whilst assembled on the template. Each segment will be a non-homogeneous set with impurities of differing lengths and incorrectly incorporated residues.

Ligases

In an aspect of the invention, a ligase is provided. In an embodiment of the invention, the ligase is an ATP dependent ligase. ATP dependent ligases range in size from 30 to >100 kDa. In an embodiment of the invention, the ligase is an NAD dependent ligase. NAD dependent enzymes are highly homologous and are monomeric proteins of 70-80 kDa. In an embodiment of the invention, the ligase is a thermostable ligase. A thermostable ligase may be derived from a thermophilic bacteria.

In an embodiment of the invention, the ligase is a modified ligase. For example, a modified ligase includes a modified T4 DNA ligase, a modified Enterobacteria phage CC31 ligase, a modified *Shigella* phage Shf125875 ligase and a modified *Chlorella* ligase.

In an embodiment, wild-type T4 DNA ligase is modified at amino acid position 368 or amino acid position 371 of SEQ ID NO:3.

In an embodiment, the mutant ligase comprises or consists of SEQ ID NO:3 wherein the amino acid at position 368 is R or K.

In an embodiment, the mutant ligase comprises or consists of SEQ ID NO:3 wherein the amino acid at position 371 is any one of the following amino acids: L, K, Q, V, P, R.

In an embodiment, the corresponding residue(s) disclosed above in relation to T4 DNA ligase are mutated in any one of Enterobacteria phage CC31 ligase, *Shigella* phage Shf125875 ligase and *Chlorella* ligase. Conserved regions of DNA ligases are disclosed in Chem. Rev. 2006, 106, 687-699 and Nucleic Acids Research, 2000, Vol. 28, No. 21, 4051-4058. In an embodiment, the ligase is modified in a linker region.

In an embodiment of the invention, the ligase comprises or consists of SEQ ID NO: 23 or a ligase with at least 90% sequence identity thereto, excluding a wild type ligase e.g. Enterobacteria phage CC31 ligase.

In an embodiment of the invention, the ligase comprises or consists of any one of the following amino acid sequences: SEQ ID NOs: 10-28.

In an embodiment of the invention, the ligase is immobilised, e.g. on a bead.

In an aspect of the invention there is provided the use of a ligase comprising the amino acid sequence as set forth in SEQ ID NO:6 or SEQ ID NO:8 for ligating a 5' segment, containing one or more modified sugar moieties, to a 3' segment, wherein all of the sugar moieties within the 3' segment are unmodified. In an embodiment of the invention there is provided the use of a ligase comprising the amino acid sequence as set forth in SEQ ID NO:6 or SEQ ID NO:8 for ligating a 5' segment, containing one or more sugar moieties with a 2'-OMe modification, to a 3' segment, wherein all of the sugar moieties within the 3' segment are unmodified. In an embodiment, all of the sugar moieties in the 5' segment contain a 2'-OMe modification. In an embodiment, the 5' segment contains 5 sugar moieties with a 2'-OMe modification.

The present invention includes the following items:
1. A process for producing a single stranded oligonucleotide product comprising:
   a) providing a template oligonucleotide (I) complimentary to the sequence of the product, said template having properties that allow it to be separated from the product;
   b) providing a pool of oligonucleotides (II);
   c) contacting (I) and (II) in conditions to allow annealing; and
   d) changing the conditions to remove the product.
2. A process according to item 1, comprising:
   a) providing a template oligonucleotide (I) complimentary to the sequence of the product, said template having properties that allow it to be separated from the product;
   b) providing a pool of oligonucleotides (II);
   c) contacting (I) and (II) in conditions to allow annealing;
   d) changing the conditions to remove impurities; and
   e) changing the conditions to remove the product.
3. A process according to item 1 or 2, comprising:
   a) providing a template oligonucleotide (I) complimentary to the sequence of the product, said template having properties that allow it to be separated from the product;
   b) providing a pool of oligonucleotides (II) containing oligonucleotides that are segments of the product sequence;
   c) contacting (I) and (II) in conditions to allow annealing;
   d) joining the segment oligonucleotides to form the product;
   e) changing the conditions to remove impurities; and
   f) changing the conditions to remove the product.
4. A process according to any preceding item, whereby the process takes place in a reaction vessel, and whereby changing the conditions to remove product comprises the step of separating the annealed oligonucleotide strands and the step of removing the product from the reaction vessel.
5. A process according to any one of items 2-4, whereby the process takes place in a reaction vessel, and whereby changing the conditions to remove impurities comprises the step of separating the annealed oligonucleotide strands and the step of removing the impurities from the reaction vessel.
6. A process according to item 4 or 5, whereby the strand separation results from a temperature increase.
7. A process according to item 6, including two steps of increasing the temperature: i) to separate annealed impurities and ii) to separate annealed product.
8. A process according to items 3-7, wherein the segment oligonucleotides are joined by enzymatic ligation.
9. The process according to item 8, wherein the enzyme is a ligase.
10. A process according to any one of items 3-9, wherein the segments are 3 to 15 nucleotides long.
11. A process according to any preceding item, wherein the product is 10 to 200 nucleotides long.
12. A process according to item 11, wherein the product is 20 to 25 nucleotides long.
13. A process according to item 12, comprising three segment oligonucleotides: a 5' segment that is 7 nucleotides long, a central segment that is 6 nucleotides long and a 3' segment that is 7 nucleotides long.
14. A process according to item 12, comprising three segment oligonucleotides: a 5' segment that is 6 nucleotides long, a central segment that is 8 nucleotides long and a 3' segment that is 6 nucleotides long.
15. A process according to item 12, comprising three segment oligonucleotides: a 5' segment that is 5 nucleotides long, a central segment that is 10 nucleotides long and a 3' segment that is 5 nucleotides long.
16. A process according to any preceding item, wherein the property that allows the template to be separated from the product is that the template is attached to a support material.
17. The process according to item 16 wherein the support material is a soluble support material.
18. A process according to item 17 wherein the support material is polyethylene glycol.
19. A process according to any one of items 11-18, wherein multiple, repeated copies of the template are attached in a continuous manner via a single attachment point to the support material.
20. A process according to any one of items 1-15, wherein the property that allows the template to be separated from the product is the molecular weight of the template.
21. A process according to any preceding item, wherein the template, or the template and support material, are recycled for use in future reactions.
22. A process according to any preceding item, wherein the reaction is carried out using a continuous flow process.
23. A process according to any preceding item wherein the product contains at least one modified nucleotide residue.
24. A process according to item 23, wherein at least one segment contains at least one modified nucleotide residue.
25. The process according to item 23 or item 24, wherein the modification is at the 2' position of the sugar moiety.
26 The process according to item 25, wherein the modification is selected from the group consisting of 2'-F, 2'-OMe, 2'-MOE, and 2'-amino.
27 The process according to item 24, wherein the oligonucleotide comprises a PMO, a LNA, a PNA, a BNA, or a SPIEGELMER®TM.
28. The process according to item 23 or item 24, wherein the modification is in the nucleobase.
29 The process according to item 28 wherein the modification is selected from the group consisting of 5-methyl pyrimidines, 7-deazaguanosines and abasic nucleotides.
30. The process according to item 23 or item 24, wherein the modification is in the backbone.
31. The process according to item 30 wherein the modification is selected from the group consisting of phosphorothioate, phosphoramidate and phosphorodiamidate.
32. A process according to any preceding item, wherein the resulting product is at least 90% pure.

33. The process according item 32, wherein the product is at least 95% pure.

34. A process for producing double stranded oligonucleotides, wherein 2 complimentary single stranded oligonucleotides are produced by the method of any preceding item and then mixed under conditions to allow annealing.

35. A process as claimed in any of the preceding items, wherein the process is for producing a therapeutic oligonucleotide.

36 An oligonucleotide produced by the process of any one of items 1 to 35.

37 An oligonucleotide according to claim 36, wherein the oligonucleotide is a modified oligonucleotide produced by the process of any one of items 23 to 35.

38. An oligonucleotide according to item 37, wherein the oligonucleotide is a gapmer.

39. A ligase comprising the amino acid sequence as set out in SEQ ID NO: 3 wherein the amino acid at position 368 is replaced with R or K; and/or the amino acid at position 371 is replaced with L, K, Q, V, P, or R.

40. A ligase comprising the amino acid sequence as set forth in any one of the following SEQ ID NOs: 10-28.

41. Use of a ligase comprising the amino acid sequence as set forth in SEQ ID NO:6 or SEQ ID NO:8 for ligating a 5' segment, containing one or more sugar moieties with a 2'-OMe modification, to a 3' segment, wherein all of the sugar moieties within the 3' segment are unmodified.

EXAMPLES

Abbreviations

OMe O-Methyl
MOE O-Methoxyethyl (DNA backbone) or Methoxyethyl (RNA backbone)
CBD Cellulose Binding Domain
HPLC high performance liquid chromatography
PBS phosphate buffered saline
HAA Hexylammonium acetate
SDS PAGE sodium dodecyl sulphate polyacrylamide gel electrophoresis
LCMS liquid chromatography mass spectrometry
PO phosphodiester
DTT dithiothreitol Example 1: Oligonucleotide (DNA) Segment Assembly and Ligation with Wild-Type T4 DNA Ligase 1.1 Chemical Synthesis of Starting and Control Sequences In order to demonstrate that multiple short oligonucleotides ("segments") could be assembled in the correct order on a complementary template strand and ligated to give the desired final product ("target"), the segments, target and template sequences, as detailed in Table 1, were chemically synthesised using standard methods.

1.2 HPLC analysis

HPLC analysis was carried out using an Agilent ZORBAX Eclipse Plus XDB-C18 column (4.6×150 mm, 5 μm dp. Agilent P/N 993967-902) running at 0.2 ml/min while absorbance was monitored at 258 nm. The column was maintained at 60° C. 20 μl of sample was injected and a gradient from 20-31% buffer B was run over 20 minutes before being stepped up to 80% buffer B for 5 minutes.

Buffer A: 75 ml 1 M HAA, 300 ml isopropyl alcohol, 200 ml acetonitrile, 4425 ml water Buffer B: 650 ml isopropyl alcohol, 350 ml acetonitrile

TABLE 1

| Name | Sequence | % HPLC purity | Amount (mg) |
|---|---|---|---|
| 5' segment | 5'-GGC CAA-3' | 100.0 | 21.6 |
| centre segment | 5'-(p)ACC TCG GC-3' | 96.9 | 58.1 |
| 3' segment | 5'-(p)T TAC CT-3' | 98.8 | 39.8 |
| Target | 5'-GGC CAA ACC TCG GCT TAC CT-3' (SEQ ID NO: 1) | 98.4 | 101.7 |
| Biotinylated template | 5'-biotin TT TAG GTA AGC CGA GGT TTG GCC-3' (SEQ ID NO: 2) | 96.9 | 130.7 |

1.3 Oligonucleotide Assembly and Ligation Method with Commercial T4 DNA Ligase (SEQ ID NO:3)

The 5' segment, centre segment and 3' segment were assembled on the template: each segment and the template was dissolved in water at a concentration of 1 mg/ml and then mixed as follows.

| | |
|---|---|
| 5' segment | 2 μl |
| centre segment | 2 μl |
| 3' segment | 2 μl |
| biotinylated template | 2 μl |
| H$_2$O | 36 μl |

The combined oligonucleotide solution was incubated at 94° C. for 5 minutes and cooled to 37° C. before incubating at 37° C. for a further 5 minutes to allow the segments to anneal to the template. 2 μl (equivalent to 2 μg) T4 DNA ligase (NEB) and 4 μl of 1×T4 DNA Ligation Buffer (NEB) were then added and the reaction (total reaction volume 50 μl) was incubated at room temperature for one hour. Following this, 40 μl of streptavidin coated magnetic beads were added and the suspension incubated at room temperature for 10 minutes to allow the biotinylated template to bind to the streptavidin beads. The streptavidin beads were washed with 2×100 μl PBS to remove unbound segments.

The wash was analysed by HPLC. The reaction mixture was then incubated at 94° C. for 10 minutes to separate the bound ligation products (or any bound segments) from the template before being rapidly cooled on ice to 'melt' the DNA and stop reannealing of the oligonucleotides products (or segments) to the template. Analysis of the ligation reaction was then carried out by HPLC.

1.4 Oligonucleotide Assembly and Ligation Method with In-House T4 DNA Ligase Bead Slurry 1.4.1 Bead Slurry Generation T4 ligase (SEQ ID NO:4) fused at the N-terminal to a cellulose binding domain (CBD) was produced using standard cloning, expression and extraction methods. This T4 ligase amino acid sequence differs from the commercial T4 ligase sequence (SEQ ID NO: 3) in that the N-terminal methionine (M) has been replaced with glycine and serine (GS). This was done to aid the generation and expression of the CBD fusion protein. CBD-T4 ligase fusion protein was expressed in BL21 A1 cells (INVITROGEN). Supernatent was harvested and was added to 600 µl of PERLOZA® 100 (PERLOZA®) beads and shaken at 26° C. for 1 hour. The PERLOZAR cellulose beads were then collected and washed with 2 ml buffer (50 mM Tris pH 8.0, 200 mM NaCl, 0.1% TWEEN® 20, 10% Glycerol) followed by 5 ml PBS and were finally re-suspended in 200 µl PBS (10 mM $PO_4^{3-}$, 137 mM NaCl, 2.7 mM KCl pH 7.4). In order to analyse protein expression, 15 µl of the PERLOZAR bead slurry was mixed with 5 µl of SDS loading buffer and incubated at 80° C. for 10 minutes before being run on a SDS PAGE gradient gel (4-20%) according to a standard protocol.

1.4.2 Oligonucleotide Assembly and Ligation Using Bead Slurry

For T4 ligase bound to PERLOZAR beads, the assembly and ligation method in 1.3 above was modified as follows. In the initial segment mixture, 36 µl of H₂O was reduced to 8 µl H₂O. After annealing, 2 µl of commercial T4 DNA ligase was replaced by 20 µl of PERLOZAR bead slurry. Prior to adding the streptavidin magnetic beads, the PERLOZAR beads were spun down and the supernatant removed. The streptavidin magnetic beads were added to the supernatant and incubated at room temperature for 10 minutes to allow the biotinylated template to bind to the streptavidin beads.

1.5 Results and Conclusions

Product, template and all three segment oligonucleotides were clearly resolved in the control chromatogram.

Figure 7:
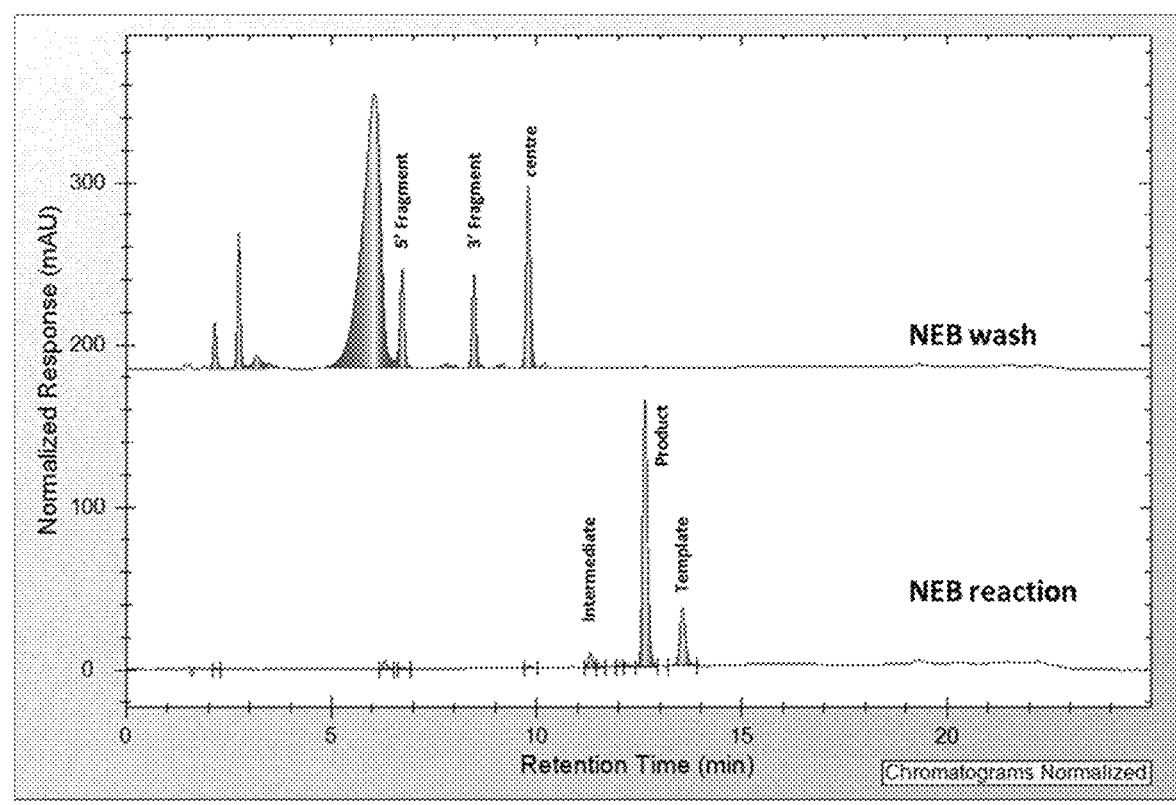
FIG. 7 Chromatogram showing the results of a ligation reaction using commercial NEB T4 ligase (SEQ ID NO:3) and unmodified DNA (Example 1).
Figure 8:
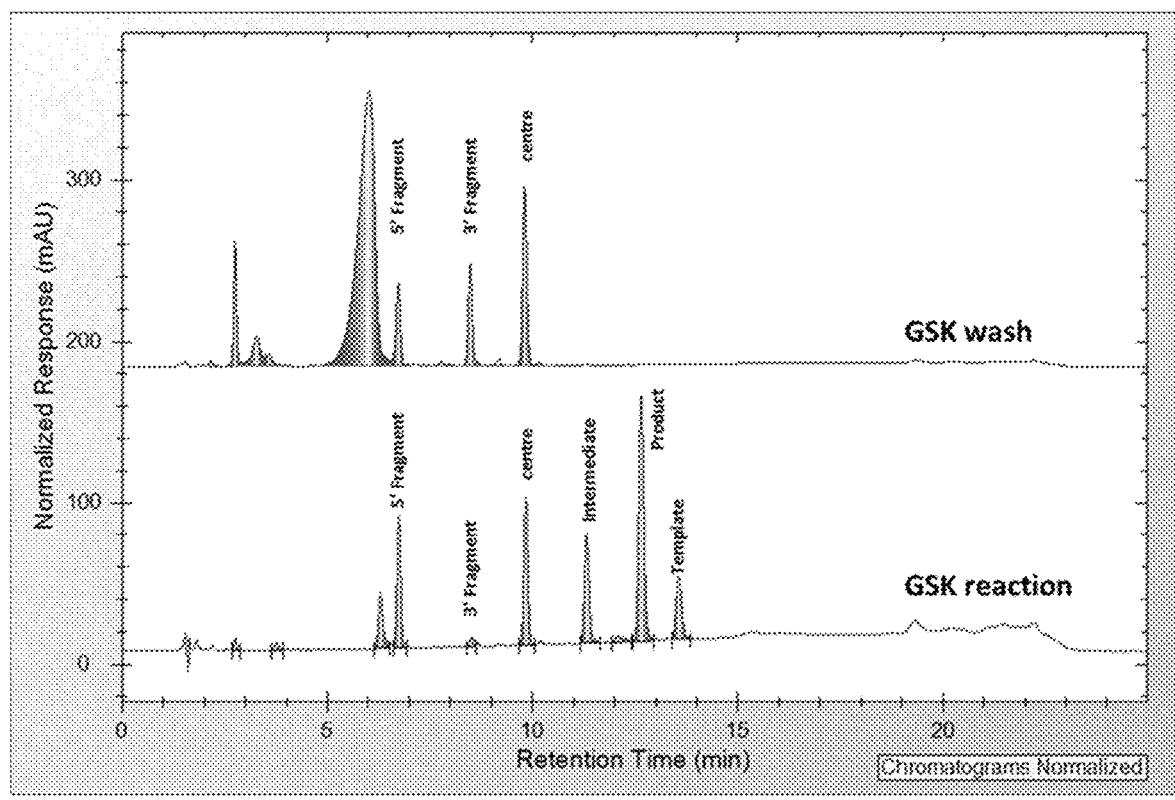
FIG. 8 Chromatogram showing the results of a ligation reaction using PERLOZA® bound T4 ligase (SEQ ID NO:4) and unmodified DNA (Example 1).

HPLC analysis of the ligase reactions showed that some unligated oligonucleotide segments remained, but commercial T4 DNA ligase (NEB) was able to catalyse ligation of the three segments to generate the desired product oligonucleotide (FIG. 7). The PERLOZAR bead bound T4 DNA ligase appeared to be less efficient at ligation of the oligonucleotide segments, with oligonucleotide segments appearing in both the control wash sample and the reaction sample (FIG. 8). However, it is difficult to be sure whether the same amount of enzyme was added on the beads compared to the commercial enzyme and so a direct comparison of ligation efficiency was not possible.

Example 2: 2'-OMe Ribose Modified Oligonucleotide Segment Assembly and Ligation with Wild-Type T4 DNA Ligase 2.1 2' OMe at Each Nucleotide Position in Every Segment In order to determine whether T4 DNA ligase was able to ligate oligonucleotide segments with modification at the 2' position of the ribose ring, oligonucleotide segments were synthesized with the same sequence as for Example 1, but the 2' position of the ribose ring was substituted with an OMe group and thymidine was replaced by uridine as shown below.

TABLE 2

| Name | Sequence | % HPLC purity | Amount (mg) |
|---|---|---|---|
| 5' segment 2'-OMe | 5'-GGC CAA-3' | 21 | 97.8 |
| centre segment 2'-OMe | 5'-(p)ACC UCG GC-3' | 15.5 | 97.7 |
| 3' segment 2'-OMe | 5'-(p)U UAC CU-3' | 21.2 | 98.1 |
| Target 2'-OMe | 5'-GGC CAA ACC UCG GCU UAC CU-3' (SEQ ID NO: 5) | 88 | 96.9 |

(p) = phosphate

Assembly, ligation and HPLC analysis were carried out using the methods of Example 1, with both commercial NEB ligase and T4 ligase CBD fusion bound to PERLOZAR beads. The amount of water used in the reaction mix for the commercial T4 DNA ligase (NEB) experiment was 26 µl rather than 36 µl so that the final reaction volume was 40 µl. The amount of water used in the reaction mix for the in-house T4 DNA ligase bead slurry experiment was 23 µl and the amount of beads used was 5 µl so that the final reaction volume was also 40 µl. Control experiments using unmodified DNA as opposed to 2'-OMe DNA were run in parallel.

The results from the control experiments were in accordance with Example 1. No product was detected using HPLC for the 2'-OMe experiments indicating that T4 DNA ligase is unable to ligate fully 2'-OMe modified oligonucleotide segments regardless of whether a commercial T4 DNA ligase or in-house T4 DNA ligase CBD fusion bound to PERLOZA® beads was used.

2.2 2'-OMe at Each Nucleotide Position in a Single Segment

Using a 1 mg/ml solution of each oligonucleotide the reactions as detailed in Table 3 were set up.

TABLE 3

| Experiment 1 (No ligase control) | Experiment 2 (single 2'-OMe segment - 3') | Experiment 3 (single 2'-OMe segment - 5') | Experiment 4 (all 2'-OMe) | Experiment 5 (all unmodified) | Volume (μl) |
|---|---|---|---|---|---|
| template | template | template | template | template | 2 |
| 5' segment | 5' segment | 2'-OMe substituted 5' segment | 2'-OMe substituted 5' segment | 5' segment | 2 |
| 3' segment | 2'-OMe substituted 3' segment | 3' segment | 2'-OMe substituted 3' segment | 3' segment | 2 |
| Centre segment | Centre segment | Centre segment | 2'-OMe substituted Centre segment | Centre segment | 2 |
| H₂O | H₂O | H₂O | H₂O | H₂O | up to 40 total |

Assembly and ligation were carried out using the methods of Example 1 with commercial NEB ligase and in-house PERLOZA® bound T4 DNA ligase.

Reactions were incubated at 94° C. for 5 minutes, followed by incubation for 5 minutes at 37° C. to allow for annealing. 4 μl of 1×NEB T4 DNA ligation buffer was added to each reaction along with 5 μl (approximately 2 μg) of in-house T4 DNA ligase or 2 μl (approximately 2 μg) commercial T4 DNA ligase (apart from Experiment 1 which was a no ligase control) and the ligation reaction was allowed to proceed for 2 hours at room temperature. Streptavidin magnetic beads were then added to each reaction and the reactions heated to 94° C. before rapid cooling on ice as described in Example 1 to separate the template from starting materials and products.

The processed reactions were split in two: half were analysed by HPLC as described for Example 1 (section 1.2). The other half of the sample was retained for mass spectrometry to confirm the HPLC results.

Figure 9A:
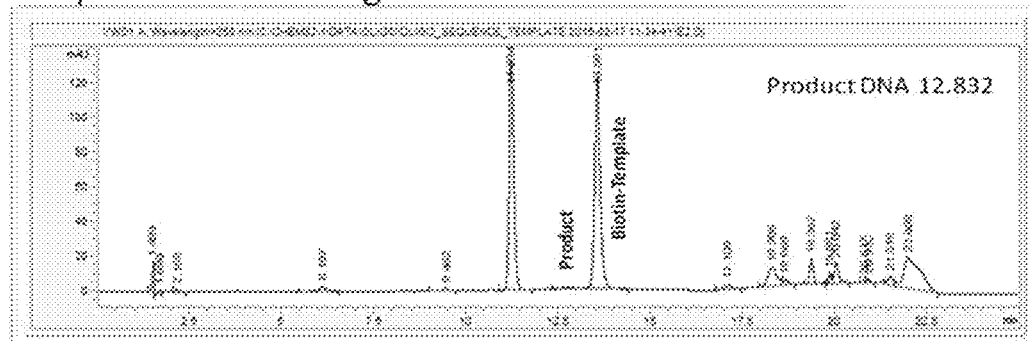
FIG. 9A, FIG. 9B, and FIG. 9C Chromatogram showing the results of a ligation reaction using PERLOZA® bound T4 ligase expressed according to Example 2 and 2'-OMe modified oligonucleotide fragments including the 3' fragment (FIG. 9A), 5' fragment (FIG. 9B), and all fragments (FIG. 9C).
Figure 9B:
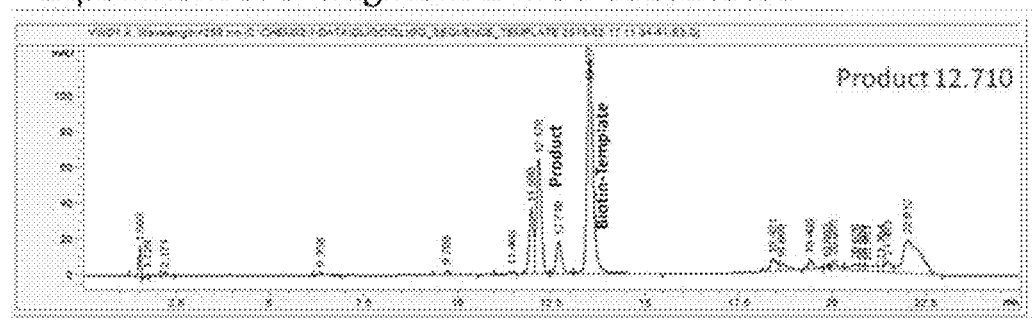
Figure 9C:
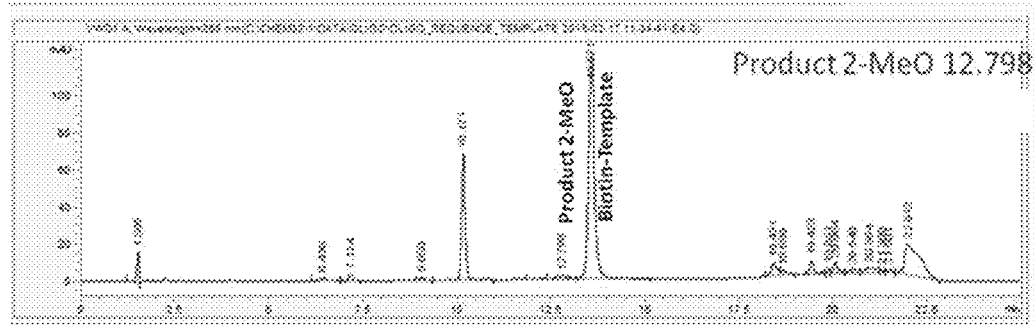
Figure 10A:
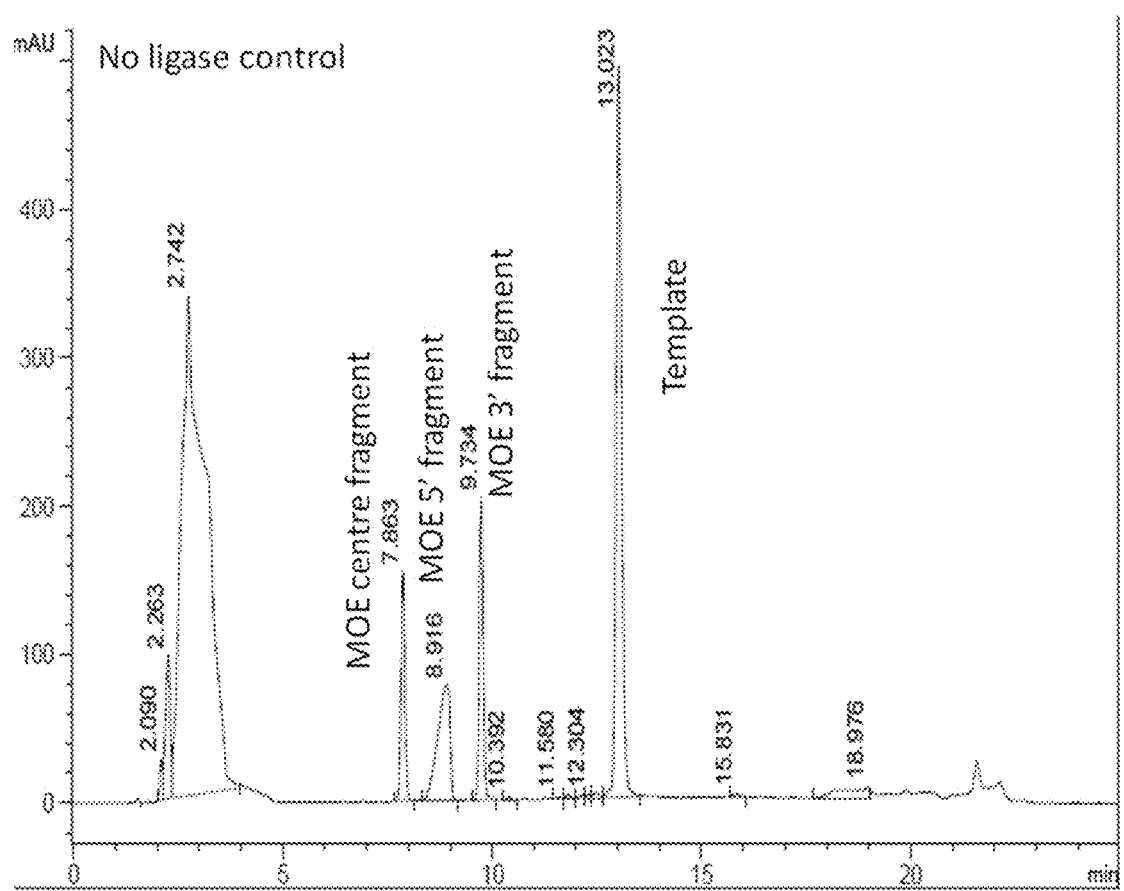
FIG. 10A and FIG. 10B HPLC traces for Example 4: Upper trace (FIG. 10A)—No ligase control. Lower trace (FIG. 10B)—clone A4. Product and template co-elute in this HPLC method. Two intermediate ligation fragments (segments) can be seen in the Clone A4 trace at 10.3 and 11.2 minutes.
Figure 10B:
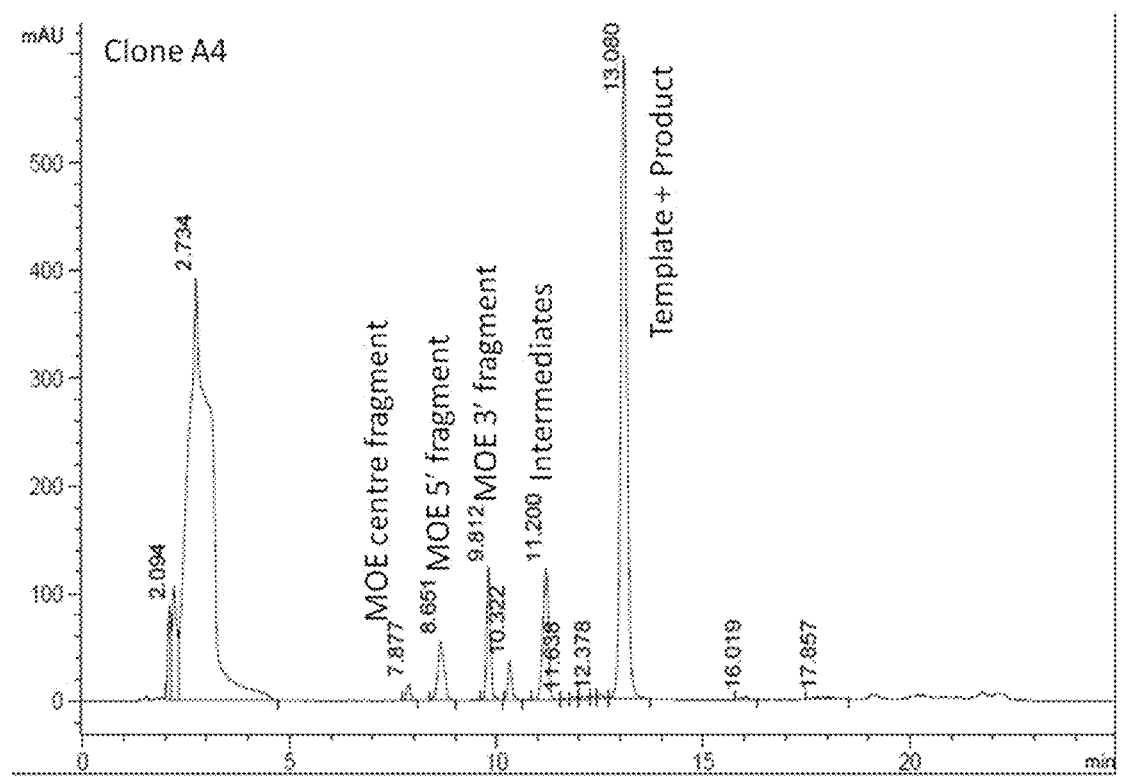

Ligation of unmodified oligonucleotide segments (experiment 5) proceeded as expected to produce full length product. A small amount of ligation was seen when the 5' segment was 2'-OMe substituted (Experiment 3) as shown in FIG. 9, but no ligation was seen when the 3' segment was 2'-OMe substituted (Experiment 2). No significant product was seen when all three segments were 2'-OMe substituted (Experiment 4) in accordance with 2.1.

2.3 Conclusion

Wild-type T4 DNA ligase is poor at ligating 2'-OMe substituted oligonucleotide segments, but slightly less sensitive to modification of the 5' oligonucleotide segment than the 3' segment.

Example 3: 2'-OMe Ribose Modified Oligonucleotide Segment Assembly and Ligation with Wild-Type and Mutant Ligases 3.1 Materials Wild-type Enterobacteria phage ligase CC31 (SEQ ID NO:6), wild-type *Shigella* phage Shf125875 ligase (SEQ ID NO:8), and 10 mutant T4 ligases of SEQ ID NO: 10-19, each fused at the N-terminus to a CBD, were produced using standard cloning, expression and extraction methods. As disclosed in 1.4.1, in order to generate and express the CBD fusion proteins the N-terminal methionine (M) was replaced with glycine and serine (GS) in each case (e.g. SEQ ID NO:7 for Enterobacteria phage ligase CC31 and SEQ ID NO:9 for *Shigella* phage Shf125875 ligase).

The following oligonucleotides were synthesized by standard solid phase methods.

TABLE 4

| Name | Sequence | % HPLC purity | Amount (mg) |
|---|---|---|---|
| 5' segment * | 5'-(OMe)G(OMe)G(OMe)C(OMe)C(OMe)AA-3' | 99.35 | 24.7 |
| centre segment | 5'-(p)ACC TCG GC-3' | 96.9 | 58.1 |
| 3' segment | 5'-(p)TTA CCT-3' | 97.88 | 29.5 |
| Biotinylated template | 5'-biotin TT TAG GTA AGC CGA GGT TTG GCC-3' (SEQ ID NO: 2) | 96.9 | 130.7 |

N.B. OMe indicates 2' methoxy substitution on the ribose ring
(p) = phosphate
* note that the first 5 nucleotides are 2'-OMe modified (GGCCA), but the final A is not 3.2 Oligonucleotide Assembly and Ligation Method with Ligase Bead Slurries 3.2.1 Bead Slurry Generation Ligases fused to CBD were bound to PERLOZA® beads as described in 1.4 to generate a bead slurry.

3.2.2 Oligonucleotide Assembly and Ligation Using Bead Slurry

Ligation reactions were prepared with the components below to a final volume of 50 μL in a 96 well plate:

| | |
|---|---|
| 2 µL | ~1 mg/mL 5' (2'-OMe) segment |
| 2 µL | ~1 mg/mL centre segment |
| 2 µL | ~1 mg/mL 3' segment |
| 2 µL | ~1 mg/mL template |
| 5 µL | NEB T4 DNA ligase buffer |
| 22 µL | H₂O |
| 15 µL | PERLOZA bound bead slurry |

The reaction was incubated for 15 minutes at room temperature prior to the addition of PERLOZA® bead slurry to allow segments to anneal to the template. PERLOZA® bead slurry was added and the reaction incubated at room temperature for 1 hour. After the hour incubation, the solution was transferred into an ACOPREP advance 350 filter plate (PN 8082) and the filter plate was placed on top of an ABGENE superplate (Thermo Scientific, #AB-2800) and centrifuged for 10 minutes at 4,000 rpm to remove the PERLOZAR bead slurry. Solutions were then analysed by HPLC using the method described in Example 1 (section 1.2).

Each oligonucleotide assembly and ligation was repeated 6 times for each ligase.

3.3 Results and Conclusions

Wild-type Enterobacteria phage CC31 ligase (SEQ ID NO:6) and wild-type *Shigella* phage Shf125875 ligase (SEQ ID NO:8) are able to ligate a 2' OMe substituted 5' segment containing five 2'-OMe nucleobases and one deoxynucleobase to a segment containing only unmodified DNA. In addition, whilst wild-type T4 DNA ligase (SEQ ID NO: 3 and 4) is poor at performing this reaction, as shown in Example 2 and reconfirmed here, a number of mutations at positions 368 and 371 confer the ability to ligate a 2'-OMe substituted 5' segment containing five 2' OMe nucleobases and one deoxynucleobase to a segment containing only unmodified DNA on the ligase (SEQ ID NO: 10-19).

Example 4: 2' MOE Ribose Modified and 5-Methyl Pyrimidine Modified Oligonucleotide Segment Assembly and Ligation with Mutant DNA Ligases 4.1 Materials Modified oligonucleotide segments as set out in Table 5 below were synthesised by standard solid phase based methods.

TABLE 5

| Segment | Sequence | MW | Mass (mg) | % purity |
|---|---|---|---|---|
| centre segment | 5'-(p)dCdCdTdCdGdG-3' | 2044.122 | 39 | 98.96 |
| MOE 3'-segment | 5'-(p)dCdTmTmAmCmCmT-3' | 2699.679 | 52 | 97.79 |
| MOE 5'-segment | 5'-mGmGmCmCmAdAdA-3' | 2644.771 | 48 | 99.13 |

(p) = phosphate, mX = MOE bases, dX = DNA bases all 5-methyl pyrimidines

Mutant DNA ligases (SEQ ID NO:20-28) based upon wild type Enterobacteria phage CC31 ligase, wild type T4 ligase and wild type *Shigella* phage Shf125875 ligase were each fused at the N-terminus to a cellulose binding domain (CBD), using standard cloning, expression and extraction methods. Ligases fused to CBD were bound to PERLOZA® beads as described in 1.4 to generate a bead slurry. In order to release the ligases from the PERLOZAR beads, 2 µl of TEV protease was added to the slurry and incubated overnight at 4° C. The cleaved protein, now lacking the cellulose binding domain, was collected by centrifugation for 10 min at 4000 rpm.

4.2 Method

The reaction was set up as follows:

| | |
|---|---|
| centre segment | 20 µM final |
| MOE 3' segment | 20 µM final |
| MOE 5' segment | 20 µM final |
| Template | 20 µM final |
| NEB T4 DNA ligase buffer | 5 µl |
| mutant DNA ligase | 15 µl |
| H₂O | To make final reaction volume 50 µl |

All components were mixed and vortexed prior to addition of DNA ligase. Reactions were incubated for 1 hour at 35° C. After 1 hour reactions were stopped by heating at 95° C. for 5 minutes in a PCR block.

Samples were analysed by both HPLC and LCMS to confirm product identity according to the HPLC protocol used in Example 1 (section 1.2). Controls of commercial NEB T4 DNA ligase and a negative control (H₂O instead of any ligase) were included.

4.3 Results and Conclusions

FIG. 10A, FIG. 10B, FIG. 10C and FIG. 10D shows the HPLC traces for the control reaction and the reaction catalysed by SEQ ID NO:23 (clone A4-mutant Enterobacteria phage CC31 ligase). The product and template co-elute using this HPLC method so product appears as an increase in the peak area of the product+template peak. In the mutant ligase trace (b) not only does the product+template peak increase but two new peaks appear at 10.3 and 11.2 minutes. These peaks correspond to the ligation of the centre segment with either the MOE 5' segment or the MOE 3' segment. Also, the input segment peaks are substantially smaller than the control in line with product and intermediate peaks increasing. The NEB commercial T4 ligase trace (a) showed a slight increase in the peak area for template+product, a small amount of intermediate ligation product along with a concomitant decrease in input oligonucleotide segments. The mutant ligase (SEQ ID NO:23), however, showed substantially greater product+template peak area and concomitant reduction in peak areas for input oligonucleotide segments. Thus the mutant ligase (SEQ ID NO:23) is a much more effective ligase for the 2' MOE substituted segments than commercial T4 DNA ligase. Similar improvements were shown for the other mutant ligases (SEQ ID NO:20, 21, 24-28).

Example 5: Effect of Different Nucleotide Pairing at the Ligation Site

5.1 Materials

Mutant Enterobacteria phage CC31 ligase (SEQ ID NO:23) fused at the N-terminal to a cellulose binding domain (CBD) was produced using standard cloning, expression and extraction methods. Extracted CBD-mutant Enterobacteria phage CC31 ligase fusion protein was added to 25 ml of PERLOZAR 100 (PERLOZA®) cellulose beads and shaken at 20° C. for 1 hour. The PERLOZAR beads were then collected and washed with 250 ml buffer (50 mM Tris pH 8.0, 200 mM NaCl, 0.1% TWEEN® 20, 10% Glycerol) followed by 250 ml PBS and were finally re-suspended in 10 ml PBS (10 mM $PO_4^{3-}$, 137 mM NaCl, 2.7 mM KCl pH 7.4). In order to analyse protein expression, 15 µl of the PERLOZA® bead slurry was mixed with 5 µl of SDS loading buffer and incubated at 80° C. for 10 minutes before being run on a SDS PAGE gradient gel (4-20%) according to a standard protocol. For the release of the ligase from the beads, 70 µl of TEV protease was added and incubated overnight at 4° C. with shaking. Ligase was collected by washing the digested beads with 80 ml of PBS. The ligase was then concentrated down to 1.2 ml using an Amicon 30 Kd MCO filter.

The following biotinylated DNA template oligonucleotides (Table 6) and DNA segment oligonucleotides (Table 7) were synthesized by standard solid phase methods. Please note that the nucleotides in bold are the ones present at the ligation site (i.e. those nucleotides that were joined together in the ligation reaction-table 7; and those nucleotides that are complementary to those joined via the ligation reaction-table 6).

TABLE 6

| Template number | Sequence (nucleotides complementary to junction nucleotides are in bold) | SEQ ID NO |
|---|---|---|
| 1 | 5'-biotin TTTGGTGCGAAGCAGACTGAGGC-3' | 30 |
| 2 | 5'-biotin TTTGGTGCGAAGCAGAGTGAGGC-3' | 31 |
| 3 | 5'-biotin TTTGGTGCGAAGCAGATTGAGGC-3' | 32 |
| 4 | 5'-biotin TTTGGTGCGAAGCAGAATGAGGC-3' | 33 |
| 5 | 5'-biotin TTTGGTGCGAAGCAGTCTGAGGC-3' | 34 |
| 6 | 5'-biotin TTTGGTGCGAAGCAGTGTGAGGC-3' | 35 |
| 7 | 5'-biotin TTTGGTGCGAAGCAGTTTGAGGC-3' | 36 |
| 8 | 5'-biotin TTTGGTGCGAAGCAGTATGAGGC-3' | 37 |
| 9 | 5'-biotin TTTGGTGCGAAGCAGCCTGAGGC-3' | 38 |
| 10 | 5'-biotin TTTGGTGCGAAGCAGCGTGAGGC-3' | 39 |
| 11 | 5'-biotin TTTGGTGCGAAGCAGCTTGAGGC-3' | 40 |
| 12 | 5'-biotin TTTGGTGCGAAGCAGCATGAGGC-3' | 41 |
| 13 | 5'-biotin TTTGGTGCGAAGCAGGCTGAGGC-3' | 42 |
| 14 | 5'-biotin TTTGGTGCGAAGCAGGGTGAGGC-3' | 43 |
| 15 | 5'-biotin TTTGGTGCGAAGCAGGTTGAGGC-3' | 44 |
| 16 | 5'-biotin TTTGGTGCGAAGCAGGATGAGGC-3' | 45 |

TABLE 7

| Segment | Identifier | Sequence (junction nucleotides are in bold) |
|---|---|---|
| 5' | A | 5'-GCCTCAG-3' |
| 5' | B | 5'-GCCTCAC-3' |
| 5' | C | 5'-GCCTCAA-3' |
| 5' | D | 5'-GCCTCAT-3' |
| 3' | E | 5'-(p)TCTGCT-3' |
| 3' | F | 5'-(p)ACTGCT-3' |
| 3' | G | 5'-(p)CCTGCT-3' |
| 3' | H | 5'-(p)GCTGCT-3' |

(p) = phosphate

N.B. please note that, unlike previous examples, the ligation reactions in this example involve joining two segments together: a 5'-segment and a 3'-segment, i.e. there is no centre segment.

5.2 Method

Reactions were set up as follows:

TABLE 8

| Template | 5'-segment | 3'-segment |
|---|---|---|
| 1 | A | E |
| 2 | B | E |
| 3 | C | E |
| 4 | D | E |
| 5 | A | F |
| 6 | B | F |
| 7 | C | F |
| 8 | D | F |
| 9 | A | H |
| 10 | B | H |
| 11 | C | H |
| 12 | D | H |
| 13 | A | G |
| 14 | B | G |
| 15 | C | G |
| 16 | D | G |

For each 50 µL reaction:

| | |
|---|---|
| 3' segment (1 mM stock, 20 µM final) | 1 µl |
| 5' segment (1 mM stock, 20 µM final) | 1 µl |

| | |
|---|---|
| Template (1 mM stock, 20 μM final) | 1 μl |
| NEB DNA ligase buffer (for T4 ligase) | 5 μl |
| Mutant CC31 DNA ligase (0.45 mM stock, 90 μM final) | 10 μl |
| H$_2$O | up to 50 μl |

Each reaction mix was incubated at 35° C. both for 30 minutes and 1 hour. Each reaction was terminated by heating at 95° C. for 5 minutes. HPLC analysis was carried out.

5.3 Results and Conclusions

All of the reactions produced a product peak after 1 hour incubation in HPLC analysis. Accordingly, the ligation method works for all combinations of nucleotides at the junctions to be joined. Optimisation to improve product yield is possible, but was not necessary as the results were conclusive and it was clear that the reaction was working for all combinations of nucleotides at the junctions to be joined.

Example 6: Effect of Different Modifications at the Ligation Site 6.1 Materials

Mutant Enterobacteria phage CC31 ligase (SEQ ID NO:23) was produced as described in 5.1 and *Chlorella* virus DNA ligase (SEQ ID NO:29, commercially available as SPLINTR® ligase, NEB) was purchased.

The following biotinylated template oligonucleotide and segment oligonucleotides (Table 9) were synthesized by standard solid phase methods.

TABLE 9

| Name | Sequence (junction modification in bold) |
|---|---|
| Template | 5'-biotin TTTAGGTAAGCCGAGGTTTGGCC-3' (SEQ ID NO: 2) |
| 5' segment (WT) | 5'-GGCCAAA-3' |
| 5' segment (Mo1) | 5'-GGCCAA(OMe)A-3' |
| 5' segment (Mo2) | 5'-GGCCAA(F)A-3' |
| centre segment (WT) | 5'-(p)CCTCGG-3' |
| centre segment (Mo4A) | 5'-(p)(OMe)CCTCGG-3' |
| centre segment (Mo5A) | 5'-(p)(F)CCTCGG-3' |
| centre segment (Mo7) | 5'(p)(Me)CCTCGG-3' |
| 3' segment (WT) | 5'-(p)CTTACCT-3' |
| 3' segment (Mo8) | 5'-(p)(Me)CTTACCT3' |

OMe indicates 2' methoxy substitution on the ribose ring
F indicates 2' fluoro substitution on the ribose ring
All remaining sugar residues are deoxyribose residues
Me indicates 5-methyl cytosines 6.2 Method Reactions were set up as follows:

TABLE 10

| Reaction | 5' segment | Centre segment | 3' segment |
|---|---|---|---|
| 1 | WT | WT | WT |
| 2 | WT | Mo4A | WT |
| 3 | WT | Mo5A | WT |
| 4 | WT | Mo7 | WT |
| 5 | Mo1 | WT | WT |
| 6 | Mo1 | Mo4A | WT |
| 7 | Mo1 | Mo5A | WT |
| 8 | Mo1 | Mo7 | WT |
| 9 | Mo2 | WT | WT |
| 10 | Mo2 | Mo4A | WT |
| 11 | Mo2 | Mo5A | WT |
| 12 | Mo2 | Mo7 | WT |
| 13 | WT | WT | Mo8 |
| 14 | WT | Mo4A | Mo8 |
| 15 | WT | Mo5A | Mo8 |
| 16 | WT | Mo7 | Mo8 |
| 17 | Mo1 | WT | Mo8 |
| 18 | Mo1 | Mo4A | Mo8 |
| 19 | Mo1 | Mo5A | Mo8 |
| 20 | Mo1 | Mo7 | Mo8 |
| 21 | Mo2 | WT | Mo8 |
| 22 | Mo2 | Mo4A | Mo8 |
| 23 | Mo2 | Mo5A | Mo8 |
| 24 | Mo2 | Mo7 | Mo8 |

For each 50 μL reaction:

| | |
|---|---|
| 3'-segment (1 mM, stock, 20 μM final) | 1 μl |
| centre segment (1 mM, stock, 20 μM final) | 1 μl |
| 5'-segment (1 mM, stock, 20 μM final) | 1 μl |
| Template (1 mM, stock, 20 μM final) | 1 μl |
| H$_2$O | up to 50 μl |

For Mutant Enterobacteria phage CC31 ligase (SEQ ID NO:23)

| | |
|---|---|
| DNA ligase buffer (50 mM Tris-HCl, 1 mM DTT) | 5 μl |
| Mutant CC31 DNA ligase (0.45 mM) | 10 μl |
| MnCl$_2$ (50 mM) | 5 μl |
| ATP (10 mM) | 10 μl |

Whereas for *Chlorella* virus DNA ligase (SEQ ID NO:29, commercially available as SPLINTR® ligase, NEB)

| NEB DNA ligase buffer (for Chlorella) | 5 μl |
|---|---|
| Chlorella virus DNA ligase | 2 μl |

Each reaction mix was incubated at 20° C. 1 hour. Each reaction was terminated by heating at 95° C. for 10 minutes. HPLC analysis was carried out using the method of Example 1.

6.3 Results and Conclusions

All of the reactions produced a product peak in HPLC analysis. Accordingly, the ligation method works for all combinations of modifications tested at the junctions to be joined. Optimisation to improve product yield is possible, but was not necessary as the results were conclusive and it was clear that the reaction was working for all combinations of modifications tested at the junctions to be joined.

Example 7: Ability to Use Different Numbers of Segments to Build Larger Oligonucleotides 7.1 Materials Mutant Enterobacteria phage CC31 ligase (SEQ ID NO:23) was produced as described in 5.1.

The following biotinylated template DNA oligonucleotides and DNA segment oligonucleotides (Table 11) were synthesized by standard solid phase methods.

TABLE 11

| Name | Sequence |
|---|---|
| Template | 5'-biotin TTTGGTGCGAAGCAGAAGGTAAGCCGAGGT TTGGCC-3' (SEQ ID NO: 47) |
| 5' segment (1) | 5'-GGCCAAA-3' |
| centre segment (2) | 5'-(p)CCTCGG-3' |
| centre segment/ 3' segment (5) | 5'-(p)TCTGCT-3' |
| centre segment (3) | 5'-(p)CTTACCT-3' |
| 3' segment (4) | 5'-(p)TCGCACC-3' |

(p) = phosphate, 7.2 Method

Reactions were set up as follows:

TABLE 12

| 5' segment | Centre segment(s) | 3' segment | Total number of segments |
|---|---|---|---|
| 1 | 2 and 3 | 5 | 4 |
| 1 | 2, 3 and 5 | 4 | 5 |

Reactions were run in phosphate buffered saline, pH=7.04 in a total volume of 100 μl and set up as follows:—
Template (20 μM final)
Each segment (20 μM final)
MgCl$_2$ (10 mM final)
ATP (100 μM final)
Mutant CC31 DNA ligase (25 μM final)

Each reaction was incubated at 28° C. overnight before being terminated by heating at 94° C. for 1 minute. Products were analysed by HPLC mass spec.

7.3 Results and Conclusions

The reaction using 4 segments produced a fully ligated product of 27 base pairs in length. The reaction using 5 segments produced a product of 33 base pairs in length. In both cases the observed mass of the product was in concordance with that expected for the desired sequence. In conclusion, it is clearly possible to assemble multiple segments to generate oligonucleotides of the desired length and sequence as defined by the appropriate complementary template sequence.

Example 8: Assembly and Ligation of 5-10-5 Segments to Form a Gapmer, Wherein the 5' and the 3' Segments Comprise (i) 2'-OMe Ribose Sugar Modifications, (ii) Phosphorothioate Linkages or (iii) 2'-OMe Ribose Sugar Modifications and Phosphorothioate Linkages; and Wherein the Central Segment is Unmodified DNA 8.1 Materials Mutant Enterobacteria phage CC31 ligase (SEQ ID NO:23) was produced as described in 5.1 the following biotinylated template DNA oligonucleotide and segment oligonucleotides (Table 13) were synthesized by standard solid phase methods.

TABLE 13

| Name | Sequence |
|---|---|
| Template | 5'-biotin TTTGGTGCGAAGCAGACTGAGGC-3' (SEQ ID NO: 30) |
| 3' segment (3OMe) | 5'-(p)(OMe)G(OMe)C(OMe)C(OMe)T(OMe)C-3' |
| 3' segment (3PS + OMe) | 5'-(p)(OMe)G*(OMe)C*(OMe)C*(OMe)T*(OMe)C-3' |
| 3' segment (3PS) | 5'-(p)G*C*C*T*C-3' |
| centre segment (D) | 5'-(p)AGTCTGCTTC-3' |
| 5' segment (5OMe) | 5'-(OMe)G(OMe)C(OMe)A(OMe)C(OMe)C-3' |

TABLE 13-continued

| Name | Sequence |
|---|---|
| 5' segment (5PS + OMe) | 5'-(OMe)G*(OMe)C*(OMe)A*(OMe)C*(OMe)C-3' |
| 5' segment (5PS) | 5'-G*C*A*C*C-3' |

OMe indicates 2' methoxy substitution on the ribose ring
All remaining sugar residues are deoxyribose residues
*phosphorothioate 8.2 Method
Reactions were set up as follows:

TABLE 14

| Reaction | 3' segment | Centre segment(s) | 5' segment |
|---|---|---|---|
| 1 | 3PS | D | 5PS |
| 2 | 3OMe | D | 5OMe |
| 3 | 3PS + OMe | D | 5PS + OMe |

Each of reactions 1, 2 and 3 were set up in 100 μl final volume in phosphate buffered saline with the following components:—

| | |
|---|---|
| 3' segment | 20 μM final |
| Centre segment | 20 μM final |
| 5' segment | 20 μM final |
| Template | 20 μM final |
| $MgCl_2$ | 10 mM final |
| ATP | 50 μM final |
| Enzyme | 25 μM final |

Each reaction mix was incubated at 20° C. overnight. Each reaction was terminated by heating at 95° C. for 10 minutes. HPLC mass spec analysis was carried out.

8.3 Results and Conclusions

Product oligonucleotide corresponding to the successful ligation of all three fragments was produced in all three reactions.

Accordingly, mutant Enterobacteria phage CC31 ligase (SEQ ID NO:23) is able to ligate 3 segments together to form a 'gapmer' where the 5' and 3' 'wings' have a phosphorothioate backbone, whereas the central region has a phosphodiester backbone, and all the sugar residues in the gapmer are deoxyribose residues. Enterobacteria phage CC31 ligase (SEQ ID NO:23) is also able to ligate 3 segments together to form a 'gapmer' where the 5' and 3' 'wings' have 2'-methoxyribose (2'-OMe) residues, whereas the central region has deoxyribose residues, and all of the linkages are phosphodiester linkages. Finally, Enterobacteria phage CC31 ligase (SEQ ID NO:23) is able to ligate 3 segments together to form a 'gapmer' where the 5' and 3' 'wings' have the combined modifications (a phosphorothioate backbone and 2'-methoxyribose residues), whereas the central region has deoxyribose residues and phosphodiester linkages.

Example 9: Assembly and Ligation of Segments Comprising Locked Nucleic Acids (LNA)

9.1 Materials

Mutant Enterobacteria phage CC31 ligase (SEQ ID NO:23) was produced as described in 5.1. A mutant *Staphylococcus aureus* NAD dependent ligase (NAD-14) was produced as described in 13.1

The following biotinylated template DNA oligonucleotide and segment oligonucleotides (Table 15) were synthesized by standard solid phase methods.

TABLE 15

| Name | Sequence |
|---|---|
| Template | 5'-biotin TTTGGTGCGAAGCAGACTGAGGC-3' (SEQ ID NO: 30) |
| 5'-segment | 5'-GCCTCAG-3' |
| LNA 5'-segment (oligo 1) | 5'-GCCTCA(LNA)G-3' |
| Centre segment | 5'-(p)TCTGCT-3' |
| LNA centre segment (oligo 2) | 5'-(p)(LNA)TCTGCT-3' |

(p) = phosphate
LNA = locked nucleic acid 9.2 Method

Reactions were set up as follows:

| Reaction volume 100 μL | |
|---|---|
| Template | 20 μM final |
| Enzyme | 25 μM final |
| All oligonucleotide segments | 20 μM final |

Reactions were set up varying enzyme (mutant Enterobacteria phage CC31 ligase (SEQ ID NO: 23) or NAD-14), divalent cation ($Mg^{2+}$ or $Mn^{2+}$) and combinations of oligonucleotide segments as set out in Table 16.

TABLE 16

| Enzyme | SEQ ID NO: 23 | SEQ ID NO: 23 | NAD-14 | NAD-14 |
|---|---|---|---|---|
| Divalent cation | 10 mM $MgCl_2$ | 10 mM $MnCl_2$ | 10 mM $MgCl_2$ | 10 mM $MnCl_2$ |
| Cofactor | 100 µM ATP | 100 µM ATP | 100 µM NAD | 100 µM NAD |
| Buffer | PBS, pH = 7.04 | PBS, pH = 7.04 | 50 mM $KH_2PO_4$, pH 7.5 | 50 mM $KH_2PO_4$, pH 7.5 |
| 5' segment + Centre segment | Product | Product | Product | Product |
| Oligo 1 + Centre segment | Product | Product | Product | Product |
| 5' segment + Oligo 2 | Product | Product | Product | Product |
| Oligo 1 + oligo 2 | No product | No product | No product | No product |

Each reaction mix was incubated at 28° C. overnight. Each reaction was terminated by heating at 94° C. for 1 minute. HPLC mass spec. analysis was carried out.

9.3 Results and Conclusions

Product oligonucleotide was produced in control reaction reactions (unmodified oligonucleotides only) and where a single locked nucleic acid was included in one segment at the ligation junction regardless of whether it was on the 3' or 5' side of the junction. When locked nucleic acids were included at both sides (oligo 1+oligo 2) no product was detected. The data was similar for both enzymes and regardless of whether Mg2+ or Mn2+ were used.

Enzyme mutations and/or selection screens could be carried out to identify an enzyme capable of ligating segments with a locked nucleic acid at both the 3' and 5' side of the junction.

Example 10: Assembly and Ligation of Three Segments (7-6-7) to Form a Gapmer Wherein the 5' and the 3' Segments Comprise 2' MOE Ribose Sugar Modifications and all Linkages are Phosphorothioate Linkages, Using a Variant of Enterobacteria Phage CC31 Ligase in the Presence of $Mg^{2+}$ or $Mn^{2+}$ 10.1 Phosphorothioate bond formation In order to determine whether a mutant Enterobacteria phage CC31 ligase (SEQ ID NO: 23) was able to ligate modified oligonucleotide segments with a phosphorothioate backbone, 2' MOE ribose sugar modifications and 5-methylated pyrimidine bases, reactions were performed using the oligonucleotide segments shown in table 15. Reactions were performed in the presence of $Mg^{2+}$ and $Mn^{2+}$ ions.

10.2 Materials

Oligonucleotides were chemically synthesised using standard methods as shown below:

TABLE 17

| Name | Sequence |
|---|---|
| 5' segment 2'-MOE PS | 5'-mG*mG*mC*mC*mA*dA*dA-3' |
| centre segment PS | 5'-(p)*dC*dC*dT*dC*dG*dG -3' |
| 3' segment 2'-MOE PS | 5'-(p)*dC*dT*mU*mA*mC*mC*mU-3' |

TABLE 17-continued

| Name | Sequence |
|---|---|
| Biotinylated template | 5'-biotin dT dT dT dA dG dG dT dA dA dG dC dC dG dA dG dG dT dT dT dG dG dC dC-3' (SEQ ID NO: 2) |

(p)* = 5'-phosphorothioate, * = phosphorothioate linkage, mX = MOE bases, dX = DNA bases
all segments and product have 5-methyl pyrimidines (with the exception of the template)
mT and m (Me)U are considered to be equivalent
N.B. the target 2'MOE PS molecule produced by ligation of the segments in table 17, when hybridised to the biotinylated template shown in table 17, is:
5'-mG*mG*mC*mC*mA*dA*dC*dC*dT*dC*dG*dG*dC*dT*mU*mA*mC*mC*mU-3' (SEQ ID NO: 1)
Purified mutant Enterobacteria phage CC31 ligase (SEQ ID NO: 23) was prepared as described in example 5.1. HPLC analysis was carried out.

10.3 Oligonucleotide Assembly and Ligation Method with Enterobacteria Phage CC31 Ligase Variant (SEQ ID NO:23)

Reactions were prepared as follows:

| $MgCl_2$ reaction | |
|---|---|
| 10 x T4 DNA ligase buffer (NEB)* | 5 µl |
| template | 20 µM final concentration |
| 5' segment 2' MOE PS | 20 µM final concentration |
| centre segment PS | 20 µM final concentration |
| 3' segment 2' MOE PS | 20 µM final concentration |
| ligase (24.3 µM) | 10 µl |
| water | made up to 50 µL |

*1 x buffer contains 50 mM Tris-HCl, 10 mM $MgCl_2$, 1 mM ATP, 10 mM DTT, pH 7.5

| $MnCl_2$ reaction | |
|---|---|
| 10 x ligase buffer* | 5 µl |
| ATP (10 mM) | 5 µl |
| $MnCl_2$ (50 mM) | 5 µl |
| template | 20 µM final concentration |
| 5' segment 2' MOE PS | 20 µM final concentration |
| centre segment PS | 20 µM final concentration |
| 3' segment 2' MOE PS | 20 µM final concentration |
| ligase (24.3 µM) | 10 µl |
| water | made up to 50 µL |

*1 x buffer contains 50 mM Tris-HCl, 10 mM DTT, pH 7.5

The final reactions contained 20 µM of each segment and template, 5 mM $MgCl_2$ or 5 mM $MnCl_2$, 1 mM ATP, 50 mM Tris-HCl, 10 mM DTT, pH 7.5 and 4.9 µM ligase. Additional reactions were prepared containing no enzyme and served as a negative control. Reactions were incubated for 16 hours at 25° C. and then quenched by heating to 95° C. for 5 minutes. Precipitated proteins were cleared by centrifugation and samples were analysed by HPLC.

10.4 Results and Conclusion

Product, template and segment oligonucleotides were clearly resolved in the control chromatogram and no ligation was observed. Ligase reactions performed in the presence of 5 mM $MgCl_2$ led to the formation of an intermediate product formed from the ligation of the 5' segment and centre segments, but no full length product was detected.

Ligase reactions performed in the presence of $MnCl_2$ produced both full length product and intermediate (5' segment plus centre segment intermediate). Both ligase reactions showed that unligated oligonucleotide segments remained. However, optimisation of the protocol is possible in order to maximise product yield.

Example 11: Assembly and Ligation of Three Segments (7-6-7) to Form a Gapmer Wherein the 5' and the 3' Segments Comprise 2' MOE Ribose Sugar Modifications and all Linkages are Phosphorothioate Linkages, Using Wild-Type *Chlorella* Virus DNA Ligase in the Presence of Native $Mg^{2+}$

11.1 Materials

In order to determine whether *Chlorella* virus DNA ligase (SEQ ID NO:29, commercially available as SPLINTR® ligase, NEB) was able to ligate modified oligonucleotide segments with a phosphorothioate backbone, 2' MOE ribose sugar modifications and 5-methylated pyrimidine bases reactions were performed using the oligonucleotide segments shown in example 10.2 table 17. Reactions were performed at 25° C., 30° C. and 37° C. to investigate the effect of temperature on the enzyme activity.

11.2 Oligonucleotide Assembly and Ligation Method with Commercial *Chlorella* Virus DNA Ligase (SEQ ID NO:29)

Each Oligonucleotide segment and template were dissolved in nuclease free water as detailed below:

| | |
|---|---|
| Biotinylated template | 249.6 ng/µl |
| 5' segment 2' MOE PS | 182.0 ng/µl |
| Centre segment PS | 534.0 ng/µl |
| 3' segment 2' MOE PS | 531.0 ng/µl |

Reactions were prepared as follows:

| | |
|---|---|
| 10 x buffer (NEB)* | 6 µl |
| template | 3.8 µl |
| 5' segment 2' MOE PS | 18.1 µl |
| centre segment PS | 4.8 µl |
| 3' segment 2' MOE PS | 6.3 µl |
| water | 15 µl |
| SplintR ligase (25 U/µl) | 6 µl |

*1 x buffer contains 50 mM Tris-HCl, 10 mM MgCl$_2$, 1 mM ATP, 10 mM DTT, pH 7.5

The final reactions contained 20 µM of each segment and template, 50 mM Tris-HCl, 10 mM MgCl$_2$, 1 mM ATP, 10 mM DTT, pH 7.5 and 2.5 U/µl ligase. Reactions were incubated at 25° C., 30° C. and 37° C. Additional reactions were prepared containing no enzyme and served as a negative control. Following 16 hours incubation, reactions were quenched by heating to 95° C. for 10 minutes. Precipitated proteins were cleared by centrifugation and samples were analysed by HPLC.

11.3 Results and Conclusion

Product, template and segment oligonucleotides were clearly resolved in the control chromatogram and no ligation was observed. HPLC analysis of the ligase reactions showed that unligated oligonucleotide segments remained, but *Chlorella* virus DNA ligase was able to successfully ligate the segments. The activity of the ligase increased with increasing temperature. At 25° C. the *Chlorella* virus DNA ligase was able to successfully ligate the 5' segment and centre segment but no full length product was observed. At 30° C. and 37° C., full length product was detected in addition to the intermediate formed from 5' segment and centre segment.

Example 12: Screening a Panel of 15 ATP and NAD Ligases for Activity Towards the Ligation of Three Segments (7-6-7) to Form a Gapmer Wherein the 5' and the 3' Segments Comprise 2' MOE Ribose Sugar Modifications and all Linkages are Phosphorothioate Linkages

12.1 Materials

Wild-type ATP and NAD dependent ligases described in table 18 and 19 were each fused at the N-terminus to a CBD. Genes were synthesised, cloned into pET28a and expressed in *E. coli* BL21 (DE3) using standard cloning, expression and extraction methods.

TABLE 18

ATP dependent Ligases

| Name | Origin | SEQ ID |
|---|---|---|
| M1I5D1_Pbcv | *Paramecium bursaria* Chlorella virus NE-JV-4 | SEQ ID NO: 48 |
| M1I998_Pbcv | *Paramecium bursaria* Chlorella virus NYs1 | SEQ ID NO: 49 |
| M1HX09_Pbcv | *Paramecium bursaria* Chlorella virus NE-JV-1 | SEQ ID NO: 50 |
| M1HUL0_Atcv | *Acanthocystis turfacea* Chlorella virus Canal-1 | SEQ ID NO: 51 |
| M1HRK1_Atcv | *Acanthocystis turfacea* Chlorella virus Br0604L | SEQ ID NO: 52 |
| M1I273_Atcv | *Acanthocystis turfacea* Chlorella virus NE-JV-2 | SEQ ID NO: 53 |
| M1I600_Atcv | *Acanthocystis turfacea* Chlorella virus TN603.4.2 | SEQ ID NO: 54 |
| M1H4A4_Atcv | *Acanthocystis turfacea* Chlorella virus GM0701.1 | SEQ ID NO: 55 |
| F5B464_Sphage | *Synechococcus* phage S-CRM01 | SEQ ID NO: 56 |
| A0A0F9M1S3 | marine sediment metagenome - uncharacterized protein | SEQ ID NO: 57 |

TABLE 19

NAD dependent ligases

| Name | Origin | SEQ ID |
|---|---|---|
| MtNAD | *Mycobacterium tuberculosis* (strain ATCC 25618/H37RV) | SEQ ID NO: 58 |
| EfNAD | *Enterococcus faecalis* (strain ATCC 700802/V583) | SEQ ID NO: 59 |
| HiNAD | *Haemophilus influenzae* (strain ATCC 51907/DSM 11121/KW20/Rd) | SEQ ID NO: 60 |
| SaNAD | *Staphylococcus aureus* | SEQ ID NO: 61 |
| SpNAD | *Streptococcus pneumoniae* (strain P1031) | SEQ ID NO: 62 |

CBD-Ligase fusions were bound to PERLOZA® beads as described in 1.4 with the following modifications. CBD-ligase fusion proteins were grown from a single colony of BL21 (DE3) cells (NEB) and grown in a 50 mL expression culture. The cells were harvested by centrifugation, resuspended in 5-10 mL Tris-HCl (50 mM, pH 7.5) and lysed by sonication. The lysate was cleared by centrifugation and 1 mL of PERLOZA® 100 (PERLOZA®) beads (50% slurry, pre-equilibrated with 50 mM Tris-HCl PH 7.5) was added to the supernatant which was shaken at 20° C. for 1 hour. The PERLOZA® cellulose beads were then collected and washed with 30 ml buffer (50 mM Tris PH 8.0, 200 mM NaCl, 0.1% TWEEN® 20, 10% Glycerol) followed by 10 ml Tris-HCl (50 mM, pH 7.5) and were finally re-suspended in 1 mL Tris-HCl (50 mM, pH 7.5). In order to analyse protein expression, 20 µl of the PERLOZAR bead slurry was mixed with 20 µl of SDS loading buffer and incubated at 95° C. for 5 minutes before being run on a SDS PAGE gradient gel (4-20%) according to a standard protocol.

12.2 2' MOE and Phosphorothioate Modified Oligonucleotide Assembly and Ligation Method Modified oligonucleotide segments with a phosphorothioate backbone, 2' MOE ribose sugar modifications and 5-methylated pyrimidine bases shown in example 10.2 table 17 were used. Each oligonucleotide segment and template was dissolved in nuclease free water as detailed below:

| | |
|---|---|
| Biotinylated template | 1500 ng/µl |
| 5' segment 2' MOE PS | 1008 ng/µl |
| Centre segment PS | 725 ng/µl |
| 3' segment 2' MOE PS | 1112 ng/µl |

ATP Assay mix was prepared as follows:

| | |
|---|---|
| template | 85.6 µl |
| 5' segment 2' MOE PS | 43.5 µl |
| centre segment PS | 46.8 µl |
| 3' segment 2' MOE PS | 40.1 µl |
| DTT 1M | 8 µl |
| MgCL2 1M | 4 µl |
| ATP (50 mM) | 16 µl |
| Tris 0.5M | 80 µl |
| water | 476 µl |

NAD Assay mix was prepared as follows:

| | |
|---|---|
| template | 85.6 µl |
| 5' segment 2' MOE PS | 43.5 µl |
| centre segment PS | 46.8 µl |
| 3' segment 2' MOE PS | 40.1 µl |
| DTT 1M | 8 µl |
| MgCL2 1M | 4 µl |
| NAD (50 mM) | 1.6 µl |
| Tris 0.5M | 80 µl |
| water | 490.4 µl |

Each immobilized protein (40 µl, 50% PERLOZA® bead slurry) was pipetted into a PCR tube. The beads were pelleted by centrifugation and the supernatant was removed by pipetting. Assay mix (40 µl) was added to each reaction (The final reactions contained 20 µM of each segment and template, 50 mM Tris-HCl, 10 mM $MgCl_2$, 1 mM ATP or 100 µM NAD, 10 mM DTT, pH 7.5, and 40 µl of ligase on PERLOZA® beads). A reaction containing no protein served as a negative control. Reactions were incubated for 18 hours at 30° C. and then quenched by heating to 95° C. for 10 minutes. Precipitated proteins were cleared by centrifugation and samples were analysed by HPLC.

12.3 Results and Conclusion

Product, template and segment oligonucleotides were clearly resolved in the control chromatogram and no ligation was observed. HPLC analysis of the ligase reactions showed that all proteins catalyzed the successful ligation of the 5' segment and centre segment to form an intermediate product, but only some ligases catalyzed the ligation of all three segments to yield the full length product as described in table 20. The NAD dependent ligase from *Staphylococcus aureus* (SaNAD, SEQ ID NO:61) yielded the most full length product. Optimisation to improve product yield is possible and within the skilled person's skill set.

TABLE 20

| | SED ID | Conversion (%)* | |
|---|---|---|---|
| Gene name | NO | intermediate | product |
| M1I5D1_Pbcv | 48 | 5.0 | 0.8 |
| M1I998_Pbcv | 49 | 5.1 | 0.0 |
| M1HX09_Pbcv | 50 | 14.4 | 6.6 |
| M1HUL0_Atcv | 51 | 9.5 | 2.0 |
| M1HRK1_Atcv | 52 | 2.8 | 9.4 |
| M1I273_Atcv | 53 | 12.0 | 6.4 |
| M1I600_Atcv | 54 | 8.8 | 5.1 |
| M1H4A4_Atcv | 55 | 2.1 | 0.0 |
| F5B464_Sphage | 56 | 2.1 | 0.0 |
| A0A0F9M1S3_ms_metagenome | 57 | 1.4 | 0.0 |
| MtNAD | 58 | 7.1 | 0.0 |
| EfNAD | 59 | 19.1 | 0.0 |
| HiNAD | 60 | 0.3 | 0.0 |
| SaNAD | 61 | 10.5 | 11.8 |
| SpNAD | 62 | 19.0 | 0.0 |

*Conversion was calculated from the HPLC peak area relative to the template which is not consumed in the reaction and serves as an internal standard. Conversion = product area/(template + product area)*100

Example 13: Semi-Continuous Ligation Reaction 13.1 Materials

A mutant *Staphylococcus aureus* ligase (NAD-14) fused at the N-terminal to a CBD was produced using standard cloning, expression and extraction methods. CBD-NAD-14 mutant ligase was then bound to PERLOZA® beads: 50 ml of protein lysate was added to 7.5 ml PERLOZAR beads, incubated at room temperature for 1 hour and then the beads were collected in a glass column (BioRad Econo-Column 10 cm length, 2.5 cm diameter #7372512). The beads were washed with 200 ml Buffer Y (50 mM Tris8, 500 mM NaCl, 0.1% TWEEN® 20, 10% Glycerol), then with 200 ml Buffer Z (50 mM Tris8, 200 mM NaCl, 0.1% TWEEN® 20, 10% Glycerol) and 200 ml PBS. The estimated concentration of mutant NAD-14 ligase on the beads was 69 µM of ligase per ml of beads.

The following template DNA oligonucleotide and segment oligonucleotides (Table 21) were synthesized by standard solid phase methods.

TABLE 21

| Segment | Sequence | MW | % HPLC purity |
|---|---|---|---|
| Template 3 | 5' TTTGGTGCGAAGCAGACTGAGGC-3' (SEQ ID NO: 30) | | |
| centre segment | 5'-(p)dTdCdTdGdCdT-3' | 1865.4 | 97.5 |
| MOE 3'-segment | 5'-(p)dTdCmGmCmAmCmC-3' | 2546.7 | 98.0 |

TABLE 21-continued

| Segment | Sequence | MW | % HPLC purity |
|---|---|---|---|
| MOE 5'-segment | 5'-mGmCmCmUmCdAdG-3' | 2492.7 | 98.3 |

Figure 11:
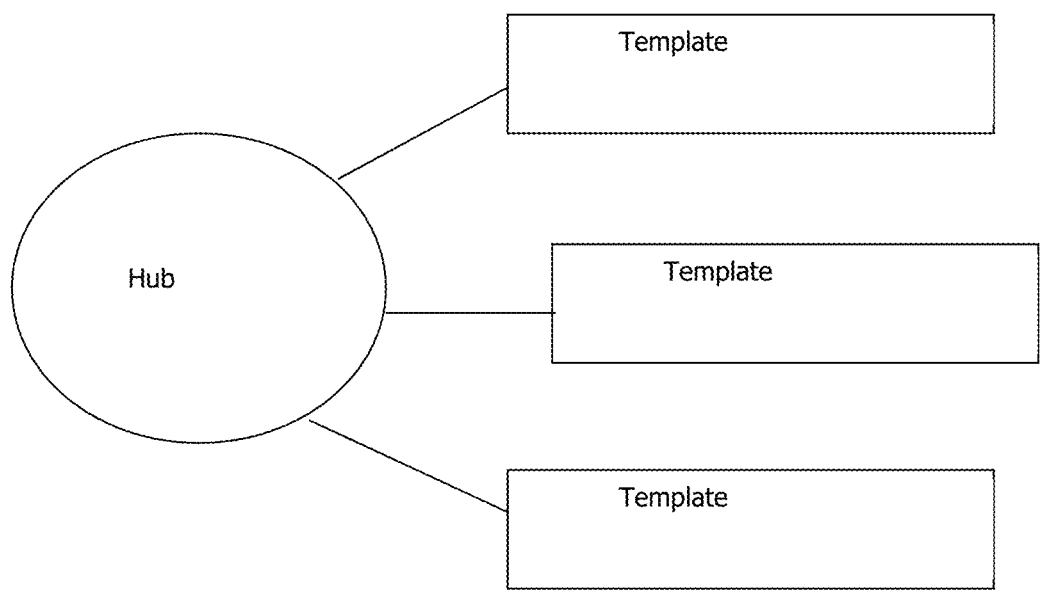
FIG. 11 Schematic of the "tri-template hub" used in Example 13, comprising a support material referred to as the "hub" and three template sequences.

(p) = phosphate, mX = MOE bases, dX = DNA bases
all 5-methyl pyrimidines
all linkages are phosphodiester linkages A "tri-template hub" (approximately 24 kDa) comprising a support material referred to as the "hub" and three template sequences was produced (FIG. 11). Each copy of the template was covalently attached, at its own individual attachment point, to the "hub". The "tri-template hub" molecule is a higher molecular weight than the target (product) oligonucleotide (100% complementary to the template sequence), thereby allowing it to be retained when the impurities and products are separated from the reaction mixture. It should be noted that in this particular case the template sequence was SEQ ID NO:30 and three copies were attached to the hub. In the following example, a tri-template hub is also produced, but with a different template sequence. Accordingly, as the template sequence varies between examples, so too does the tri-template hub.

The following reaction mix (total volume 5 ml) was prepared:

| 250 µl | 1M KH$_2$PO$_4$, pH 7.5 | (50 mM final) |
|---|---|---|
| 108 µl | 0.07011M centre segment | (1.5 mM final) |
| 137 µl | 0.05481M 3'-segment | (1.5 mM final) |
| 168 µl | 0.04461M 5'-segment | (1.5 mM final) |
| 750 µl | 0.00387M Hub (Template) | (0.55 mM final) |
| 350 µl | 50 mM NAD$^+$ | (3.5 mM final) |
| 1000 µl | 50 mM MgCl$_2$ | (10 mM final) |
| 2237 µl | Nuclease free H$_2$O | |

13.2 Methods

Figure 12:
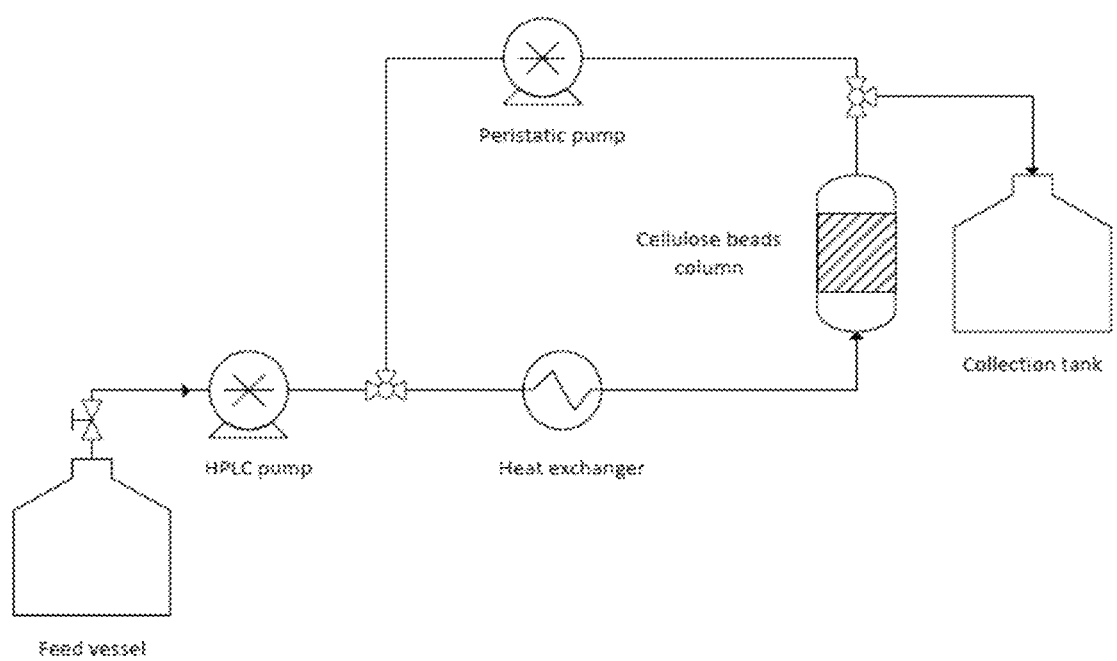
FIG. 12 Schematic of the semi-continuous ligation rig used in Example 13.

A semi-continuous system was set up as shown in FIG. 12.

4 ml of PERLOZA® beads and immobilised mutant NAD-14 ligase were packed into a Pharmacia XK16 column (B). A water bath and peristaltic pump (C) was used to keep the temperature of the column, using the column water compartment, at 30° C. The beads were equilibrated by running 120 ml (30× column volume) of buffer containing 50 mM KH$_2$PO$_4$ at pH7.5 for 120 minutes at 1 ml/min. An AKTA explorer pump A1 (A) was used to create the flow through the Pharmacia XK16 column.

Following column equilibration, the 5 ml reaction mix (mixed well by vortexing) was loaded onto the column, collected in the reservoir tube (D) and recirculated through the column using the AKTA explorer A1 pump. The reaction mix was recirculated through the system at a flow rate of 1 ml/min in continuous circulation mode for 16 hours. Samples were collected after 30 minutes, 60 minutes, 90 minutes, 4 hours, 5 hours, 6 hours, 7 hours, 14 hours and 16 hours for HPLC analysis.

13.3 Results and Conclusions

TABLE 22

| Sample | 5'-segment (%) | Centre segment (%) | 3'-segment (%) | 5' + centre intermediate (%) | Product (%) |
|---|---|---|---|---|---|
| 30 min | 7.80 | 11.00 | 24.00 | 39.40 | 4.40 |
| 60 min | 3.30 | 4.50 | 18.80 | 41.50 | 18.90 |

TABLE 22-continued

| Sample | 5'-segment (%) | Centre segment (%) | 3'-segment (%) | 5' + centre intermediate (%) | Product (%) |
|---|---|---|---|---|---|
| 90 min | 2.10 | 2.80 | 15.10 | 33.80 | 34.40 |
| 4 hr | 1.80 | 2.40 | 9.60 | 19.20 | 56.80 |
| 5 hr | 1.72 | 2.40 | 8.30 | 15.70 | 61.50 |
| 6 hr | 1.69 | 2.50 | 8.60 | 15.90 | 69.40 |
| 7 hr | 1.70 | 2.40 | 8.30 | 14.80 | 70.90 |
| 14 hr | 2.00 | 2.70 | 1.60 | 5.40 | 88.10 |
| 16 hr | 0.80 | 1.90 | 1.70 | 3.30 | 89.50 |

The percentage of each segment, intermediate and product is expressed as fractional peak area relative to the tri-template hub peak area.

In conclusion, the semi-continuous flow reaction worked and after 16 hours the reaction was almost complete.

Example 14: Separating Oligonucleotides of Different Sizes by Filtration: A) Separation of a 20-Mer Oligonucleotide (SEQ ID NO:1) and a Hub Comprising Three Non-Complementary 20-Mer Oligonucleotides (SEQ ID NO:30); (b) Separation of a 20-Mer Oligonucleotide (SEQ ID NO:1) from Segment 6-Mer and 8-Mer Oligonucleotides (See Table 1) and a Hub Comprising Three Complementary 20-Mer Oligonucleotides (SEQ ID NO:2)

14.1 Materials

All oligonucleotides used were synthesized by standard solid phase methods.

A tri-template hub, as described in 13.1 (FIG. 11), was used.

A variety of filters of varying molecular weight cut-offs and from different manufacturers were used as shown in Tables 23 and 24.

14.2 Methods 14.2.1 Dead-End Filtration Set-Up and Protocol for Screening of Polymeric Membranes: (Protocol 1)

Figure 13:
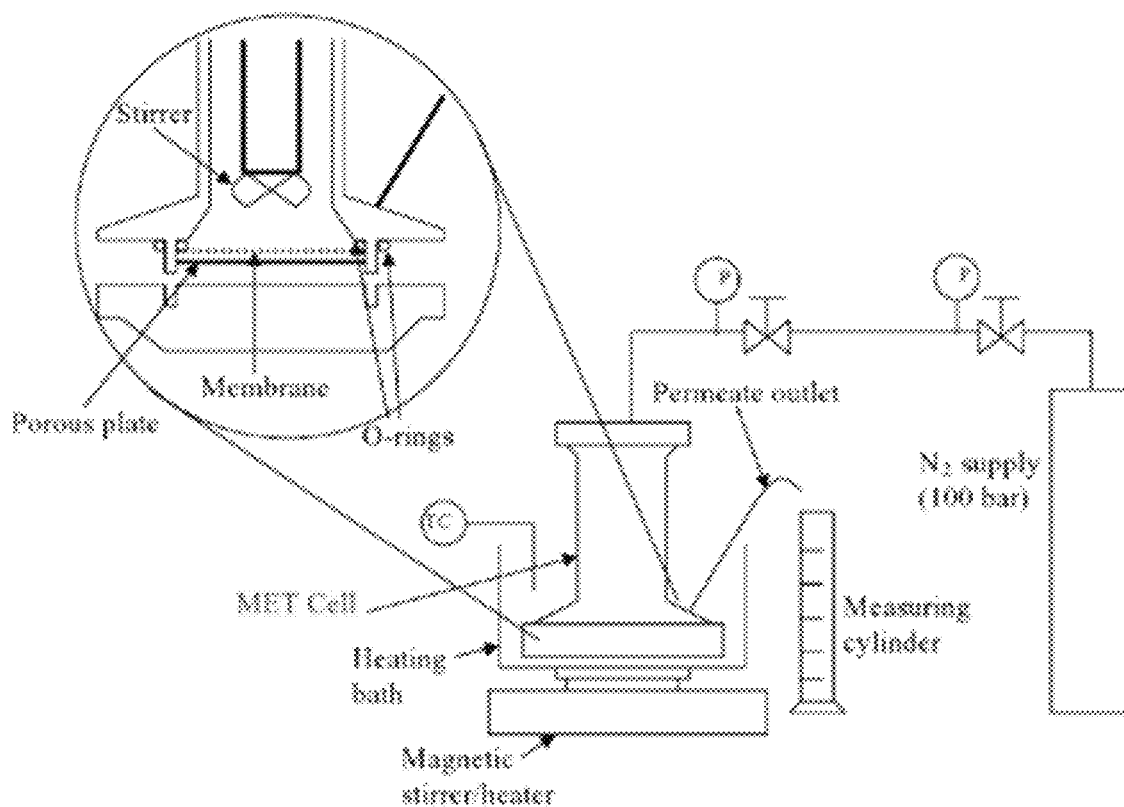
FIG. 13 Schematic of the dead-end filtration rig used in Example 14.

A dead-end filtration rig was set-up as shown in FIG. 13 comprising a MET dead-end filtration cell placed in a water bath sitting on a magnetic stirrer and hotplate. Pressure inside the cell was provided from a flow of nitrogen.

The coupon of membrane (14 cm$^2$) to be tested was first cut to the appropriate size and placed in the cell. The membrane was first conditioned with HPLC grade water (200 ml) and then with PBS buffer (200 ml). The cell was then depressurised, the remaining PBS solution was removed and replaced by a solution containing oligonucleotides (40 ml of oligonucleotides in PBS at a 1 g/L concentration). The cell was placed on a hot stirrer plate and the solution was heated to the desired temperature while being stirred using magnetic agitation. Pressure was applied to the cell (aiming for approximately 3.0 bar; the actual pressure was recorded in each case). Stirring of the solution was either stopped or continued and permeate solution was collected (approximately 20 ml) and analysed by HPLC. Flux was recorded. The system was then depressurised to allow sampling and analysis by HPLC of the retentate solution. More PBS buffer (20 ml) was then added to the filtration cell and the previous procedure was repeated 3 times. The membrane was finally washed with PBS buffer.

All samples were analysed by HPLC without any dilution.

14.2.2 Cross-Flow Filtration Set-Up and Protocol for Screening of Polymeric Membranes: (Protocol 2)

Figure 14:
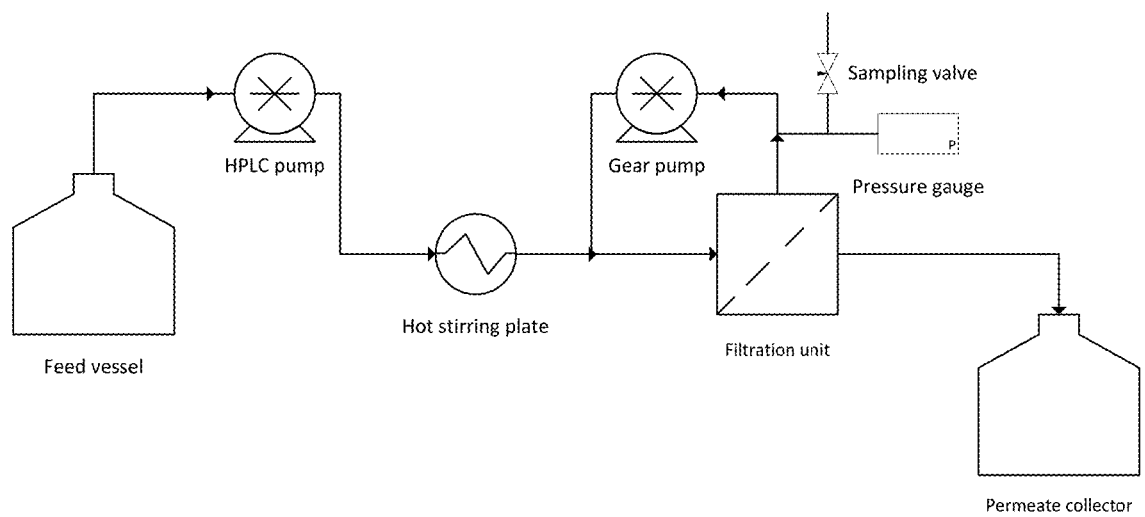
FIG. 14 Schematic of the cross-flow filtration rig used in Example 14.

A cross-flow filtration rig was set-up as shown in FIG. 14. The feed vessel (1) consisting of a conical flask contained the oligonucleotide solution to be purified. The solution was pumped to a cross-flow filtration cell (4) using an HPLC pump (2) while temperature within the cell was maintained using a hot plate (3). The solution within the cell was recirculated using a gear pump (6). A pressure gauge (5) enabled the pressure to be read during the experiment. Samples of the retentate solution were taken from the sampling valve (7) while the permeate solution was sampled from the permeate collection vessel (8).

The coupon of membrane to be tested was first cut to the appropriate size and placed in the cell. The system was washed with a PBS solution (100 ml). Temperature of the solution was adjusted to the desired set point. A solution containing oligonucleotide products in PBS (7.5 ml at 1 g/L) was fed into the system. PBS solution was then pumped into the system using the HPLC pump at a flow rate matching the flow rate of the permeate solution (typically 3 ml/min). Pressure was recorded using the pressure gauge. The retentate solution was sampled for HPLC analysis every 5 diafiltration volumes. The permeate solution was sampled for HPLC analysis every diafiltration volume. The experiment was stopped after 20 diafiltration volumes.

In the case of the experiment using the Synder membrane having a 5 kDa molecular weight cut off (lot number 120915R2) and SEQ ID NO:46 and SEQ ID NO:30 the above methodology was modified as follows. The coupon of membrane to be tested was first cut to the appropriate size and placed in the cell. The system was washed with a Potassium phosphate solution (100 ml, 50 mM, pH 7.5). Temperature of the solution was adjusted to the desired set point. A solution containing oligonucleotide products in potassium phosphate (approximately 1 g/L) was added to ethylenediaminetetraacetic acid (EDTA) (230 µL of a 500 mM solution). The solution was then fed into the system. Potassium phosphate buffer was then pumped into the system using the HPLC pump at a flow rate matching the flow rate of the permeate solution (typically 4 ml/min). Pressure was recorded using the pressure gauge. The retentate solution was sampled for HPLC analysis every 5 diafiltration volumes. The permeate solution was sampled for HPLC analysis every diafiltration volume. The experiment was stopped after 15 diafiltration volumes 14.3 Results

TABLE 23 results for the dead-end filtration experiments following protocol 1 (14.2.1)

| Stirring (Yes or No) | Membrane | MWCO (kDa) | Lot number | SEQ ID NO | Temp. (° C.) | Rejection (%) Product | Tri-template hub |
|---|---|---|---|---|---|---|---|
| Yes | NADIR | 10 | 226162 | 1 and 30 | 60 | 38 | 96 |
| Yes | NADIR | 10 | 226162 | 1 and 2 | 60 | 90 | 98 |
|  |  |  |  |  | 80 | 40 | 43 |
| Yes | NADIR | 10 | 226162 | 1 and 2 | 60 | 83 | 92 |
|  |  |  |  |  | 65 | 77 | 84 |
|  |  |  |  |  | 70 | 38 | 41 |
|  |  |  |  |  | 75 | 12 | 20 |
| Yes | NADIR | 5 | 226825 | 1 and 2 | 60 | 97 | 95 |
|  |  |  |  |  | 65 | 99 | 93 |
|  |  |  |  |  | 70 | 97 | 92 |
|  |  |  |  |  | 75 | 90 | 95 |
| No | NADIR | 5 | 226825 | 1 and 2 | 75 | 66 | 96 |
| No | NADIR | 10 | 226162 | 1 and 2 | 75 | 80 | 80 |
| No | Snyder | 5 | 120915R2 | 1 and 2 | 75 | 97 | 98 |
| No | Osmonics | 5 | 622806PT | 1 and 2 | 75 | 99 | 98 |
| No | Osmonics | 10 | 622806PW | 1 and 2 | 75 | 86 | 95 |

MWCO = molecular weight cut-off

Figure 15A:
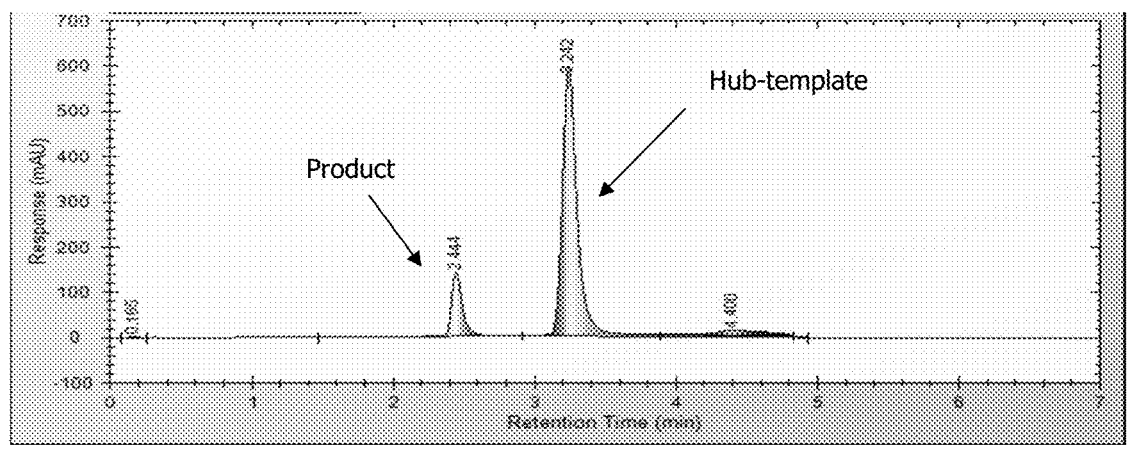
FIG. 15A and FIG. 15B Chromatograms showing the results from the dead end filtration experiments using the 10 kDa MWCO NADIR® membrane at 60° C. in Example 14.
Figure 15B:
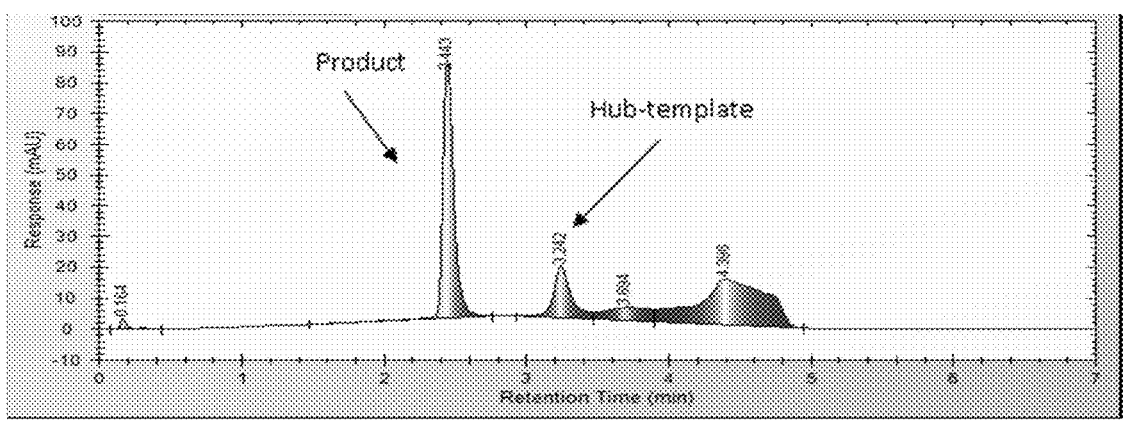

In the experiment using the 10 kDa MWCO NADIR® membrane at 60° C., clear separation between the product sequence (SEQ ID NO:1) and the non-complementary tri-template hub (comprising SEQ ID NO:30) was demonstrated. FIG. 15A shows a chromatogram of the retentate solution, which remained in the filtration cell and contained mainly tri-template hub, after two diafiltration volumes; and FIG. 15B a chromatogram of the permeate, solution enriched in the product, after two diafiltration volumes.

TABLE 24 results for the cross-flow filtration experiments (following protocol 2) (14.2.2)

| Membrane | MWCO (kDa) | Lot number | SEQ ID NO | Temp. (° C.) | Pressure | Diafiltration volume | Rejection (%) Segment 1 | Segment 2 | Segment 3 | Product | Tri-template hub |
|---|---|---|---|---|---|---|---|---|---|---|---|
| Osmonics | 10 | 622806PW | 1 and 2 | 75 | 3.1 | 0 | N/A | N/A | N/A | 100 | 88 |
| | | | | | | 5 | N/A | N/A | N/A | 64 | 88 |
| | | | | | | 10 | N/A | N/A | N/A | 40 | 82 |
| | | | | | | 15 | N/A | N/A | N/A | 12 | 74 |
| Synder | 5 | 120915R2 | 1 and 2 | 75 | 3.1 | 0 | N/A | N/A | N/A | 100 | 100 |
| | | | | 82 | | 5 | N/A | N/A | N/A | 88 | 100 |
| | | | | 75 | | 10 | N/A | N/A | N/A | 98 | 100 |
| | | | | 75 | | 15 | N/A | N/A | N/A | 98 | 100 |
| | | | | 75 | | 20 | N/A | N/A | N/A | 96 | 100 |
| Synder | 5 | 120915R2 | 1 and 2 | 85 | 3.1 | 0 | N/A | N/A | N/A | 99 | 99 |
| | | | | | | 5 | N/A | N/A | N/A | 63 | 99 |
| | | | | | | 10 | N/A | N/A | N/A | 79 | 99 |
| | | | | | | 15 | N/A | N/A | N/A | 100 | 98 |
| | | | | | | 20 | N/A | N/A | N/A | 100 | 99 |
| Synder | 5 | 120915R2 | 1 and 2 + segments from table 1 | 50 | 3.0 | 0 | 100 | 100 | 100 | 100 | 100 |
| | | | | | | 5 | 39 | 39 | 40 | 100 | 100 |
| | | | | | | 10 | 82 | 86 | 86 | 100 | 100 |
| | | | | | | 15 | 77 | 81 | 79 | 100 | 100 |
| | | | | | | 20 | * | * | * | 100 | 100 |
| Synder | 5 | 120915R2 | 1 and 2 | 80 | 3.1 | 0 | N/A | N/A | N/A | 96 | 100 |
| | | | | | | 5 | N/A | N/A | N/A | 22 | 96 |
| | | | | | | 10 | N/A | N/A | N/A | 10 | 100 |
| | | | | | | 20 | N/A | N/A | N/A | 38 | 100 |
| Synder | 5 | 120915R2 | 46 and 30 | 80 | 3.4 | 0 | N/A | N/A | N/A | 98 | 100 |
| | | | | | | 5 | N/A | N/A | N/A | 83 | 100 |
| | | | | | | 10 | N/A | N/A | N/A | 68 | 100 |
| | | | | | | 15 | N/A | N/A | N/A | 72 | 100 |

Figure 16A:
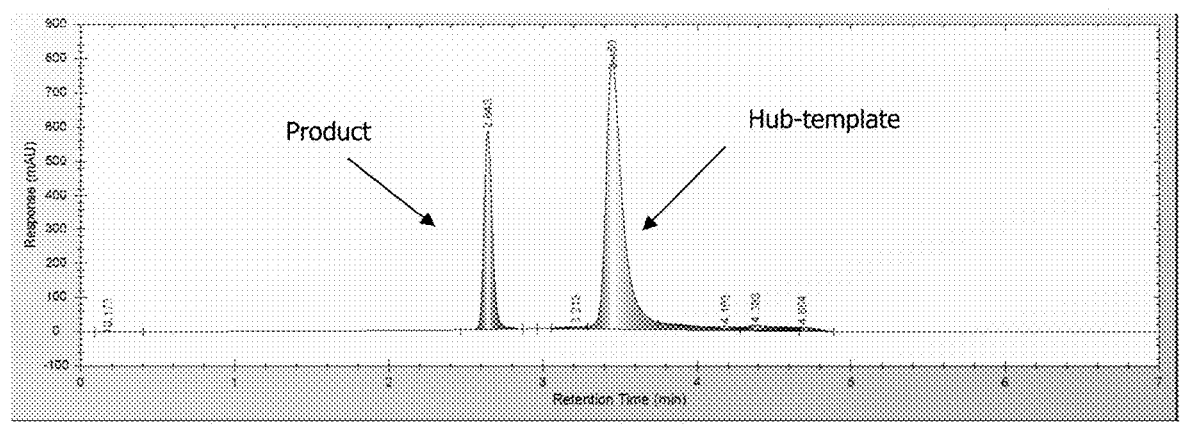
FIG. 16A and FIG. 16B Chromatograms showing the results from the cross-flow filtration experiments using the 5 kDa MWCO Synder membrane at 50° C. and 3.0 bar pressure, in Example 14.
Figure 16B:
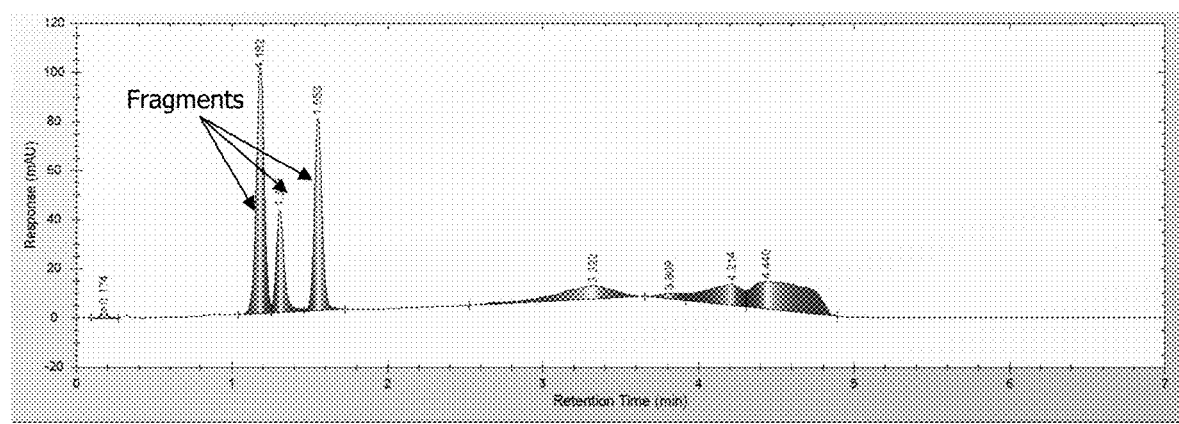

MWCO = molecular weight cut-off
* concentration of solutes too low preventing meaningful analysis In the experiment using the 5 kDa MWCO Synder membrane at 50° C. and 3.0 bar pressure, clear separation between the segment sequences (see table 1) and the complementary tri-template hub (comprising SEQ ID NO:2) and product (SEQ ID NO:1) was demonstrated. FIG. 16A shows a chromatogram of the retentate solution, which contained mainly tri-template hub and product, after 20 diafiltration volumes; and FIG. 16B a chromatogram of the permeate, which contained mainly segment oligonucleotides, after 20 diafiltration volumes.

Figure 17A:
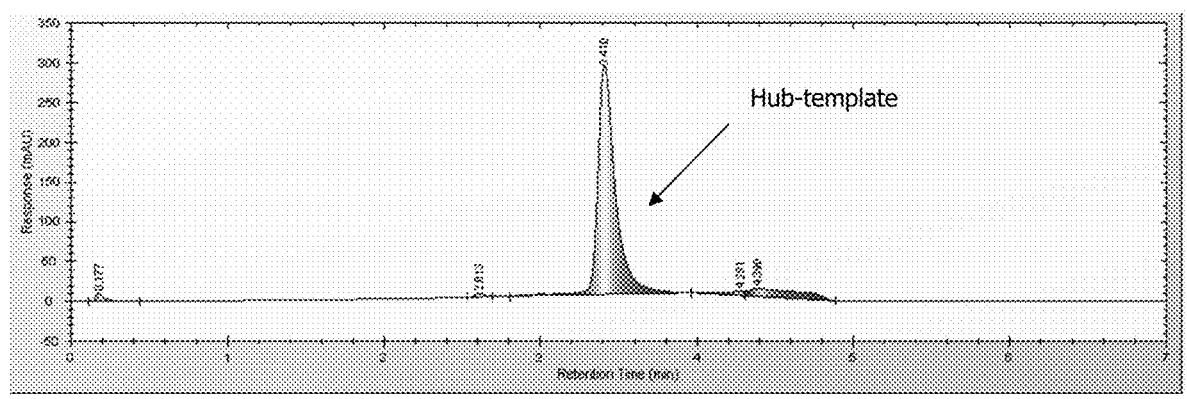
FIG. 17A and FIG. 17B Chromatograms showing the results from the cross-flow filtration experiments using the 5 kDaMWCO Synder membrane at 80° C. and 3.1 bar pressure, in Example 14.
Figure 17B:
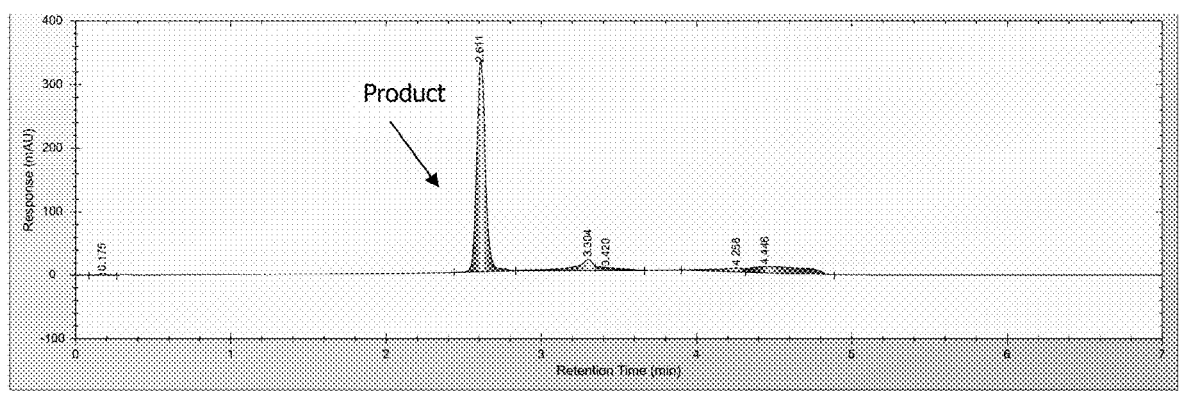

In the experiment using the 5 kDa MWCO Synder membrane at 80° C. and 3.1 bar pressure, clear separation between the complementary tri-template hub (comprising SEQ ID NO: 2) and product (SEQ ID NO:1) was demonstrated. FIG. 17A shows a chromatogram of the retentate solution, which contained tri-template hub only, after 20 diafiltration volumes; and FIG. 17B a chromatogram of the permeate solution, which contained the product only, after 2 diafiltration volumes.

14.4 Conclusions

Oligonucleotides of different lengths and molecular weights can be separated using filtration. As shown above, the type of membrane and the conditions, such as temperature, affect the level of separation. For a given set of oligonucleotides of different lengths/molecular weights, suitable membranes and conditions can be selected to allow the required separation. For example, we have demonstrated that segment oligonucleotides (shortmers of 6 and 8 nucleotides in length), as outlined in table 1, can be separated from the product oligonucleotide (20-mer oligonucleotide having SEQ ID NO:1) and tri-template hub (comprising 3×20-mer of SEQ ID NO:2 attached to a solid support), and the product oligonucleotide and tri-template hub can, in turn, be separated from each other.

Overall Conclusions

We have shown that it is possible to synthesize oligonucleotides, including oligonucleotides with a range of therapeutically relevant chemical modifications, in solution by assembling short oligonucleotide segments on a complementary template, ligating the segments together and separating the product oligonucleotide from both impurities and its complementary template in an efficient process that is scaleable and suitable for large scale therapeutic oligonucleotide manufacture.

By synthesizing oligonucleotides in solution we have avoided the scale up constraints imposed by solid phase methods. In using the inherent properties of DNA to recognise complementary sequences specifically and bind complementary sequences with an affinity that reflects both the fidelity of the complementary sequence and the length of the complementary sequence we have been able to produce oligonucleotides of high purity without the need for chromatography. This both improves the efficiency of the production process and the scaleability of the process. By recovering the template in an unchanged state during the separation process we are able to reuse the template for further rounds of synthesis and so have avoided the economic consequences of having to make one equivalent of template for every equivalent of product oligonucleotide formed.

Finally, although wild type ligases are known to ligate normal DNA effectively, we have shown that modifications to DNA result in decreased ligation efficiency and multiple modifications to the DNA are additive in their effect on decreasing the efficiency of ligation which can, in some cases render the DNA ligase completely ineffective. We have shown that by appropriate mutation and evolution of DNA ligases, ligation efficiency can be restored and appropriately modified DNA ligases are effective catalysts for synthesizing oligonucleotides which contain multiple modifications.

| SEQUENCE LISTING | |
|---|---|
| SEQ ID NO | Sequence Identifier |
| 1 | Example 1 desired product oligonucleotide sequence ("target") |
| 2 | Example 1-4,6, 10 and 11 template oligonucleotide sequence |
| 3 | Wild type T4 DNA ligase protein sequence |
| 4 | Wild type T4 DNA ligase protein sequence (when fused to CBD) |
| 5 | Example 2 target sequence |
| 6 | Wild-type Enterobacteria phage CC31 DNA ligase protein sequence |
| 7 | Wild-type Enterobacteria phage CC31 DNA ligase protein sequence (when fused to CBD) |
| 8 | Wild-type Shigella phage Shf125875 DNA ligase protein sequence |
| 9 | Wild-type Shigella phage Shf125875 DNA ligase protein sequence (when fused to CBD) |
| 10 | Mutant ligase (T4 backbone) protein sequence |
| 11 | Mutant ligase (T4 backbone) protein sequence |
| 12 | Mutant ligase (T4 backbone) protein sequence |
| 13 | Mutant ligase (T4 backbone) protein sequence |
| 14 | Mutant ligase (T4 backbone) protein sequence |
| 15 | Mutant ligase (T4 backbone) protein sequence |
| 16 | Mutant ligase (T4 backbone) protein sequence |
| 17 | Mutant ligase (T4 backbone) protein sequence |
| 18 | Mutant ligase (T4 backbone) protein sequence |
| 19 | Mutant ligase (T4 backbone) protein sequence |
| 20 | Mutant ligase (T4 backbone) protein sequence |
| 21 | Mutant ligase (T4 backbone) protein sequence |
| 22 | Mutant ligase (T4 backbone) protein sequence |
| 23 | Mutant ligase (Enterobacteria phage CC31 backbone-clone A4) protein sequence |
| 24 | Mutant ligase (Enterobacteria phage CC31 backbone) protein sequence |
| 25 | Mutant ligase (Enterobacteria phage CC31 backbone) protein sequence |
| 26 | Mutant ligase (Enterobacteria phage CC31 backbone) protein sequence |
| 27 | Mutant ligase (Enterobacteria phage CC31 backbone) protein sequence |
| 28 | Mutant ligase (*Shigella* phage Shf125875 backbone) protein sequence |
| 29 | Wild-type *Chlorella* ligase protein sequence |
| 30 | Example 5, 8 and 9 template oligonucleotide sequence |
| 31 | Example 5 template oligonucleotide sequence |
| 32 | Example 5 template oligonucleotide sequence |
| 33 | Example 5 template oligonucleotide sequence |
| 34 | Example 5 template oligonucleotide sequence |

-continued

| | SEQUENCE LISTING |
|---|---|
| 35 | Example 5 template oligonucleotide sequence |
| 36 | Example 5 template oligonucleotide sequence |
| 37 | Example 5 template oligonucleotide sequence |
| 38 | Example 5 template oligonucleotide sequence |
| 39 | Example 5 template oligonucleotide sequence |
| 40 | Example 5 template oligonucleotide sequence |
| 41 | Example 5 template oligonucleotide sequence |
| 42 | Example 5 template oligonucleotide sequence |
| 43 | Example 5 template oligonucleotide sequence |
| 44 | Example 5 template oligonucleotide sequence |
| 45 | Example 5 template oligonucleotide sequence |
| 46 | Example 14 "20 mer" oligonucleotide sequence |
| 47 | Example 7 template oligonucleotide sequence |
| 48 | *Paramecium bursaria Chlorella* virus NE-JV-4 ligase |
| 49 | *Paramecium bursaria Chlorella* virus NYs1 ligase |
| 50 | *Paramecium bursaria Chlorella* virus NE-JV-1 ligase |
| 51 | *Acanthocystis turfacea Chlorella* virus Canal-1 ligase |
| 52 | *Acanthocystis turfacea Chlorella* virus Br0604L ligase |
| 53 | *Acanthocystis turfacea Chlorella* virus NE-JV-2 ligase |
| 54 | *Acanthocystis turfacea Chlorella* virus TN603.4.2 ligase |
| 55 | *Acanthocystis turfacea Chlorella* virus GM0701.1 ligase |
| 56 | *Synechococcus* phage S-CRM01 ligase |
| 57 | marine sediment metagenome ligase |
| 58 | *Mycobacterium tuberculosis* (strain ATCC 25618/H37Rv) ligase |
| 59 | *Enterococcus faecalis* (strain ATCC 700802N583) ligase |
| 60 | *Haemophilus* influenzae (strain ATCC 51907/DSM 11121/ KW20/Rd) ligase |
| 61 | *Staphylococcus aureus* ligase |
| 62 | *Streptococcus pneumoniae* (strain P1031) ligase |

SEQ ID NO: 1
GGCCAAACCTCGGCTTACCT

SEQ ID NO: 2
TTTAGGTAAGCCGAGGTTTGGCC

SEQ ID NO: 3
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVIDVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 4
GSILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN

SEQUENCE LISTING

GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVIDVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 5
CCC AAC ACC UCG GCU UAC Cu

SEQ ID NO: 6
MILDIINEIASIGSTKEKEAIIRRHKDNELLKRVFRMTYDGKLQYYIKKWDTRPKGDIHLTLEDMLY
LLEEKLAKRVVTGNAAKEKLEIALSQTSDADAEVVKKVLLRDLRCGASRSIANKVWKNLIPEQPQ
MLASSYDEKGIEKNIKFPAFAQLKADGARAFAEVRGDELDDVKILSRAGNEYLGLDLLKQQLIEM
TKEARERHPGGVMIDGELVYHASTLPAGPLDDIFGDLPELSKAKEFKEESRTMSNGLANKSLK
GTISAKEAAGMKFQVWDYVPLDVVYSEGKQSGFAYDVRFRALELMVQGYSQMILIENHIVHNL
DEAKVIYRKYVDEGLEGIILKNIGAFWENTRSKNLYKFKEVITIDLRIVDIYEHSKQPGKAGGFYLE
SECGLIKVKAGSGLKDKPGKDAHELDRTRIWENKNDYIGGVLESECNGWLAAEGRTDYVKLFL
PIAIKMRRDKDVANTFADIWGDFHEVTGL

SEQ ID NO: 7
GSILDIINEIASIGSTKEKEAIIRRHKDNELLKRVFRMTYDGKLQYYIKKWDTRPKGDIHLTLEDML
YLLEEKLAKRVVTGNAAKEKLEIALSQTSDADAEVVKKVLLRDLRCGASRSIANKVWKNLIPEQP
QMLASSYDEKGIEKNIKFPAFAQLKADGARAFAEVRGDELDDVKILSRAGNEYLGLDLLKQQLIE
MTKEARERHPGGVMIDGELVYHASTLPAGPLDDIFGDLPELSKAKEFKEESRTMSNGLANKSL
KGTISAKEAAGMKFQVWDYVPLDVVYSEGKQSGFAYDVRFRALELMVQGYSQMILIENHIVHN
LDEAKVIYRKYVDEGLEGIILKNIGAFWENTRSKNLYKFKEVITIDLRIVDIYEHSKQPGKAGGFYL
ESECGLIKVKAGSGLKDKPGKDAHELDRTRIWENKNDYIGGVLESECNGWLAAEGRTDYVKLF
LPIAIKMRRDKDVANTFADIWGDFHEVTGL

SEQ ID NO: 8
MILDILNQIAAIGSTKTKQEILKKNKDNKLLERVYRLTYARGIQYYIKKWPGPGERSQAYGLLELD
DMLDFIEFTLATRKLTGNAAIKELMGYIADGKPDDVEVLRRVMMRDLEVGASVSIANKVWPGLI
QLQPQMLASAYDEKLITKNIKWPAFAQLKADGARCFAEVRDDGVQFFSRAGNEYHGLTLLADE
LMEMTKEARERHPNGVLIDGELVYHSFDIKKAVSSGNDLSFLFGDNEESEEVQVADRSTSNGL
ANKSLQGTISPKEAEGMVLQAWDYVPLDEVYSDGKIKGQKYDVRFAALENMAEGFKRIEPIEN
QLVHNLDEAKVVYKKYVDQGLEGIILKNRDSYWENKRSKNLIKFKEVIDIALEVVGYYEHSKDPN
KLGGVELVSRCRRITTDCGSGFKDTTHKTVDGVKVLIPLDERHDLDRERLMAEAREGKLIGRIA
DCECNGWVHSKGREGTVGIFLPIIKGFRFDKTEADSFEDVFGPWSQTGL

SEQ ID NO: 9
GSILDILNQIAAIGSTKTKQEILKKNKDNKLLERVYRLTYARGIQYYIKKWPGPGERSQAYGLLEL
DDMLDFIEFTLATRKLTGNAAIKELMGYIADGKPDDVEVLRRVMMRDLEVGASVSIANKVWPGL
IQLQPQMLASAYDEKLITKNIKWPAFAQLKADGARCFAEVRDDGVQFFSRAGNEYHGLTLLADE
LMEMTKEARERHPNGVLIDGELVYHSFDIKKAVSSGNDLSFLFGDNEESEEVQVADRSTSNGL
ANKSLQGTISPKEAEGMVLQAWDYVPLDEVYSDGKIKGQKYDVRFAALENMAEGFKRIEPIEN
QLVHNLDEAKVVYKKYVDQGLEGIILKNRDSYWENKRSKNLIKFKEVIDIALEVVGYYEHSKDPN
KLGGVELVSRCRRITTDCGSGFKDTTHKTVDGVKVLIPLDERHDLDRERLMAEAREGKLIGRIA
DCECNGWVHSKGREGTVGIFLPIIKGFRFDKTEADSFEDVFGPWSQTGL

SEQ ID NO: 10
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKRVIDVDLKIVGIYPHRKDPTKA
GGFILESECGKIKVNAGSGLKDKAGVKSHELDRTRIMENQNYYIGKILECECNGWLKSDGRTDY
VKLFLPIAIRLREDKTKANTFEDVFGDFHEVTGL

SEQ ID NO: 11
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKGVIDVDLKIVGIYPHRKDPTKA
GGFILESECGKIKVNAGSGLKDKAGVKSHELDRTRIMENQNYYIGKILECECNGWLKSDGRTDY
VKLFLPIAIRLREDKTKANTFEDVFGDFHEVTGL

SEQ ID NO: 12
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKKVIDVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQUENCE LISTING

```
SEQ ID NO: 13
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVILVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 14
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVIKVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 15
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVIQVDLKIVGIYPHRKDPTKA
GGFILESECGKIKVNAGSGLKDKAGVKSHELDRTRIMENQNYYIGKILECECNGWLKSDGRTDY
VKLFLPIAIRLREDKTKANTFEDVFGDFHEVTGL

SEQ ID NO: 16
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVIVVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 17
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEVIRVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 18
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEAIDVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 19
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKEKIDVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 20
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
```

-continued

SEQUENCE LISTING

VVNNLDEAKVIYKKYIDQGLEGIILKNIDGLWENARSKNLYKFKRVIVVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 21
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKKVIEVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 22
MILKILNEIASIGSTKQKQAILEKNKDNELLKRVYRLTYSRGLQYYIKKWPKPGIATQSFGMLTLT
DMLDFIEFTLATRKLTGNAAIEELTGYITDGKKDDVEVLRRVMMRDLECGASVSIANKVWPGLIP
EQPQMLASSYDEKGINKNIKFPAFAQLKADGARCFAEVRGDELDDVRLLSRAGNEYLGLDLLK
EELIKMTAEARQIHPEGVLIDGELVYHEQVKKEPEGLDFLFDAYPENSKAKEFAEVAESRTASN
GIANKSLKGTISEKEAQCMKFQVWDYVPLVEIYSLPAFRLKYDVRFSKLEQMTSGYDKVILIENQ
VVNNLDEAKVIYKKYIDQGLEGIILKNIDGLWENARSKNLYKFKKVIHVDLKIVGIYPHRKDPTKAG
GFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 23
MILDIINEIASIGSTKEKEAIIRRHKDNELLKRVFRMTYDGKLQYYIKKWDTRPKGDIHLTLEDMLY
LLEEKLAKRVVTGNAAKEKLEIALSQTSDADAEVVKKVLLRDLRCGASRSIANKVWKNLIPEQPQ
MLASSYDEKGIEKNIKFPAFAQLKADGARAFAEVRGDELDDVKILSRAGNEYLGLDLLKQQLIEM
TKEARERHPGGVMIDGELVYHASTLPAGPLDDIFGDLPELSKAKEFKEESRTMSNGLANKSLK
GTISAKEAAGMKFQVWDYVPLDVVYSEGKQSGFAYDVRFRALELMVQGYSQMILIENHIVHNL
DEAKVIYRKYVDEGLEGIILKNIGAFWENTRSKNLYKFKRVIVIDLRIVDIYEHSKQPGKAGGFYLE
SECGLIKVKAGSGLKDKPGKDAHELDRTRIWENKNDYIGGVLESECNGWLAAEGRTDYVKLFL
PIAIKMRRDKDVANTFADIWGDFHEVTGL

SEQ ID NO: 24
MILDIINEIASIGSTKEKEAIIRRHKDNELLKRVFRMTYDGKLQYYIKKWDTRPKGDIHLTLEDMLY
LLEEKLAKRVVTGNAAKEKLEIALSQTSDADAEVVKKVLLRDLRCGASRSIANKVWKNLIPEQPQ
MLASSYDEKGIEKNIKFPAFAQLKADGARAFAEVRGDELDDVKILSRAGNEYLGLDLLKQQLIEM
TKEARERHPGGVMIDGELVYHASTLPAGPLDDIFGDLPELSKAKEFKEESRTMSNGLANKSLK
GTISAKEAAGMKFQVWDYVPLDVVYSEGKQSGFAYDVRFRALELMVQGYSQMILIENHIVHNL
DEAKVIYRKYVDEGLEGIILKNIGAFWENTRSKNLYKFKKVIKIDLRIVDIYEHSKQPGKAGGFYLE
SECGLIKVKAGSGLKDKPGKDAHELDRTRIWENKNDYIGGVLESECNGWLAAEGRTDYVKLFL
PIAIKMRRDKDVANTFADIWGDFHEVTGL

SEQ ID NO: 25
MILDIINEIASIGSTKEKEAIIRRHKDNELLKRVFRMTYDGKLQYYIKKWDTRPKGDIHLTLEDMLY
LLEEKLAKRVVTGNAAKEKLEIALSQTSDADAEVVKKVLLRDLRCGASRSIANKVWKNLIPEQPQ
MLASSYDEKGIEKNIKFPAFAQLKADGARAFAEVRGDELDDVKILSRAGNEYLGLDLLKQQLIEM
TKEARERHPGGVMIDGELVYHASTLPAGPLDDIFGDLPELSKAKEFKEESRTMSNGLANKSLK
GTISAKEAAGMKFQVWDYVPLDVVYSEGKQSGFAYDVRFRALELMVQGYSQMILIENHIVHNL
DEAKVIYRKYVDEGLEGIILKNIGAFWENTRSKNLYKFKGVIFIDLRIVDIYEHSKQPGKAGGFYLE
SECGLIKVKAGSGLKDKPGKDAHELDRTRIWENKNDYIGGVLESECNGWLAAEGRTDYVKLFL
PIAIKMRRDKDVANTFADIWGDFHEVTGL

SEQ ID NO: 26
MILDIINEIASIGSTKEKEAIIRRHKDNELLKRVFRMTYDGKLQYYIKKWDTRPKGDIHLTLEDMLY
LLEEKLAKRVVTGNAAKEKLEIALSQTSDADAEVVKKVLLRDLRCGASRSIANKVWKNLIPEQPQ
MLASSYDEKGIEKNIKFPAFAQLKADGARAFAEVRGDELDDVKILSRAGNEYLGLDLLKQQLIEM
TKEARERHPGGVMIDGELVYHASTLPAGPLDDIFGDLPELSKAKEFKEESRTMSNGLANKSLK
GTISAKEAAGMKFQVWDYVPLDVVYSEGKQSGFAYDVRFRALELMVQGYSQMILIENHIVHNL
DEAKVIYRKYVDEGLEGIILKNIGAFWENTRSKNLYKFKGVILIDLRIVDIYEHSKQPGKAGGFYLE
SECGLIKVKAGSGLKDKPGKDAHELDRTRIWENKNDYIGGVLESECNGWLAAEGRTDYVKLFL
PIAIKMRRDKDVANTFADIWGDFHEVTGL

SEQ ID NO: 27
MILDIINEIASIGSTKEKEAIIRRHKDNELLKRVFRMTYDGKLQYYIKKWDTRPKGDIHLTLEDMLY
LLEEKLAKRVVTGNAAKEKLEIALSQTSDADAEVVKKVLLRDLRCGASRSIANKVWKNLIPEQPQ
MLASSYDEKGIEKNIKFPAFAQLKADGARAFAEVRGDELDDVKILSRAGNEYLGLDLLKQQLIEM
TKEARERHPGGVMIDGELVYHASTLPAGPLDDIFGDLPELSKAKEFKEESRTMSNGLANKSLK
GTISAKEAAGMKFQVWDYVPLDVVYSEGKQSGFAYDVRFRALELMVQGYSQMILIENHIVHNL
DEAKVIYRKYVDEGLEGIILKNIGAFWENTRSKNLYKFKRVIFIDLRIVDIYEHSKQPGKAGGFYLE
SECGLIKVKAGSGLKDKPGKDAHELDRTRIWENKNDYIGGVLESECNGWLAAEGRTDYVKLFL
PIAIKMRRDKDVANTFADIWGDFHEVTGL

SEQ ID NO: 28
MILDILNQIAAIGSTKTKQEILKKNKDNKLLERVYRLTYARGIQYYIKKWPGPGERSQAYGLLELD
DMLDFIEFTLATRKLTGNAAIKELMGYIADGKPDDVEVLRRVMMRDLEVGASVSIANKVWPGLI

SEQUENCE LISTING

QLQPQMLASAYDEKLITKNIKWPAFAQLKADGARCFAEVRDDGVQFFSRAGNEYHGLTLLADE
LMEMTKEARERHPNGVLIDGELVYHSFDIKKAVSSGNDLSFLFGDNEESEEVQVADRSTSNGL
ANKSLQGTISPKEAEGMVLQAWDYVPLDEVYSDGKIKGQKYDVRFAALENMAEGFKRIEPIEN
QLVHNLDEAKVVYKKYVDQGLEGIILKNRDSYWENKRSKNLIKFKRVIVIALEWGYYEHSKDPN
KLGGVELVSRCRRITTDCGSGFKDTTHKTVDGVKVLIPLDERHDLDRERLMAEAREGKLIGRIA
DCECNGWVHSKGREGTVGIFLPIIKGFRFDKTEADSFEDVFGPWSQTGL

SEQ ID NO: 29
MAITKPLLAATLENIEDVQFPCLATPKIDGIRSVKQTQMLSRTFKPIRNSVMNRLLTELLPEGSDG
EISIEGATFQDTTSAVMTGHKMYNAKFSYYWFDYVTDDPLKKYIDRVEDMKNYITVHPHILEHA
QVKIIPLIPVEINNITELLQYERDVLSKGFEGVMIRKPDGKYKFGRSTLKEGILLKMQFKDAEATII
SMTALFKNTNTKTKDNFGYSKRSTHKSGKVEEDVMGSIEVDYDGVVFSIGTGFDADQRRDFW
QNKESYIGKMVKFKYFEMGSKDCPRFPVFIGIRHEEDR

SEQ ID NO: 30
TTTGGTGCGAAGCAGACTGAGGC

SEQ ID NO: 31
TTTGGTGCGAAGCAGAGTGAGGC

SEQ ID NO: 32
TTTGGTGCGAAGCAGATTGAGGC

SEQ ID NO: 33
TTTGGTGCGAAGCAGAATGAGGC

SEQ ID NO: 34
TTTGGTGCGAAGCAGTCTGAGGC

SEQ ID NO: 35
TTTGGTGCGAAGCAGTGTGAGGC

SEQ ID NO: 36
TTTGGTGCGAAGCAGTTTGAGGC

SEQ ID NO: 37
TTTGGTGCGAAGCAGTATGAGGC

SEQ ID NO: 38
TTTGGTGCGAAGCAGCCTGAGGC

SEQ ID NO: 39
TTTGGTGCGAAGCAGCGTGAGGC

SEQ ID NO: 40
TTTGGTGCGAAGCAGCTTGAGGC

SEQ ID NO: 41
TTTGGTGCGAAGCAGCATGAGGC

SEQ ID NO: 42
TTTGGTGCGAAGCAGGCTGAGGC

SEQ ID NO: 43
TTTGGTGCGAAGCAGGGTGAGGC

SEQ ID NO: 44
TTTGGTGCGAAGCAGGTTGAGGC

SEQ ID NO: 45
TTTGGTGCGAAGCAGGATGAGGC

SEQ ID NO: 46
GCCUCAGTCTGCTTCGCACC

SEQ ID NO: 47
TTTGGTGCGAAGCAGAAGGTAAGCCGAGGTTTGGCC

SEQ ID NO: 48
MAITKPLLAATLENIEDVQFPCLATPKIDGIRSVKQTQMLSRTFKPIRNSVMNRLLTELLPEGSDG
EISIEGATFQDTTSAVMTGHKMYNAKFSYYWFDYVTDDPLKKYSDRVEDMKNYITAHPHILDHE
QVKIIPLIPVEINNITELLQYERDVLSKGFEGVMIRKPDGKYKFGRSTLKEGILLKMQFKDAEATII
SMTALFKNTNTKTKDNFGYSKRSTHKNGKVEEDVMGSIEVDYDGVVFSIGTGFDADQRRDFW
QNKESYIGKMVKFKYFEMGSKDCPRFPVFIGIRHEEDH

SEQUENCE LISTING

SEQ ID NO: 49
MTIAKPLLAATLENLDDVKFPCLVTPKIDCIRSLKQQHMLSRTFKPIRNSVMNKLLSELLPEGAD
GEICIEDSTFQATTSAVMTGHKVYDEKFSYYWFDYWDDPLKSYTDRVNDMKKYVDDHPHILE
HEQVKIIPLIPVEINNIDELSQYERDVLAKGFEGVMIRRPDGKYKFGRSTLKEGILLKMKQFKDAE
ATIISMSPRLKNTNAKSKDNLGYSKRSTHKSGKVEEETMGSIEVDYDGWFSIGTGFDDEQRKH
FWENKDSYIGKLLKFKYFEMGSKDAPRFPVFIGIRHEEDC

SEQ ID NO: 50
MTAIQKPLLAASFKKLTVADVKYPVFATPKLDGIRALKIDGAFVSRTFKPIRNRAIADALQDLLPN
GSDGEILSGSTFQDASSAVMTAKAGIGANTIFYWFDYVKDDPNKPYLDRMTDMENYLKERPEIL
NDDRIKIVPLIPKKIETKDELDTFEKICLDQGFEGVMIRSGAGKYKFGRSTEKEGILIKIKQFEDDE
AVVIGFTPMQTNTNDKSMNELGDMKRSSHKDGKVNLDTLGALEVDWNGITFSIGTGFDHALRD
KLWSERDKLIGKIVKFKYFAQGVKTAPRFPVFIGFRDPDDM

SEQ ID NO: 51
MAIQKPLLAASLKKMSVGDLTFPVFATPKLDGIRALKVGGTIVSRTFKPVRNSAISEVLASILPDG
SDGEILSGKTFQESTSTVMTADAGLGSGTMFFWFDYVKDDPNKGYLDRIADMKSFTDRHPEIL
KDKRVTIVPLFPKKIDTTEELHEFEKWCLDQGFEGVMVRNAGGKYKFGRSTEKEQILVKIKQFE
DDEAVVIGVSALQTNTNDKKLNQLGEMRRTSHQDGKVELEMLGALDVDWNGIRFSIGTGFDRD
TRVDLWKRREGVIGKIVKFKYFSQGIKTAPRFPVFLGFRDKDDM

SEQ ID NO: 52
MAIQKPLLAASLKKLSVDDLTFPVYATPKLDGIRALKIDGTLVSRTFKPIRNTTISKVLTSLLPDGS
DGEILSGKTFQDSTSTVMSADAGIGSGTTFFWFDYVKDDPNKGYLDRIADIKKFIDCRPEILKDS
RVIIVPLFPKKIDTAEELNVFEKWCLDQGFEGVMVRNAGGKYKFGRSTEKEQILVKIKQFEDDEA
VVIGVSALQTNTNDKKVNELGEMRRTSHQDGKVDLDMLGALDVDWNGIRFCIGTGFDKDTRE
DLWKRRDSIIGKIVKFKYFSQGVKTAPRFPVFLGFRDKNDM

SEQ ID NO: 53
MAIQKPLLAASLKKLSVDDLTFPVYATPKLDGIRALKIDGTIVSRTFKPIRNTTISNVLMSLLPDGS
DGEILSGKTFQDSTSTVMSADAGIGSGTTFFWFDYVKDDPDKGYLDRIADMKKFVDSHPEILKD
RRVTIVPLIPKKIDTVEELNVFEQWCLDQGFEGVMVRNAGGKYKFGRSTEKEQILVKIKQFEDD
EAWIGVSALQTNVNDKKMNELGDMRRTSHKDGKIDLEMLGALDVEWNGIRFGIGTGFDKDTR
EDLWKKRDSIIGKWKFKYFSQGIKTAPRFPVFLGFRDENDM

SEQ ID NO: 54
MAIQKPLLAASLKKMSVDNLTFPVYATPKLDGIRALKIDGTLVSRTFKPIRNTTISKVLASLLPDGS
DGEILSGKTFQDSTSTVMTTDAGIGSDTTFFWFDYVKDDPDKGYLDRIADMKTFVDQHPEILKD
SCVTIVPLFPKKIDTPEELHVFEKWCLDQGFEGVMVRTAGGKYKFGRSTEKEQILVKIKQFEDD
EAWIGVSALQTNTDKKLNQLGEMRRTSHQDGKVDLDMLGALDVDWNGIRFSIGTGFDKDTR
EDLWKQRDSIVGKVVKFKYFSQGIKTAPRFPVFLGFRDENDM

SEQ ID NO: 55
MAIQKPLLAASLKKMSVDDLTFPVYTTPKLDGIRALKIDGTLVSRTFKPVRNSAISEVLASLLPDG
SDGEILSGKTFQDSTSTVMTTDAGIGSDTTFFWFDYVKDDPNKGYLDRIADMKTFIDQHPEMLK
DNHVTIVPLIPKKIDTVEELNIFEKWCLDQGFEGVMVRNAGGKYKFGRSTEKEQILVKIKQFEDD
EAWIGVSALQTNTNDKKLNQLGEMRRTSHQDGKIDLEMLGALDVDWNGIRFSIGTGFDRDTR
VDLWKRRDGIVGRTIKFKYFGQGIKTAPRFPVFLGFRDKDDM

SEQ ID NO: 56
MLAGNFDPKKAKFPYCATPKIDGIRFLMVNGRALSRTFKPIRNEYIQKLLSKHLPDGIDGELTCG
DTFQSSTSAIMRIAGEPDFKAWIFDYVDPDSTSILPFIERFDQISDIIYNGPIPFKHQVLGQSILYNI
DDLNRYEEACLNEGYEGVMLRDPYGTYKFGRSSTNEGILLKVKRFEDAEATVIRIDEKMSNQNI
AEKDNFGRTKRSSCLDGMVPMETTGALFVRNSDGLEFSIGSGLNDEMRDEIWKNKSSYIGKLV
KYKYFPQGVKDLPRHPVFLGFRDPDDM

SEQ ID NO: 57
MDAHELMKLNEYAERQNQKQKKQITKPMLAASLKDITQLDYSKGYLATQKLDGIRALMIDGKLV
SRTFKPIRNNHIREMLEDVLPDGADGEIVCPGAFQATSSGVMSANGEPEFIYYMFDYVKDDITK
EYWRRTQDMVQWLINQGPTRTPGLSKLKLLVPTLIKNYDHLKTYETECIDKGFEGVILRTPDSP
YKCGRSTAKQEWLLKLKRFADDEAWIGFTEKMHNDNEATKDKFGHTVRSSHKENKRPAGTL
GSLIVRDIKTEIEFEIGTGFDDELRQKIWDARPEWDGLCVKYKHFAISGVKEKPRFPSFIGVRDV
EDM

SEQ ID NO: 58
MSSPDADQTAPEVLRQWQALAEEVREHQFRYYVRDAPIISDAEFDELLRRLEALEEQHPELRT
PDSPTQLVGGAGFATDFEPVDHLERMLSLDNAFTADELAAWAGRIHAEVGDAAHYLCELKIDG
VALSLVYREGRLTRASTRGDGRTGEDVTLNARTIADVPERLTPGDDYPVPEVLEVRGEVFFRL
DDFQALNASLVEEGKAPFANPRNSAAGSLRQKDPAVTARRRLRMICHGLGHVEGFRPATLHQ
AYLALRAWGLPVSEHTTLATDLAGVRERIDYWGEHRHEVDHEIDGVVVKVDEVALQRRLGSTS
RAPRWAIAYKYPPEEAQTKLLDIRVNVGRTGRITPFAFMTPVKVAGSTVGQATLHNASEIKRKG
VLIGDTVVIRKAGDVIPEVLGPVVELRDGSEREFIMPTTCPECGSPLAPEKEGDADIRCPNARGC
PGQLRERVFHVASRNGLDIEVLGYEAGVALLQAKVIADEGELFALTERDLLRTDLFRTKAGELS
ANGKRLLVNLDKAKAAPLWRVLVALSIRHVGPTAARALATEFGSLDAIAAASTDQLAAVEGVGP
TIAAAVTEWFAVDWHREIVDKWRAAGVRMVDERDESVPRTLAGLTIVVTGSLTGFSRDDAKEAI
VARGGKAAGSVSKKTNYVVAGDSPGSKYDKAVELGVPILDEDGFRRLLADGPASRT

SEQUENCE LISTING

```
SEQ ID NO: 59
MEQQPLTLTAATTRAQELRKQLNQYSHEYYVKDQPSVEDYVYDRLYKELVDIETEFPDLITPDS
PTQRVGGKVLSGFEKAPHDIPMYSLNDGFSKEDIFAFDERVRKAIGKPVAYCCELKIDGLAISLR
YENGVFVRGATRGDGTVGENITENLRTVRSVPMRLTEPISVEVRGECYMPKQSFVALNEEREE
NGQDIFANPRNAAAGSLRQLDTKIVAKRNLNTFLYTVADFGPMKAKTQFEALEELSAIGFRTNP
ERQLCQSIDEVWAYIEEYHEKRSTLPYEIDGIVIKVNEFALQDELGFTVKAPRWAIAYKFPPEEA
ETVVEDIEVVTIGRTGVVTPTAVMAPVRVAGTTVSRASLHNADFIQMKDIRLNDHVIIYKAGDIIPE
VAQVLVEKRAADSQPYEMPTHCPICHSELVHLDEEVALRCINPKCPAQIKEGLNHFVSRNAMNI
DGLGPRVLAQMYDKGLVKDVADLYFLTEEQLMTLDKIKEKSANNIYTAIQGSKENSVERLIFGLG
IRHVGAKAAKILAEHFGDLPTLSRATAEEIVALDSIGETIADSVVTYFENEEVHELMAELEKAQVN
LTYKGLRTEQLAEVESPFKDKTVVLTGKLAQYTREEAKEKIENLGGKVTGSVSKKTDIVVAGED
AGSKLTKAESLGVTVWNEQEMVDALDASHF

SEQ ID NO: 60
MTNIQTQLDNLRKTLRQYEYEYHVLDNPSVPDSEYDRLFHQLKALELEHPEFLTSDSPTQRVG
AKPLSGFSQIRHEIPMLSLDNAFSDAEFNAFVKRIEDRLILLPKPLTFCCEPKLDGLAVSILYVNG
ELTQAATRGDGTTGEDITANIRTIRNVPLQLLTDNPPARLEVRGEVFMPHAGFERLNKYALEHN
EKTFANPRNAAAGSLRQLDPNITSKRPLVLNAYGIGIAEGVDLPTTHYARLQWLKSIGIPVNPEIR
LCNGADEVLGFYRDIQNKRSSLGYDIDGTVLKINDIALQNELGFISKAPRWAIAYKFPAQEELTLL
NDVEFQVGRTGAITPVAKLEPVFVAGVTVSNATLHNGDEIERLNIAIGDTVVIRRAGDVIPQIIGVL
HERRPDNAKPIIFPTNCPVCDSQIIRIEGEAVARCTGGLFCAAQRKEALKHFVSRKAMDIDGVG
GKLIEQLVDRELIHTPADLFKLDLTTLTRLERMGAKSAENALNSLENAKSTTLARFIFALGIREVG
EATALNLANHFKTLDALKDANLEELQQVPDVGEWANRIFIFWREAHNVAVVEDLIAQGVHWET
VEVKEASENLFKDKTVVLTGTLTQMGRNEAKALLQQLGAKVSGSVSSKTDFVIAGDAAGSKLA
KAQELNITVLTEEEFLAQITR

SEQ ID NO: 61
MADLSSRVNELHDLLNQYSYEYYVEDNPSVPDSEYDKLLHELIKIEEEHPEYKTVDSPTVRVGG
EAQASFNKVNHDTPMLSLGNAFNEDDLRKFDQRIREQIGNVEYMCELKIDGLAVSLKYVDGYF
VQGLTRGDGTTGEDITENLKTIHAIPLKMKEPLNVEVRGEAYMPRRSFLRLNEEKEKNDEQLFA
NPRNAAAGSLRQLDSKLTAKRKLSVFIYSVNDFTDFNARSQSEALDELDKLGFTTNKRARVN
NIDGVLEYIEKWTSQRESLPYDIDGIVIKVNDLDQQDEMGFTQKSPRWAIAYKFPAEEVVTKLLD
IELSIGRTGVVTPTAILEPVKVAGTTVSRASLHNEDLIHDRDIRIGDSVVVKKAGDIIPEVVRSIPER
RPEDAVTYHMPTHCPSCGHELVRIEGEVALRCINPKCQAQLVEGLIHFVSRQAMNIDGLGTKIIQ
QLYQSELIKDVADIFYLTEEDLLPLDRMGQKKVDNLLAAIQQAKDNSLENLLFGLGIRHLGVKAS
QVLAEKYETIDRLLTVTEAELVEIHDIGDKVAQSVVTYLENEDIRALIQKLKDKHVNMIYKGIKTSD
IEGHPEFSGKTIVLTGKLHQMTRNEASKWLASQGAKVTSSVTKNTDVVIAGEDAGSKLTKAQSL
GIEIVVTEQQFVDKQNELNS

SEQ ID NO: 62
MNKRMNELVALLNRYATEYYTSDNPSVSDSEYDRLYRELVELETAYPEQVLADSPTHRVGGKV
LDGFEKYSHQYPLYSLQDAFSREELDAFDARVRKEVAHPTYICELKIDGLSISLTYEKGILVAGVT
RGDGSIGENITENLKRVKDIPLTLPEELDITVRGECYMPRASFDQVNQARQENGEPEFANPRNA
AAGTLRQLDTAVVAKRNLATFLYQEASPSTRDSQEKGLKYLEQLGFVVNPKRILAENIDEIWNFI
QEVGQERENLPYDIDGVVIKVNDLASQEELGFTVKAPKWAVAYKFPAEEKEAQLLSVDWTVGR
TGVVTPTANLTPVQLAGTTVSRATLHNVDYIAEKDIRKDDTVIVYKAGDIIPAVLRVVESKRVSEE
KLDIPTNCPSCNSDLLHFEDEVALRCINPRCPAQIMEGLIHFASRDAMNITGLPSIVEKLFAANL
VKDVADIYRLQEEDFLLLEGVKEKSAAKLYQAIQASKENSAEKLLFGLGIRHVGSKASQLLLQYF
HSIENLYQADSEEVASIESLGGVIAKSLQTYFATEGSEILLRELKETGVNLDYKGQTVVADAALS
GLTVVLTGKLERLKRSEAKSKLESLGAKVTGSVSKKTDLVVVGADAGSKLQKAQELGIQVRDEA
WLESL
```

---

The invention claimed is:

1. A continuous or semi-continuous flow process for purifying a single-stranded oligonucleotide product from impurity oligonucleotide strands, wherein the single-stranded oligonucleotide product has at least one modified nucleotide residue, wherein the modification is chosen from: modification at the 2' position of the sugar moiety of the nucleotide residue, modification of the nucleobase of the nucleotide residue, and modification of the backbone of the nucleotide residue, the process comprising:
   a) providing a template oligonucleotide (I) complementary to the sequence of the single-stranded oligonucleotide product, said template having properties that allow it to be separated from the single-stranded oligonucleotide product;
   b) providing a pool of oligonucleotides (II) comprising the single-stranded oligonucleotide product and impurity oligonucleotide strands;
   c) contacting the template oligonucleotide (I) and the pool of oligonucleotides (II) in conditions to allow annealing, thereby producing (i) annealed template and impurity oligonucleotide strands and (ii) annealed template and single-stranded oligonucleotide product;
   d) changing the conditions to separate any impurity oligonucleotide strands, comprising denaturing the annealed template and impurity oligonucleotide strands;
   e) separating the impurity oligonucleotide strands from the annealed template and single-stranded oligonucleotide product;
   f) changing the conditions to separate the single-stranded oligonucleotide product, comprising denaturing the annealed template and single-stranded oligonucleotide product;
   g) separating the single-stranded oligonucleotide product from the template; and
   h) recycling the template.

2. The process according to claim 1, whereby the denaturing results from a temperature increase, changing pH, or changing a salt concentration in a buffering solution.

3. The process according to claim 1, including two steps of increasing temperature: i) to denature any annealed impurities and ii) to denature annealed product.

4. The process according to claim 1, wherein the single-stranded oligonucleotide product is 10 to 200 nucleotides long.

5. The process according to claim 1, wherein a property that allows the template to be separated from the single-stranded oligonucleotide product is that the template is attached to a support material.

6. The process according to claim 5, wherein the support material is a soluble support material.

7. The process according to claim 6, wherein the soluble support material is selected from the group consisting of polyethylene glycol, a soluble organic polymer, DNA, a protein, a dendrimer, a polysaccharide, an oligosaccharide, and a carbohydrate.

8. The process according to claim 5, wherein the support material is an insoluble support material.

9. The process according to claim 8, wherein the support material is selected from the group consisting of: a glass bead, a polymeric bead, a fibrous support, a membrane, a streptavidin coated bead, cellulose, and a reaction vessel.

10. The process according to claim 5, wherein multiple, repeated copies of the template are attached in a continuous manner via a single attachment point to the support material.

11. The process according to claim 1, wherein a property that allows the template to be separated from the product is the molecular weight of the template.

12. The process according to claim 1, wherein the modification is selected from the group consisting of 2'-Fluoro (2'-F), 2'-O-methyl (2'-OMe), 2-O-methoxyethyl (2'-MOE), and 2'-amino, or wherein the oligonucleotide comprises a phosphorodiamidate morpholino oligomer (PMO), a locked nucleic acid (LNA), a peptide nucleic acid (PNA), and a bridged nucleic acid (BNA).

13. The process according to claim 1, wherein the modification is selected from the group consisting of a 5-methyl pyrimidine, a 7-deazaguanosine and an abasic nucleotide.

14. The process according to claim 1, wherein the modification is selected from the group consisting of phosphorothioate, phosphoramidate and phosphorodiamidate.

15. The process according to claim 1, wherein the single-stranded oligonucleotide product is at least 90% pure.

16. The process according to claim 1, wherein the process is for purifying a therapeutic oligonucleotide.

17. The process according to claim 1, wherein the product is purified at gram or kilogram scale and/or the process is carried out in a 1 L or larger reactor.

18. The process according to claim 1, wherein the single-stranded oligonucleotide product is 20 to 30 nucleotides long.

19. The process according to claim 1, wherein the single-stranded oligonucleotide product is at least 95% pure.

20. The process according to claim 1, wherein the single-stranded oligonucleotide product is at least 98% pure.

* * * * *